United States Patent
Akullian et al.

(10) Patent No.: US 8,399,512 B2
(45) Date of Patent: Mar. 19, 2013

(54) BIOCOMPATIBLE BIODEGRADABLE FUMAGILLIN ANALOG CONJUGATES

(75) Inventors: Laura C. Akullian, Belmont, MA (US); Russell C. Petter, Stow, MA (US); John J. Kane, Queens Village, NY (US); Charles E. Hammond, Billerica, MA (US); Mao Yin, Needham, MA (US); Aleksandr Yurkovetskiy, Littleton, MA (US); Cheri A. Stevenson, Haverhill, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 894 days.

(21) Appl. No.: 12/276,856

(22) Filed: Nov. 24, 2008

(65) Prior Publication Data

US 2009/0148396 A1 Jun. 11, 2009

Related U.S. Application Data

(60) Provisional application No. 61/004,582, filed on Nov. 28, 2007.

(51) Int. Cl.
A61K 31/335 (2006.01)
C07D 303/00 (2006.01)

(52) U.S. Cl. .................... 514/475; 549/332
(58) Field of Classification Search .......... 514/475; 549/332

See application file for complete search history.

(56) References Cited

U.S. PATENT DOCUMENTS

| | | |
|---|---|---|
| 2,803,586 A | 8/1957 | Peterson et al. |
| 5,164,410 A | 11/1992 | Kishimoto et al. |
| 5,180,735 A | 1/1993 | Kishimoto et al. |
| 5,180,738 A | 1/1993 | Kishimoto et al. |
| 5,290,807 A | 3/1994 | Folkman et al. |
| 5,422,363 A | 6/1995 | Yanai et al. |
| 5,698,586 A | 12/1997 | Kishimoto et al. |
| 5,767,293 A | 6/1998 | Oku et al. |
| 5,789,405 A | 8/1998 | Oku et al. |
| 5,811,510 A | 9/1998 | Papisov |
| 5,863,990 A | 1/1999 | Papisov |
| 5,900,431 A | 5/1999 | Molina et al. |

(Continued)

FOREIGN PATENT DOCUMENTS

| | | |
|---|---|---|
| EP | 0354787 | 2/1990 |
| WO | WO-99/61432 | 12/1999 |

(Continued)

OTHER PUBLICATIONS

Akullian et al, Anti-Angiogenic Fumagillin-Related Polymeric Pro-Drugs exhibit Anti-Tumor Activity in B16 Murine Melanoma and Human Tumor Xenograft Models, Proc. Am. Assoc. Cancer Research 2007 (Apr. 2007); abstr 2327, p. 1.*

(Continued)

Primary Examiner — Taylor Victor Oh
(74) Attorney, Agent, or Firm — John P. White; Gary J. Gershik; Cooper & Dunham LLP

(57) ABSTRACT

Fumagillin analog polymer conjugates, methods of making fumagillin analog polymer conjugates, compositions comprising a polymer conjugate of a fumagillin analog, and methods for treating cancer, or treating angiogenic diseases comprising administering to a subject in need thereof an effective amount of a polymer conjugate of a fumagillin analog, are described. Also described are novel fumagillin analogs, methods of making fumagillin analogs, compositions comprising at least one fumagillin analog, and methods for treating cancer, or treating angiogenic diseases comprising administering to a subject in need thereof an effective amount of a fumagillin analog.

50 Claims, 6 Drawing Sheets

U.S. PATENT DOCUMENTS

| | | |
|---|---|---|
| 5,958,398 A | 9/1999 | Papisov |
| 6,017,954 A | 1/2000 | Folkman et al. |
| 6,040,337 A | 3/2000 | Hong et al. |
| 6,063,812 A | 5/2000 | Hong et al. |
| 6,207,704 B1 | 3/2001 | Liu et al. |
| 6,521,764 B1 | 2/2003 | Farkas et al. |
| 6,528,539 B1 | 3/2003 | Abramovici et al. |
| 6,548,477 B1 | 4/2003 | Olson et al. |
| 6,566,541 B2 | 5/2003 | Liu et al. |
| 6,603,812 B1 | 8/2003 | Oprescu |
| 6,740,678 B2 | 5/2004 | Moulton et al. |
| 6,803,382 B2 | 10/2004 | Eustache et al. |
| 6,822,086 B1 | 11/2004 | Papisov |
| 6,919,307 B2 | 7/2005 | Olson et al. |
| 6,949,584 B2 | 9/2005 | Satchi-Fainaro et al. |
| 7,037,890 B2 | 5/2006 | Olson et al. |
| 7,084,108 B2 | 8/2006 | Olson et al. |
| 7,105,482 B2 | 9/2006 | Olson et al. |
| 7,157,420 B2 | 1/2007 | Olson et al. |
| 7,160,924 B2 | 1/2007 | Kinstler et al. |
| 7,268,111 B2 | 9/2007 | Olson et al. |
| 7,332,523 B2 | 2/2008 | Satchi-Fainaro et al. |
| 7,348,307 B2 | 3/2008 | Olson et al. |
| 7,396,953 B2 | 7/2008 | Eustache et al. |
| 7,405,194 B2 | 7/2008 | Olson et al. |
| 2004/0029130 A1 | 2/2004 | West et al. |
| 2004/0105840 A1 | 6/2004 | Kinstler et al. |
| 2005/0169968 A1 | 8/2005 | Elmaleh et al. |
| 2006/0019911 A1 | 1/2006 | Papisov |
| 2006/0058513 A1 | 3/2006 | Papisov |
| 2006/0069230 A1 | 3/2006 | Papisov |
| 2007/0190018 A1 | 8/2007 | Papisov |
| 2008/0019940 A1 | 1/2008 | Papisov |
| 2009/0054430 A1 | 2/2009 | Dai et al. |
| 2009/0156624 A1 | 6/2009 | Olson et al. |
| 2009/0246211 A1 | 10/2009 | Henri et al. |
| 2010/0305149 A1 | 12/2010 | Yurkovetskiy et al. |

FOREIGN PATENT DOCUMENTS

| | | |
|---|---|---|
| WO | WO-03/086382 A1 | 10/2003 |
| WO | WO-2005/023294 A1 | 3/2005 |
| WO | WO 2009/073445 | 7/2009 |

OTHER PUBLICATIONS

Kockerbauer et al., "A novel approach to preparing water soluble prodrug forms of cisplatin analogues bearing chelating diamines" Journal of Pharmaceutical Sciences 1995 vol. 84, No. 7, pp. 819-823.

Satchi-Fainaro et al., "Targeting angiogenesis with a conjugate of HPMA Copolymer and TNP-470" Nature Medicine 2004 10(3) 255-261.

Akullian, et al., "Abstract #2327: Fumagillin-derived polymeric prodrugs exhibit anti-tumor activity in B16 murine melanoma and in A2058 and PC3 human tumor xenograft models," 99th AACR Annual Meeting, 2008, San Diego, CA, Retrieved from the Internet: URL:http://www.aacrmeetingabstracts.org/cgi/content/meeting_abstract/2008/1_Annual_Meeting/2327?maxtoshow=&HITS=10&hits=10RESULTFORMAT=1&andorexacttitle=and&andorexacttitleabs+and&searchid=1&FIRSTINDEX=0&sortspec=relevance&fdate=1/1/2004&tdate=12/31/2008&resourcetype=HWCIT>[retrieved on Sep. 1, 2009]abstract, 2 pages.

Bernier, et al., "Fumagillin class inhibitors of methionine aminopeptidase-2," Drugs of the Future, vol. 30, No. 5, May 2005, pp. 497-508.

International Search Report and Written Opinion from the European Patent Office as the International Searching Authority for PCT/US2008/084539, mailing date Sep. 12, 2009, 17 pages.

Partial International Search Report of the European Patent Office as the International Searching Authority for PCT/US2008/084539, mailed on Sep. 24, 2009, 3 pages.

Pyun, et al., "Investigation of novel fumagillin analogues as angiogenesis inhibitors," Bioorganic and Medicinal Chemistry Letters, vol. 14, No. 1, Jan. 2004, pp. 91-94.

Yasukawa, et al., "Targeted delivery of anti-angiogenic agent TNP-470 using water-soluble polymer in the treatment of choroidal neovascularization," Investigative Ophthalmology & Visual Science, Association for Research in Vision and Ophthalmology, vol. 40, No. 11, Oct. 1999, pp. 2690-2696.

Anderson, et al., "Efficient Diastereoselective Synthesis of Either Form of meso-2,6-Dimethylcyclo-Hexane Carboxaldehyde," Synthetic Communications, 31(6), 939-946, 2001, 8 pages.

Buchwald, et al., "Long-term, continuous intravenous heparin administration by an implantable infusion pump in ambulatory patients with recurrent venous thrombosis," Surgery, 507, 1980, 11 pages.

Camara, et al., "Oxacarbenium Ion Cyclizations for C-Branched Cyclitols: Synthesis of a Relay Intermediate for Fumagillin Analogues," J. Org. Chem., 2005, 70, pp. 6870-6875, 6 pages.

During, et al., "Controlled Release of Dopamine from a Polymeric Brain Implant: In Vivo Characterization," Annals of Neurology, vol. 25, No. 4, Apr. 1989, 7 pages.

Fardis, et al., "Design, Synthesis and Evaluation of a Series of Novel Fumagillin Analogues," Biorganic & Medicinal Chemistry, 11, 2003, pp. 5051-5058, 8 pages.

Folkman, "How is Blood Vessel Growth Regulated in Normal and Neoplastic Tissue?-G.H.A. Clowes Memorial Award Lecture." Cancer Research, vol. 46, Feb. 1986, pp. 467-473, 8 pages.

Folkman, "What is the Evidence that Tumors are Angiogenesis Dependent?" Journal of the National Cancer Institute, vol. 82, No. 1, 1990, 4 pages.

Folkman, et al., "Angiogenic Factors," Science, vol. 235, 1987, 6 pages.

Folkman, et al., "Minireview: Angiognesis," The Journal of Biological Chemistry, vol. 267, No. 16, 1992, pp. 10931-10934, 4 pages.

Goodson, "Dental Applications," Medical Applications of Controlled Release, vol. II Applications and Evaluation, 26 pages, 1984.

Howard, et al., "Intracerebral drug delivery in rats with lesion-induced memory deficits," J. Neurosurg, vol. 71:105-112, 1989, 9 pages.

Langer, "New Methods of Drug Delivery," Science, Articles, 1990, 7 pages.

Levy, "Inhibition of Calcification of Bioprosthetic Heart Valves by Local Controlled-Release Diphosphonate," Science, vol. 228, 1985, 3 pages.

Liu, et al., "Structure of Human Methionine Aminopeptidase-2 Complexed with Fumagillin," Science, 282, 1324, 1998, 5 pages.

Lu, et al., "Fumarranol, a Rearranged Fumagillin Analogue that Inhibits Angiogenesis in Vivo," Journal of Medicinal Chemistry, 2006, vol. 49, No. 19, 4 pages.

Picoul, et al., "A Novel Stereoselective Route to a Fumagillin and Ovalicin Synthetic Intermediate," Tetrahedron Letters, 40, 1999, pp. 4797-4800, 4 pages.

Popov, et al., "The Effect of Stresses on Polymer Oxidation. Quantitative Aspects. 1. Elastomers," JMS-Rev. Macromol. Chem. Phys., C23(1), 1-32, 1983, 68 pages.

Rodeschini, et al., "MetAP-2 Inhibitors Based on the Fumagillin Structure. Side-Chain Modification and Ring-Substituted Analogues," J. Org. Chem., 2004, 69, 357-373, 17 pages.

Saudek, et al., "A Preliminary Trial of the Programmable Implantable Medication System for Insulin Delivery," The New England Journal of Medicine, vol. 321, No. 9, 1989, 7 pages.

Sefton, "Implantable Pumps," CRC Critical Reviews in Biomedical Engineering, vol. 14, Issue 3, 41 pages, 1987.

Turner, et al., "The Stereochemistry of Fumagillin," Proceedings of the National Academy of Sciences of the United States of America, vol. 48, 1962, 4 pages.

Weidner, et al., "Tumor Angiogenesis and Metastasis—Correlation in Invasive Breast Carcinoma," The New England Journal of Medicine, vol. 324, No. 1, Jan. 1991, 9 pages.

May 30, 2012 Examination Report issued in connection with counterpart New Zealand Patent Application No. 585547 (including claims pending in New Zealand at the time of the May 30, 2012 Examination Report).

May 28, 2012 Response to First Office Action in connection with counterpart Chinese Patent Application No. 20080122126.9 (including English language draft transmitted to Chinese associate for preparation of the Response).

* cited by examiner

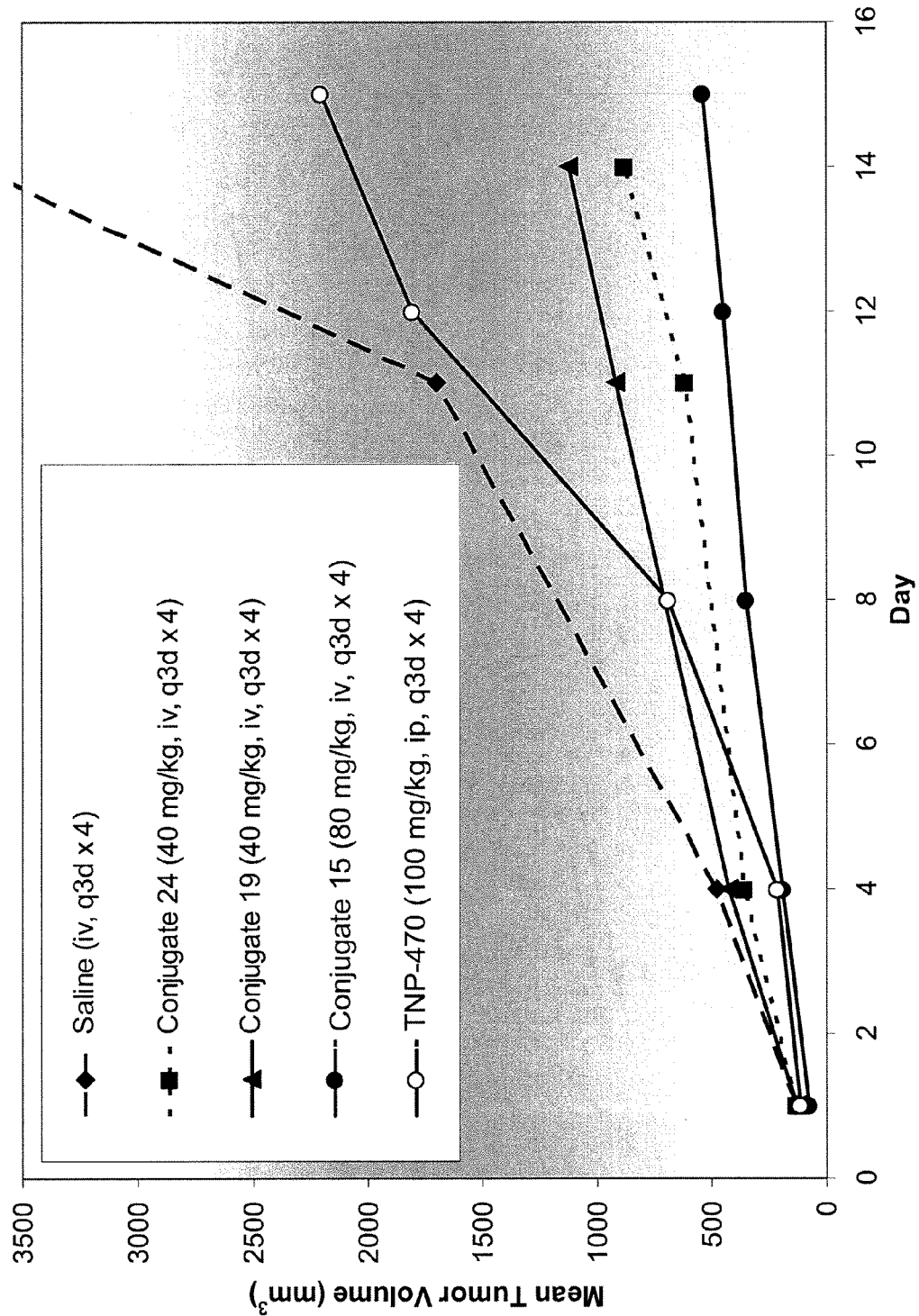

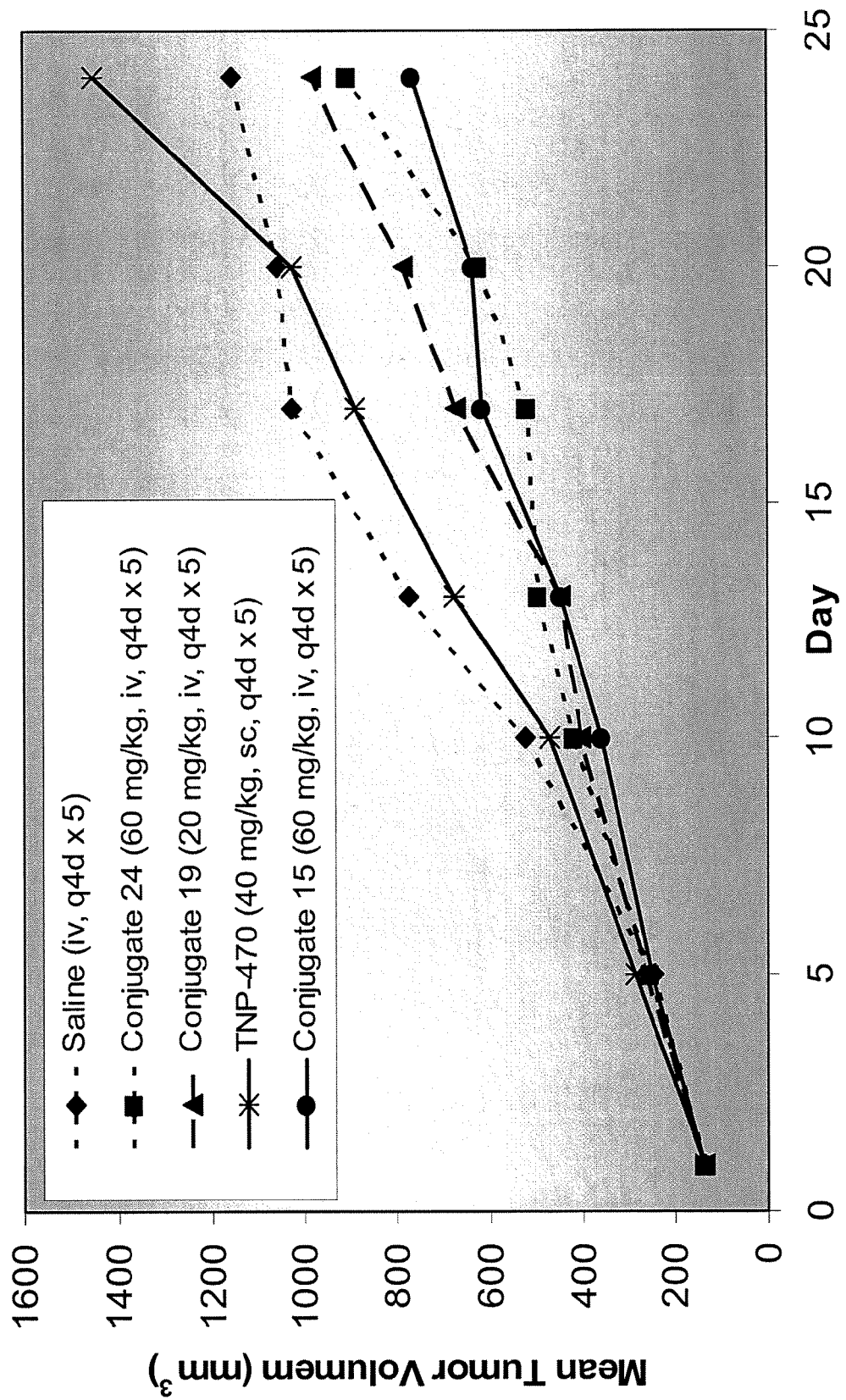
Figure 2: Activity of Fumagillin Conjugates Against A2058 Human Melanoma

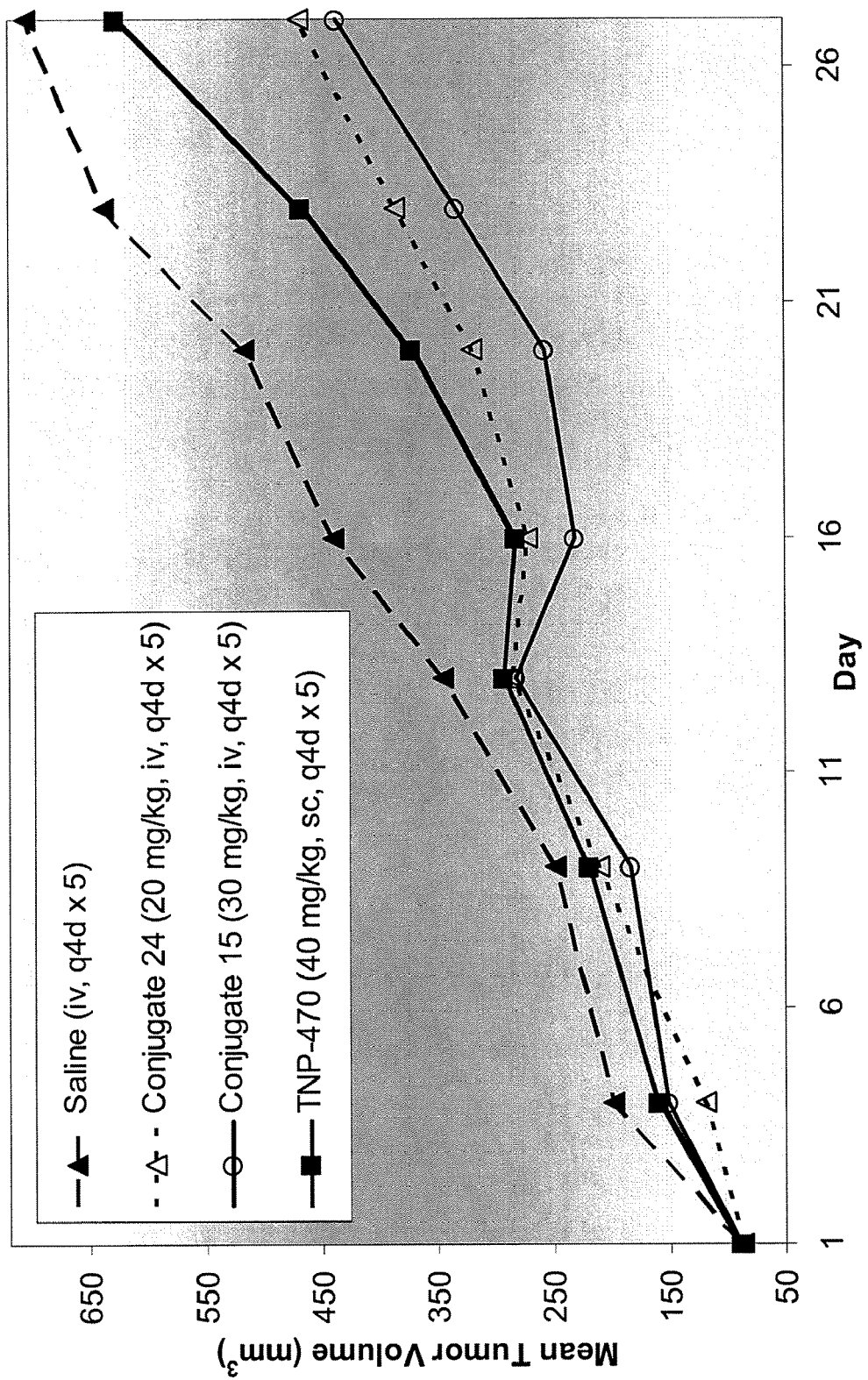
Figure 3: Activity of Fumagillin Conjugates Against PC3 Human Prostate Cancer

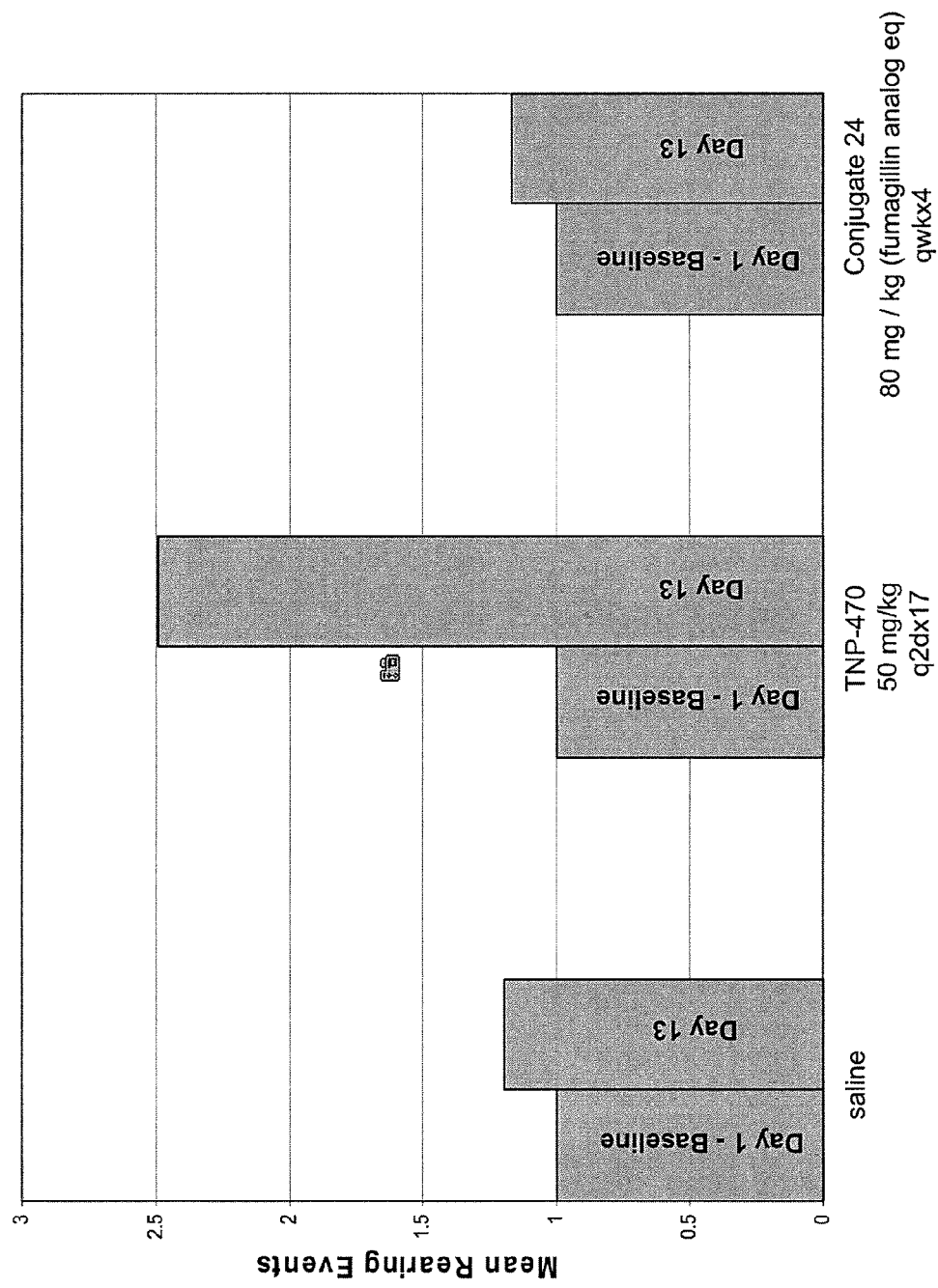
Figure 4: Mean Rearing Events (normalized to day 1 baseline activity) on Study Day 13 for TNP-470 and Conjugate 24

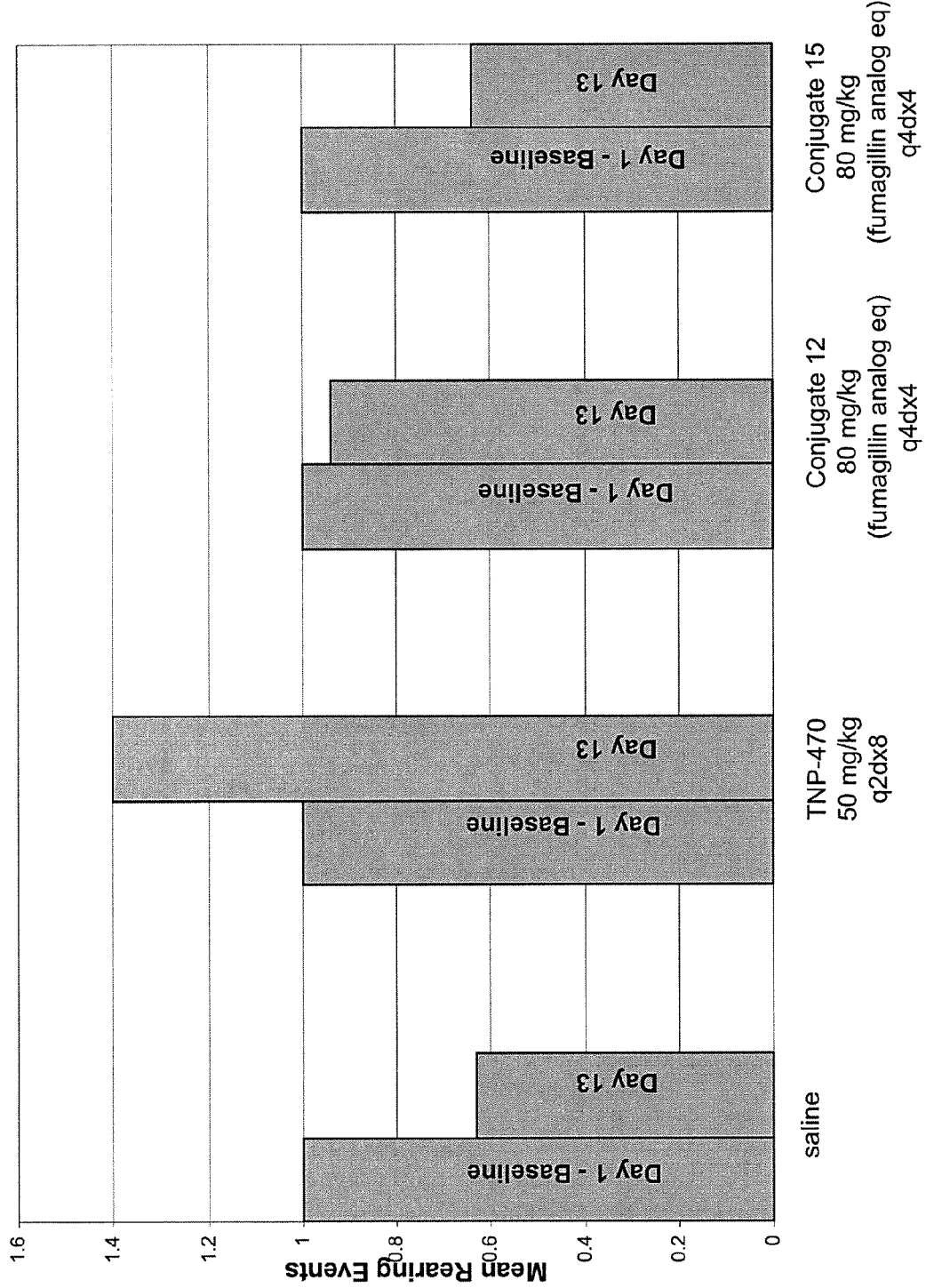

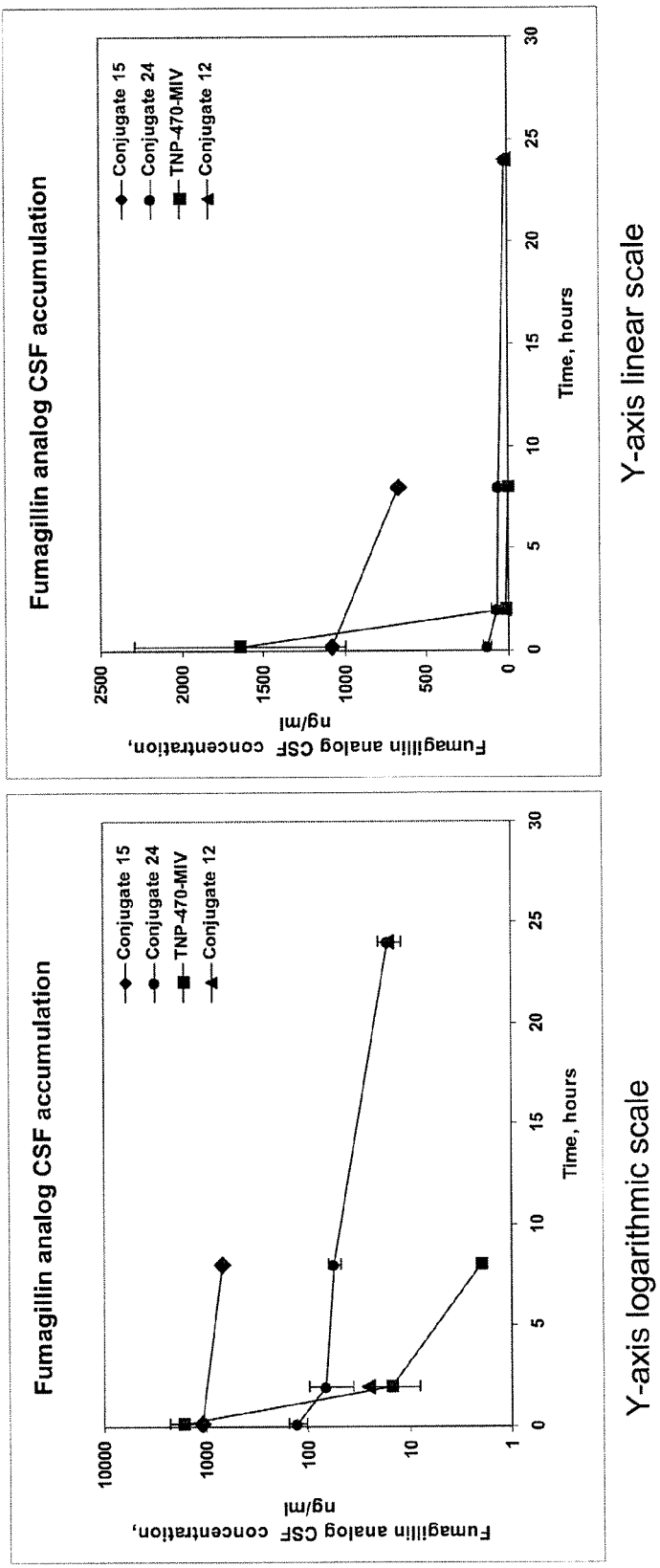
Figure 6: CSF accumulation of fumagillin analogs after dosing conjugate 12, conjugate 15, and conjugate 24
Data normalized to a dose of 40 mg/kg (fumagillin analog equivalents); data represent the concentration of free fumagillin analog observed. TNP-470 MIV is a known metabolite of TNP-470.

BIOCOMPATIBLE BIODEGRADABLE FUMAGILLIN ANALOG CONJUGATES

CROSS REFERENCE TO RELATED APPLICATIONS

This application claims the benefit of priority under 35 U.S.C. §119(e) to co-pending U.S. application No. 61/004,582, filed on Nov. 28, 2007, entitled "Biocompatible Biodegradable Fumagillin Analog Conjugates," which is incorporated in its entirety by reference.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

Polymer conjugates of fumagillin analogs, compositions comprising a fumagillin analog conjugate, and fumagillin analogs are described herein. Methods for treating or preventing cancer, or treating an angiogenic disease, comprising the administration of an effective amount of a fumagillin analog conjugate, are also described. Methods for treating or preventing cancer or treating an angiogenic disease, comprising the administration of an effective amount of a fumagillin analog, are also described.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods which may last for as long as weeks or in some cases, decades. When necessary, however, (such as during wound repair), these same cells can undergo rapid proliferation and turnover within a five day period (Folkman, J. and Shing, Y., (1992) *Journal of Biological Chemistry,* 267(16): 10931-10934, and Folkman, J. and Klagsbrun, M., (1987) *Science,* 235: 442-447).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, growth and metastasis of solid tumors are angiogenesis-dependent (Folkman, J., (1986) *Cancer Research,* 46: 467-473 and Folkman, J., (1989) *Journal of the National Cancer Institute,* 82: 4-6). It has been shown that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites, such as the liver, lung or bone (Weidner, N., et al., (1991) *The New England Journal of Medicine,* 324(1):1-8). In another example, ocular neovascularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness.

Fumagillin is a known compound which has been used as an antimicrobial and antiprotozoal. Its physicochemical properties and method of production are well known (U.S. Pat. No. 2,803,586 and Turner, J. and Tarbell, J., (1962) *Proc. Nat. Acad. Sci. USA,* 48: 733-735). Fumagillin and certain types of Fumagillin analogs have also been reported to exhibit anti-angiogenic activity. However, the use of such inhibitors (e.g., TNP-470) may be limited by their rapid metabolic degradation, erratic blood levels, and by dose-limiting central nervous system (CNS) side effects. Additionally, these molecules have physical and chemical properties that make them undesirable as therapeutics, for example, low water solubility, very short half-life values, unacceptable neurotoxic side-effects, and possible disruption of normal angiogenic processes.

One objective in the field of drug delivery systems is to deliver medications intact to specifically targeted areas of the body through a system that can control the rate and time of administration of the therapeutic agent by means of either a physiological or chemical trigger. Over the past decade, materials such as polymeric microspheres, polymer micelles, soluble polymers and hydrogel-type materials have been shown to be effective in enhancing drug targeting specificity, lowering systemic drug toxicity, improving treatment absorption rates, and providing protection for pharmaceuticals against biochemical degradation, and thus have shown great potential for use in biomedical applications, particularly as components of drug delivery devices.

Despite the known usefulness of fumagillin derivatives, they have not been used successfully as treatments because of the failure to overcome the problems of the low water solubility, short half-life values, and neurotoxic side-effects of these compounds. Accordingly, there is still a need for angiogenesis inhibitors which are more potent, less neurotoxic, more stable, and/or have longer serum half-lives than presently known angiogenesis inhibitors. The combination of drug delivery platform technology and fumagillin derivatives produces new agents useful in the treatment of diseases and disease states associated with angiogenesis.

DESCRIPTION OF THE FIGURES

FIG. 1 depicts the activity of fumagillin conjugates against B16-melanoma cells in a mouse model.

FIG. 2 depicts the activity of fumagillin conjugates against A2058 human melanoma cells in a mouse model.

FIG. 3 depicts the activity of fumagillin conjugates against PC3 human prostate cancer cells in a mouse model.

FIG. 4 and FIG. 5 depict the effect of fumagillin conjugates on behavior patterns in mice using an Open Field Behavioral Events assay.

FIG. 6 depicts fumagillin conjugates (Fm-analog) accumulation in rat CSF.

SUMMARY OF THE INVENTION

In one aspect, biocompatible biodegradable conjugates are provided which comprise at least one fumagillin analog conjugated directly or indirectly to a water soluble polyal, the conjugate having the structure of Formula I:

[fumagillin analog]$_m$-polyal   I wherein fumagillin analog is any fumagillin core structure which demonstrates MetAP-2 inhibition;

m is an integer from 1 to 40; and polyal is any polymer having at least one acetal oxygen atom or ketal oxygen atom in each monomer unit positioned within the main chain of the polymer.

In some embodiments, the fumagillin analog is represented by the Formula hA:

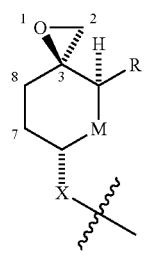

IIA wherein

X is O, S(=O)$_q$, optionally substituted CH$_2$, or optionally substituted NH;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C$_2$-heterocyclic-C$_1$-C$_6$ alkyl, C$_2$-heterocyclic-C$_2$-C$_6$ alkenyl, C$_1$-C$_6$ alkyl, C$_2$-C$_6$ alkenyl, C$_2$-heterocyclic-C$_1$-C$_6$-alkenyl-COO—C$_1$-C$_6$ alkyl, C$_2$-heterocyclic-C$_1$-C$_6$ alkyl-COO—C$_1$-C$_6$-alkyl, C$_1$-C$_6$ alkyl=N—O—C$_1$-C$_6$ alkyl-aryl, C(O)C$_1$-C$_6$ alkyl, CN, or halogen;

M is O, or

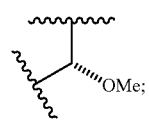

q is 0, 1, or 2; and the fumagillin core structure can be optionally substituted at C-7 and C-8, independently, with C$_1$-C$_6$ alkyl, C$_2$-C$_6$ alkenyl, C$_2$-C$_6$ alkynyl, OH, ketone, or alkoxy.

In some embodiments, the fumagillin analog of the conjugate has the core structure A:

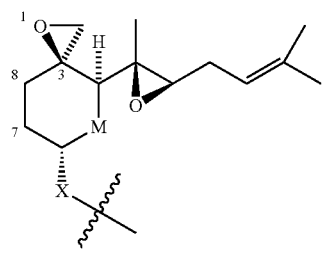

A wherein C-7 and C-8 are optionally substituted;

X is O, S(=O)$_q$, optionally substituted NH, or optionally substituted CH$_2$;

M is O, or

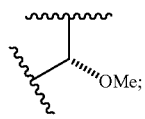

q is 0, 1, or 2; and the fumagillin analog is directly or indirectly attached to the polyal through X.

In other embodiments, the fumagillin analog of the conjugate has the core structure B:

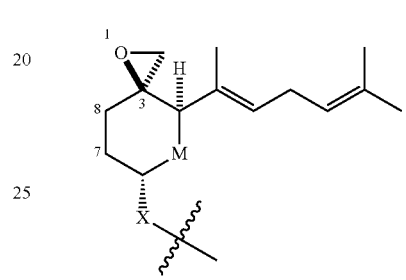

B wherein C-7 and C-8 are optionally substituted;

X is O, S(=O)$_q$, optionally substituted NH, or optionally substituted CH$_2$;

M is O, or

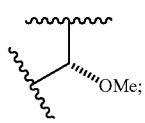

q is 0, 1, or 2; and the fumagillin analog is directly or indirectly attached to the polyal through X.

In still other embodiments, the fumagillin analog of the conjugate has the core structure C:

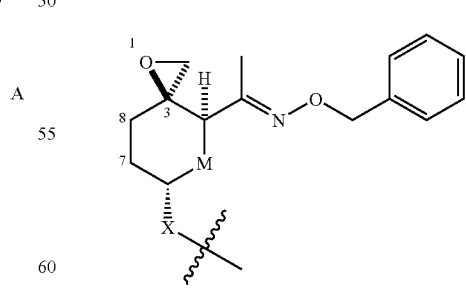

C wherein C-7 and C-8 are optionally substituted;

X is O, S(=O)$_q$, optionally substituted NH, or optionally substituted CH$_2$;

M is O, or

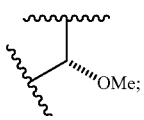

q is 0, 1, or 2; and the fumagillin analog is directly or indirectly attached to the polyal through X.

In some embodiments, the polyal has the structure

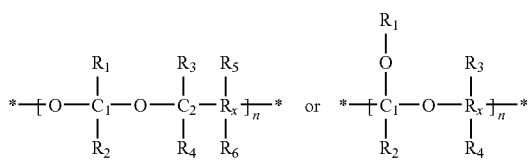

wherein for each occurrence of the n bracketed structure, either one of $R_1$ and $R_2$ is hydrogen, and the other is a biocompatible group and includes a carbon atom covalently attached to $C_1$ or each occurrence of $R_1$ and $R_2$ is a biocompatible group and includes a carbon atom covalently attached to $C_1$;

$R_x$ includes a carbon atom covalently attached to $C_2$;

n is an integer;

each occurrence of $R_3$, $R_4$, $R_5$, and $R_6$ is a biocompatible group and is independently hydrogen or an organic moiety; and for each occurrence of the bracketed structure n, at least one of $R_1$, $R_2$, $R_3$, $R_4$, $R_5$, and $R_6$ comprises a functional group suitable for coupling directly or indirectly with the fumagillin analog.

In another aspect, biocompatible biodegradable conjugates are described which comprise at least one fumagillin analog of the formula II conjugated to a water soluble polyal

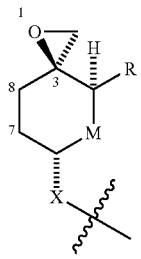

wherein

X is O, $S(=O)_q$, optionally substituted $CH_2$, or optionally substituted NH;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, $C_2$-heterocyclic-$C_1$-$C_6$ alkyl, $C_2$-heterocyclic-$C_2$-$C_6$ alkenyl, $C_1$-$C_6$ alkyl, $C_2$-$C_6$ alkenyl, $C_2$-heterocyclic-$C_1$-$C_6$-alkenyl-COO—$C_1$-$C_6$ alkyl, $C_2$-heterocyclic-$C_1$-$C_6$ alkyl-COO—$C_1$-$C_6$-alkyl, $C_1$-$C_6$ alkyl=N—O—$C_1$-$C_6$ alkyl-aryl, $C(O)C_1$-$C_6$ alkyl, CN, or halogen;

M is O, or

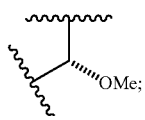

q is 0, 1, or 2;

wherein the fumagillin core structure can be optionally substituted at C-7 and C-8, independently, with $C_1$-$C_6$ alkyl, $C_2$-$C_6$ alkenyl, $C_2$-$C_6$ alkynyl, OH, ketone, or alkoxy;

wherein the fumagillin analog is conjugated by covalent attachment of X to a free hydroxyl of the polyal through a spacer moiety of the Formula III

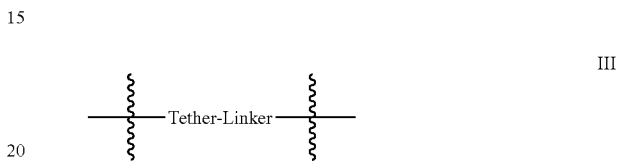

wherein Tether is an organic moiety with a molecular weight between about null and about 1000 covalently attached to both the X of Formula II and to Linker;

wherein Linker is an organic moiety covalently attached to both Tether and to a free hydroxyl of the polyal, having a molecular weight between about null and about 1000; and wherein the spacer moiety of Formula III comprises one or more labile bonds capable of enzymatic or chemical cleavage, so as to provide a fumagillin analog conjugate having either a higher water solubility than, a longer biological half-life than, or less neurotoxicity than, the unconjugated fumagillin analog.

In another aspect, biocompatible biodegradable polymer conjugates of the Formula IV are described:

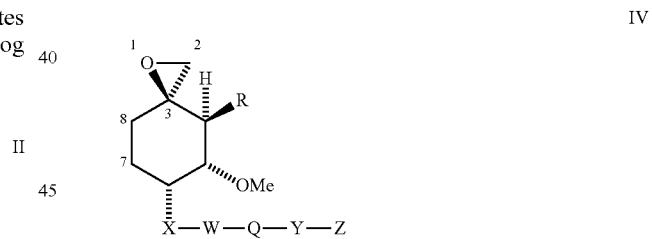

wherein

X is O, $S(=O)_q$, optionally substituted $CH_2$, or optionally substituted NH;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, $C_2$-heterocyclic-$C_1$-$C_6$ alkyl, $C_2$-heterocyclic-$C_2$-$C_6$ alkenyl, $C_1$-$C_6$ alkyl, $C_2$-$C_6$ alkenyl, $C_2$-heterocyclic-$C_1$-$C_6$-alkenyl-COO—$C_1$-$C_6$ alkyl, $C_2$-heterocyclic-$C_1$-$C_6$ alkyl-COO—$C_1$-$C_6$-alkyl, $C_1$-$C_6$ alkyl=N—O—$C_1$-$C_6$ alkyl-aryl, $C(O)C_1$-$C_6$ alkyl, CN, or halogen;

W is null, a bond, —C(O)—, —NH—, —$C_1$-$C_6$ alkyl-, —$C_2$-$C_6$ alkenyl-, —$C_2$-$C_6$ alkynyl-, —$C_1$-$C_6$ alkoxy-, -aryl-, -heteroaryl-, -cycloalkyl-, —C(O)bicycloalkylC(O)—, —$SO_2$-bicycloalkyl-, -heterocycloalkyl-, -heterobicycloalkyl-, —C(O)C_1$-$C_6$ alkyl heteroaryl-O—, —C(O)—$C_1$-$C_6$-alkenyl-aryl-O—N($C_1$-$C_6$ alkyl)$_2$-, —C(O)-heterocycloalkyl-$C_1$-$C_6$ alkyl-O—, —C(O)-heterocycloalkyl-$C_1$-$C_6$ alkyl-COO—, —C(O)-heterobicycloalkyl-$C_1$-$C_6$ alkyl- COO—, —C(O)-heterobicycloalkyl-$C_1$-$C_6$ alkyl-C(O)—, —C(O)NH($C_1$-$C_6$ alkyl)heteroaryl(O)—, —C(O)NH($C_1$-$C_6$ alkyl)aryl(O)—, —C(O)$C_1$-$C_6$ alkylaryl-, —NHC(O)$C_1$-$C_6$-alkylaryl-, —C(O)$C_1$-$C_6$-alkenyl-aryl-O—NH($C_1$-$C_6$-alkyl)-, —C(O)NH($C_1$-$C_6$ alkyl)cycloalkylCOO—, —C(O)cycloalkyl $C_1$-$C_6$ alkyl NH—, —NHC(O)$C_1$-$C_6$ alkyl-, —NHC(O)NH$C_1$-$C_6$ alkyl-, —$SO_2$NH—, —$SO_2$NH$C_1$-$C_6$ alkyl-, —$SO_2$N($C_1$-$C_6$ alkyl)$_2$-, —NH$SO_2$$C_1$-$C_6$ alkyl, —$CO_2$$C_1$-$C_6$ alkyl-, —CONH$C_1$-$C_6$ alkyl-, —CON($C_1$-$C_6$ alkyl)-, —$C_1$-$C_6$ alkyl aryl-O—$C_1$-$C_6$ alkyl N($C_1$-$C_6$ alkyl)$_2$-, —C(O)NHC(O)$C_1$-$C_6$ alkyl S $C_0$-$C_6$ alkyl aryl-, —$C_1$-$C_6$ alkyl NH—$SO_2$-heterocyclo-$C_1$-$C_6$ alkyl-O—, —C(O)NHC(O)$C_1$-$C_6$ alkyl S $C_0$-$C_6$ alkylNH—, —C(O)NH—$C_1$-$C_6$ alkyl-aryl-, —C(O)heterocycloalkyl-, —C(O)—$C_1$-$C_6$-alkyl-5-aryl-, —C(O)heterobicycloalkyl-, —C(O)—NH—C(O)—$C_1$-$C_6$ alkyl-, or —C(O)—NH—C(O)—$C_0$-$C_6$ alkyl-5-aryl-, each optionally substituted;

Q is null, —NH—, -amino acid-, —NH-amino acid-, —($C_1$-$C_6$ alkyl COO)—, —(OOC$C_1$-$C_6$ alkyl COO)—, —($C_1$-$C_6$ alkyl-O-amino acid)-, or —($C_1$-$C_6$ alkyl-O)—;

Y is null, an oxalic, malonic, succinic, glutaric, adipic, pimelic, suberic, azelaic, sebacic, phthalic, isophthalic, terephthalic, diglycolic acid, oxaglutaric, tartaric, glutamic, fumaric, or aspartic moiety, including amide, imide, or cyclic-imide derivatives of each thereof, and each optionally substituted; and Z is a polyal with the structure:

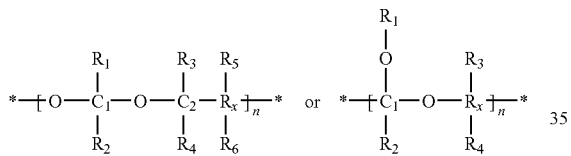

wherein for each occurrence of the n bracketed structure, either one of $R_1$ and $R_2$ is hydrogen, and the other is a biocompatible group and includes a carbon atom covalently attached to $C_1$ or each occurrence of $R_1$ and $R_2$ is a biocompatible group and includes a carbon atom covalently attached to $C_1$;

$R_x$ includes a carbon atom covalently attached to $C_2$;

n is an integer;

each occurrence of $R_3$, $R_4$, $R_5$, and $R_6$ is a biocompatible group and is independently hydrogen or an organic moiety; and for each occurrence of the bracketed structure n, at least one of $R_1$, $R_2$, $R_3$, $R_4$, $R_5$, and $R_6$ comprises a functional group suitable for coupling with W, Y, or Q.

In another aspect, compounds of the Formula V are described:

V

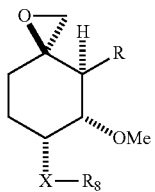

wherein,

X is O, S(=O)$_q$, optionally substituted $CH_2$, or optionally substituted NH;

q is 0, 1, or 2;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, $C_2$-heterocyclic-$C_1$-$C_6$ alkyl, $C_2$-heterocyclic-$C_2$-$C_6$ alkenyl, $C_1$-$C_6$ alkyl, $C_2$-$C_6$ alkenyl, $C_2$-heterocyclic-$C_1$-$C_6$-alkenyl-COO—$C_1$-$C_6$ alkyl, $C_2$-heterocyclic-$C_1$-$C_6$ alkyl-COO—$C_1$-$C_6$-alkyl, $C_1$-$C_6$ alkyl=N—O—$C_1$-$C_6$ alkyl-aryl, C(O)$C_1$-$C_6$ alkyl, CN, or halogen;

$R_8$ is selected from the group consisting of VI, VII, VIII, IX, X, XI, XII, and XIIA whose formulas are represented below:

VI

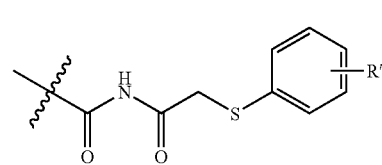

R' is —$CO_2$H, optionally substituted —$NH_2$, or —N cyclic imide, NHC(O)($C_1$-$C_6$ alkyl)-C(O)R", R' is meta or para in relation to the —S— atom; and R" is —OH, —O—$C_1$-$C_6$ alkyl, or —$NH_2$ optionally acylated through the carboxyl group of an amino acid;

VII

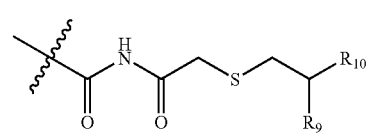

wherein $R_9$ is H or C(O)$R_{11}$;

$R_{10}$ is —$NH_2$, —NHCH($C_1$-$C_6$ alkyl)-, —NHC(O)($C_1$-$C_6$ alkyl), N-cyclized imide; —NH acylated through the carboxyl group of an amino acid, wherein the nitrogen of the amino group of the amino acid is optionally protected; and $R_{11}$ is OH, O$C_1$-$C_6$ alkyl, or optionally substituted —$NH_2$;

VIII

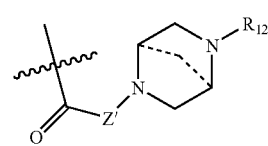

wherein $R_{12}$ is H, $C_1$-$C_6$ alkyl, —($C_1$-$C_6$)—COOH, —($C_1$-$C_6$)—C(O)O—($C_1$-$C_6$), —$CH_2CH_2O$—$R_{13}$, —C(O)($C_1$-$C_6$-alkyl), or an amino acid attached through the carboxyl group of the amino acid;

$R_{13}$ is —H or an amino acid attached through the carboxyl group of the amino acid, wherein the nitrogen of the amino acid is optionally protected, C(O)($C_1$-$C_6$ alkyl)-COR";

R" is OH, —O$C_1$-$C_6$ alkyl, or —$NH_2$ optionally acylated through the carboxyl group of an amino acid;

[------] represents an optional methylene bridge (—$CH_2$—) between carbons 2 and 5 of the piperazine moiety; and Z' is a bond, —$C_1$-$C_6$ alkyl, —NHC(O)—, or —NH$SO_2$—;

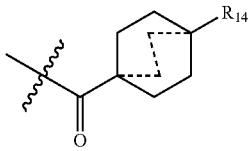

IX wherein $R_{14}$ is —H, —CO$_2$H, —CO$_2$(C$_1$-C$_6$ alkyl), —C(O)NH—C$_1$-C$_6$ alkyl-OH, wherein the O of —C(O)NH—C$_1$-C$_6$ alkyl-OH is optionally acylated with the carboxyl group of an amino acid; optionally substituted —NH$_2$, C$_1$-C$_6$-alkyl-NH$_2$, wherein the NH$_2$ is optionally substituted; and

[-------] represents an optional ethylene bridge (—CH$_2$CH$_2$—) between carbons 1 and 4 of the cyclohexane moiety;

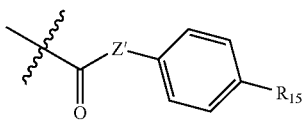

Z' is a bond, —CH$_2$—, —CH$_2$—S—, —CH$_2$CH$_2$—, —C(H)(Me)-, —NHCH$_2$—, —NHCH(CH$_3$)—, or —NHCH$_2$CH$_2$—;

$R_{15}$ is H, optionally substituted —NH$_2$, —NHC(O)(C$_1$-C$_6$-alkyl), —N cyclized imide optionally containing a heteroatom within the cyclic structure, —NHC(O)CH$_2$OCH$_2$C(O)OH, NHC(O)CH(C$_1$-C$_6$ alkyl)-N cyclized imide, —NHC(O)CH(R")NHC(O)—(C$_1$-C$_6$ alkyl)-C(O)OH, —NHC(O)—(C$_1$-C$_6$ alkyl)-C(O)OH, —C(O)O(C$_1$-C$_6$ alkyl), —C(O)N(H)(C$_1$-C$_6$ alkyl)-OH, or NO$_2$; and R" is —H, or —C$_1$-C$_6$ alkyl;

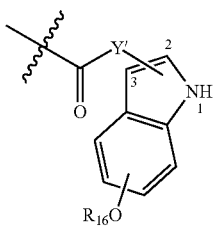

XI wherein Y' is C$_1$-C$_3$ alkyl, or NH—C$_1$-C$_3$ alkyl and is attached to positions 1, 2, or 3 of the indole; and $R_{16}$ is H, C$_1$-C$_6$ alkyl, —CH$_2$COOH, or —CH$_2$CH$_2$OH, wherein the O of —CH$_2$CH$_2$OH can be optionally acylated with an amino acid;

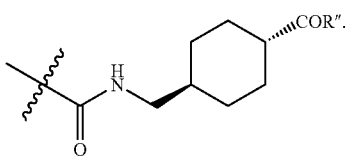

XII wherein R" is —OH, —OC$_1$-C$_6$ alkyl, or —NH$_2$ optionally acylated through the carboxyl group of an amino acid; and

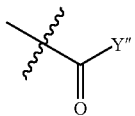

XIIA wherein Y" is C(O)N(CH$_3$)(OCH$_3$), C(O)OCH$_3$, CH$_2$Cl, or NHC(O)CH$_2$Cl.

Pharmaceutical compositions comprising an effective amount of a fumagillin analog conjugate and a pharmaceutically acceptable carrier are described.

Pharmaceutical compositions comprising an effective amount of a fumagillin analog and a pharmaceutically acceptable carrier are described. Also, fumagillin analogs are provided as a pharmaceutically acceptable prodrug, hydrated salt, such as a pharmaceutically acceptable salt, or mixtures thereof.

In another aspect, methods for treating cancer, or treating an angiogenic disease, comprising the administration of an effective amount of a fumagillin analog conjugate are described.

In another aspect, methods for treating cancer, or treating an angiogenic disease, comprising the administration of an effective amount of a fumagillin analog are described.

DETAILED DESCRIPTION OF THE INVENTION

The following definitions are used in connection with the fumagillin analog conjugates and the fumagillin analogs described herein:

"Alkyl" refers to a hydrocarbon chain that may be a straight chain or branched chain, containing the indicated number of carbon atoms. For example, C$_1$-C$_6$ indicates that the group may have from 1 to 6 (inclusive) carbon atoms in it.

"Aryl" refers to cyclic aromatic carbon ring systems containing from 6 to 18 carbons. Examples of an aryl group include, but are not limited to, phenyl, naphthyl, anthracenyl, tetracenyl, and phenanthrenyl. An aryl group can be unsubstituted or substituted with one or more of the following groups: H, halogen, CN, OH, aryl, arylalkyl, heteroaryl, heteroarylalkyl, C$_{1-6}$ alkyl, C$_{2-6}$ alkenyl, C$_{2-6}$ alkynyl, C$_{1-3}$ fluorinated-alkyl, C$_{3-6}$ cycloalkyl, C$_{3-6}$cycloalkyl-C$_{1-3}$alkyl, NO$_2$, NH$_2$, NHC$_{1-6}$ alkyl, N(C$_{1-6}$ alkyl)$_2$, NHC$_{3-6}$ cycloalkyl, N(C$_{3-6}$ cycloalkyl)$_2$, NHC(O)C$_{1-6}$ alkyl, NHC(O)C$_{3-6}$ cycloalkyl, NHC(O)NHC$_{1-6}$ alkyl, NHC(O)NHC$_{3-6}$ cycloalkyl, SO$_2$NH$_2$, SO$_2$NHC$_{1-6}$ alkyl, SO$_2$NHC$_{3-6}$ cycloalkyl, SO$_2$N(C$_{1-6}$ alkyl)$_2$, SO$_2$N(C$_{3-6}$ cycloalkyl)$_2$, NHSO$_2$C$_{1-6}$ alkyl, NHSO$_2$C$_{3-6}$ cycloalkyl, CO$_2$C$_{1-6}$ alkyl, CO$_2$C$_{3-6}$ cycloalkyl, CONHC$_{1-6}$ alkyl, CONHC$_{3-6}$ cycloalkyl, CON(C$_{1-6}$ alkyl)$_2$, CON(C$_{3-6}$ cycloalkyl)$_2$OH, OC$_{1-3}$ alkyl, C$_{1-3}$ fluorinated-alkyl, OC$_{3-6}$ cycloalkyl, OC$_{3-6}$ cycloalkyl-C$_{1-3}$ alkyl, SH, SO$_x$C$_{1-3}$ alkyl, C$_{3-6}$ cycloalkyl, or SO$_x$C$_{3-6}$ cycloalkyl-C$_{1-3}$ alkyl, where x is 0, 1, or 2.

"Heteroaryl" refers to mono and bicyclic aromatic groups of 4 to 10 atoms containing at least one heteroatom. Heteroatom as used in the term heteroaryl refers to oxygen, sulfur and nitrogen. Examples of monocyclic heteroaryls include, but are not limited to, oxazinyl, thiazinyl, diazinyl, triazinyl, tetrazinyl, imidazolyl, tetrazolyl, isoxazolyl, furanyl, furazanyl, oxazolyl, thiazolyl, thiophenyl, pyrazolyl, triazolyl, and pyrimidinyl. Examples of bicyclic heteroaryls include but are not limited to, benzimidazolyl, indolyl, isoquinolinyl, indazolyl, quinolinyl, quinazolinyl, purinyl, benzisoxazolyl, benzoxazolyl, benzthiazolyl, benzodiazolyl, benzotriazolyl, isoindolyl and indazolyl. A heteroaryl group can be unsubstituted or substituted with one or more of the following groups: H, halogen, CN, OH, aryl, arylalkyl, heteroaryl, heteroarylalkyl, $C_{1-6}$ alkyl, $C_{2-6}$ alkenyl, $C_{2-6}$ alkynyl, $C_{1-3}$ fluorinated-alkyl, $C_{3-6}$ cycloalkyl, $C_{3-6}$cycloalkyl-$C_{1-3}$alkyl, $NO_2$, $NH_2$, $NHC_{1-6}$ alkyl, $N(C_{1-6}$ alkyl$)_2$, $NHC_{3-6}$ cycloalkyl, $N(C_{3-6}$ cycloalkyl$)_2$, $NHC(O)C_{1-6}$ alkyl, $NHC(O)C_{3-6}$ cycloalkyl, $NHC(O)NHC_{1-6}$ alkyl, $NHC(O)NHC_{3-6}$ cycloalkyl, $SO_2NH_2$, $SO_2NHC_{1-6}$ alkyl, $SO_2NHC_{3-6}$ cycloalkyl, $SO_2N(C_{1-6}$ alkyl$)_2$, $SO_2N(C_{3-6}$ cycloalkyl$)_2$, $NHSO_2C_{1-6}$ alkyl, $NHSO_2C_{3-6}$ cycloalkyl, $CO_2C_{1-6}$ alkyl, $CO_2C_{3-6}$ cycloalkyl, $CONHC_{1-6}$ alkyl, $CONHC_{3-6}$ cycloalkyl, $CON(C_{1-6}$ alkyl$)_2$, $CON(C_{3-6}$ cycloalkyl$)_2$OH, $OC_{1-3}$ alkyl, $C_{1-3}$ fluorinated-alkyl, $OC_{3-6}$ cycloalkyl, $OC_{3-6}$ cycloalkyl-$C_{1-3}$ alkyl, SH, $SO_xC_{1-3}$ alkyl, $C_{3-6}$ cycloalkyl, or $SO_xC_{3-6}$ cycloalkyl-$C_{1-3}$ alkyl, where x is 0, 1, or 2.

"Arylalkyl" refers to an aryl group with at least one alkyl substitution. Examples of arylalkyl include, but are not limited to, toluenyl, phenylethyl, xylenyl, phenylbutyl, phenylpentyl, and ethylnaphthyl. An arylalkyl group can be unsubstituted or substituted with one or more of the following groups: H, halogen, CN, OH, aryl, arylalkyl, heteroaryl, heteroarylalkyl, $C_{1-6}$ alkyl, $C_{2-6}$ alkenyl, $C_{2-6}$ alkynyl, $C_{1-3}$ fluorinated-alkyl, $C_{3-6}$ cycloalkyl, $C_{3-6}$cycloalkyl-$C_{1-3}$alkyl, $NO_2$, $NH_2$, $NHC_{1-6}$ alkyl, $N(C_{1-6}$ alkyl$)_2$, $NHC_{3-6}$ cycloalkyl, $N(C_{3-6}$ cycloalkyl$)_2$, $NHC(O)C_{1-6}$ alkyl, $NHC(O)C_{3-6}$ cycloalkyl, $NHC(O)NHC_{1-6}$ alkyl, $NHC(O)NHC_{3-6}$ cycloalkyl, $SO_2NH_2$, $SO_2NHC_{1-6}$ alkyl, $SO_2NHC_{3-6}$ cycloalkyl, $SO_2N(C_{1-6}$ alkyl$)_2$, $SO_2N(C_{3-6}$ cycloalkyl$)_2$, $NHSO_2C_{1-6}$ alkyl, $NHSO_2C_{3-6}$ cycloalkyl, $CO_2C_{1-6}$ alkyl, $CO_2C_{3-6}$ cycloalkyl, $CONHC_{1-6}$ alkyl, $CONHC_{3-6}$ cycloalkyl, $CON(C_{1-6}$ alkyl$)_2$, $CON(C_{3-6}$ cycloalkyl$)_2$OH, $OC_{1-3}$ alkyl, $C_{1-3}$ fluorinated-alkyl, $OC_{3-6}$ cycloalkyl, $OC_{3-6}$ cycloalkyl-$C_{1-3}$ alkyl, SH, $SO_xC_{1-3}$ alkyl, $C_{3-6}$ cycloalkyl, or $SO_xC_{3-6}$ cycloalkyl-$C_{1-3}$ alkyl, where x is 0, 1, or 2.

"Heteroarylalkyl" refers to a heteroaryl group with at least one alkyl substitution. A heteroarylalkyl group can be unsubstituted or substituted with one or more of the following: H, halogen, CN, OH, aryl, arylalkyl, heteroaryl, heteroarylalkyl, $C_{1-6}$ alkyl, $C_{2-6}$ alkenyl, $C_{2-6}$ alkynyl, $C_{1-3}$ fluorinated-alkyl, $C_{3-6}$ cycloalkyl, $C_{3-6}$cycloalkyl-$C_{1-3}$alkyl, $NO_2$, $NH_2$, $NHC_{1-6}$ alkyl, $N(C_{1-6}$ alkyl$)_2$, $NHC_{3-6}$ cycloalkyl, $N(C_{3-6}$ cycloalkyl$)_2$, $NHC(O)C_{1-6}$ alkyl, $NHC(O)C_{3-6}$ cycloalkyl, $NHC(O)NHC_{1-6}$ alkyl, $NHC(O)NHC_{3-6}$ cycloalkyl, $SO_2NH_2$, $SO_2NHC_{1-6}$ alkyl, $SO_2NHC_{3-6}$ cycloalkyl, $SO_2N(C_{1-6}$ alkyl$)_2$, $SO_2N(C_{3-6}$ cycloalkyl$)_2$, $NHSO_2C_{1-6}$ alkyl, $NHSO_2C_{3-6}$ cycloalkyl, $CO_2C_{1-6}$ alkyl, $CO_2C_{3-6}$ cycloalkyl, $CONHC_{1-6}$ alkyl, $CONHC_{3-6}$ cycloalkyl, $CON(C_{1-6}$ alkyl$)_2$, $CON(C_{3-6}$ cycloalkyl$)_2$OH, $OC_{1-3}$ alkyl, $C_{1-3}$ fluorinated-alkyl, $OC_{3-6}$ cycloalkyl, $OC_{3-6}$ cycloalkyl-$C_{1-3}$ alkyl, SH, $SO_xC_{1-3}$ alkyl, $C_{3-6}$ cycloalkyl, or $SO_xC_{3-6}$ cycloalkyl-$C_{1-3}$ alkyl, where x is 0, 1, or 2.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, isopropyl, n-pentyl, isopentyl, neopentyl, and hexyl.

"$C_2$-$C_6$ alkenyl" refers to a straight or branched chain unsaturated hydrocarbon containing 2-6 carbon atoms and at least one double bond. Examples of a $C_2$-$C_6$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, and isohexene.

"$C_3$-$C_6$ alkenyl" refers to a straight or branched chain unsaturated hydrocarbon containing 3-6 carbon atoms and at least one double bond. Examples of a $C_3$-$C_6$ alkenyl group include, but are not limited to, propylene, 1-butylene, 2-butylene, isobutylene, sec-butylene, 1-pentene, 2-pentene, isopentene, 1-hexene, 2-hexene, 3-hexene, and isohexene.

"$C_1$-$C_6$ alkoxy" refers to a straight or branched chain saturated or unsaturated hydrocarbon containing 1-6 carbon atoms and at least one oxygen atom. Examples of a $C_1$-$C_6$-alkoxy include, but are not limited to, methoxy, ethoxy, isopropoxy, butoxy, n-pentoxy, isopentoxy, neopentoxy, and hexoxy.

"Cycloalkyl" refers to a cyclic saturated hydrocarbon. Examples of a cycloalkyl group include, but are not limited to, cyclopropane, cyclobutane, cyclopentane, cyclohexane, cycloheptane, and cyclooctane.

"$C_1$-$C_3$ fluorinated alkyl" refers to a saturated straight or branched chain hydrocarbon containing 1-3 carbon atoms that can be further substituted with other functional groups. Examples of a $C_1$-$C_3$ fluorinated alkyl are trifluoromethyl, 2,2,2-trifluoroethyl, and trifluoroacetyl.

"Halogen" refers to an atom of fluorine, chlorine, bromine, or iodine.

"Bicycloalkyl" refers to a saturated hydrocarbon two ring system sharing a pair of bridgehead carbons that can be further substituted with other functional groups. Examples of a bicycloalkyl include, but are not limited to, bicyclo[2.2.1]heptane (norbornane), bicyclo[4.3.2]undecane, bicyclo[4.1.0]heptane, bicyclo[4.4.0]decane (decalin), and bicyclo[2.2.2]octane.

"Heterobicycloalkyl" refers to a saturated hydrocarbon two ring system sharing two bridgehead atoms with at least one heteroatom. Heteroatom as used in the term heteroaryl refers to oxygen, sulfur, and nitrogen. Examples of heterobicycloalkyl include, but are not limited to, 2,5-diazabicyclo[2.2.1]heptanyl, 2-azabicyclo[2.2.1]heptanyl, 3-aza-bicyclo[4.1.0]heptanyl, and 1,4-dioxaspiro[4.4]nonyl.

"Cyclized imide" and "cyclic-imide" refer to either saturated or unsaturated cyclic or heterocyclic compounds that contain the imide functional group which consists of two carbonyl groups bound to a nitrogen atom. Cyclic-imides can be further substituted with other functional groups. Examples of a cyclic-imide include, but are not limited to, piperidyl-2,6-dione, morpholyl-3,5-dione, and pyrrolidyl-2,5-dione.

The term "optionally substituted NH" or "optionally substituted $NH_2$" when used herein means that one or more of the hydrogen atoms can be substituted for one of the following groups: $C_1$-$C_6$ alkyl, $C_2$-$C_6$ alkenyl, $C_2$-$C_6$ alkynyl, $C_1$-$C_3$ fluorinated alkyl, $SO_2NH_2$, $SO_2NHC_1$-$C_6$ alkyl, $SO_2N(C_1$-$C_6$ alkyl$)_2$, $C(O)OC_1$-$C_6$ alkyl, $CONHC_1$-$C_6$ alkyl, $CON(C_1$-$C_6$ alkyl$)_2$, —C(O)—CH(R")$NH_2$, wherein R" in this context is the side chain of any naturally occurring amino acid.

The phrase "one or more labile bonds capable of enzymatic or chemical hydrolysis" as used herein means a bond that is chemically reactive in the biological environment of the cell or blood or a bond known to be hydrolyzed by enzymes. Non-limiting examples of labile bonds capable of chemical or enzymatic hydrolysis are esters, amides, imides, thioethers, anhydrides, azides, carbamates, and carbonates.

The term "optionally substituted $CH_2$" when used herein means that one or both hydrogen atoms may be substituted with one or more of the following groups: OH, halogen, CN, $C_1$-$C_6$ alkyl, $C_2$-$C_6$ alkenyl, $C_2$-$C_6$ alkynyl, $C_1$-$C_6$ alkoxy, $C_1$-$C_3$ fluorinated alkyl, $NO_2$, $NH_2$, $NHC_1$-$C_6$ alkyl, $N(C_1$-$C_6$ alkyl$)_2$, $NHC(O)C_1$-$C_6$ alkyl, $NHC(O)NHC_1$-$C_6$ alkyl, $SO_2NH_2$, $SO_2NHC_1$-$C_6$ alkyl, $SO_2N(C_1$-$C_6$ alkyl$)_2$, $NHSO_2C_1$-$C_6$ alkyl, $C(O)OC_1$-$C_6$ alkyl, $CONHC_1$-$C_6$ alkyl, $CON(C_1$-$C_6$ alkyl$)_2$, $C_1$-$C_6$ alkyl, or both hydrogen atoms may be substituted and the substituted groups when taken together with the carbon to which they are attached, form a cycloalkyl or heterocycloalkyl, each optionally substituted with $C_1$-$C_6$ alkyl, $C_2$-$C_6$ alkenyl, $C_2$-$C_6$ alkynyl, $C_1$-$C_6$ alkoxy, $CO_2C_1$-$C_6$ alkyl, CN, OH, cycloalkyl, $CONH_2$, aryl, heteroaryl, COaryl, or trifluoroacetyl;

A "subject" is a mammal, e.g., a human, mouse, rat, guinea pig, dog, cat, horse, cow, pig, or non-human primate, such as a monkey, chimpanzee, baboon, or rhesus.

The term "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

An "effective amount" when used in connection with a fumagillin analog conjugate or a fumagillin analog is an amount effective for treating or preventing an angiogenic disease.

An "aminopeptidase" includes, but is not limited to, protein methionine aminopeptidase type 2.

The term "fumagillin core structure which demonstrates MetAP-2 inhibition" means any fumagillin core structure that inhibits the ability of MetAP-2 to remove $NH_2$-terminal methionines from proteins as described in Rodeschini et al., *J. Org. Chem.*, 69, 357-373, 2004 and Liu, et al., *Science* 282, 1324-1327, 1998. Nonlimiting examples of "fumagillin core structures" are disclosed in *J. Org. Chem.*, 69, 357, 2004; *J. Org. Chem.*, 70, 6870, 2005; European Patent Application 0 354 787; *J. Med. Chem.*, 49, 5645, 2006; *Bioorg. Med. Chem.*, 11, 5051, 2003; *Bioorg. Med. Chem.*, 14, 91, 2004; *Tet. Lett.* 40, 4797, 1999; WO99/61432; U.S. Pat. No. 6,603,812; U.S. Pat. No. 5,789,405; U.S. Pat. No. 5,767,293; U.S. Pat. No. 6,566,541; and U.S. Pat. No. 6,207,704.

The phrase "reduced toxicity" as used herein has its ordinary meaning as understood by persons of skill in the art. Merely by way of example, and by no means as a limitation on the meaning of the term, the administration of the fumagillin analog conjugate causes less side effects in open field tests with mice, as compared to the fumagillin analog alone.

The phrase "improved water solubility" has its ordinary meaning as understood by persons of skill in the art. Merely by way of example, and by no means as a limitation on the meaning of the term, the following description of the term is informative: an increased amount of a fumagillin analog will dissolve in water as a result of its covalent incorporation into a conjugate as compared to the amount of the unconjugated fumagillin analog that will dissolve in water alone.

The phrase "longer half-life" has its ordinary meaning as understood by persons of skill in the art. Merely by way of example, and by no means as a limitation on the meaning of the term, the following description of the term is informative: any appreciable increase in the length of time required to deactivate fumagillin conjugate either in vivo or in vitro as compared to the half-life of the fumagillin analog alone either in vivo or in vitro.

The term "polyal" means a polymer having at least one acetal or ketal oxygen atom in each monomer unit positioned within the main chain. Examples of polyals can be found in U.S. Pat. No. 5,811,510, U.S. Pat. No. 5,863,990, U.S. Pat. No. 5,958,398 and international application PCT/US2004/029130 which are incorporated herein by reference in their entirety. In certain embodiments, biodegradable biocompatible polymer carriers, useful for preparation of polymer conjugates described herein, are naturally occurring polysaccharides, glycopolysaccharides, and synthetic polymers of polyglycoside, polyacetal, polyamide, polyether, and polyester origin and products of their oxidation, functionalization, modification, cross-linking, and conjugation.

The term "fumagillin analog" as used herein includes a fumagillin core structure which demonstrates MetAP-2 inhibition (as defined above) along with a chemical spacer moiety that allows the fumagillin core structure to be covalently attached through the C-6 of the fumagillin core structure to an OH of the polyal. The chemical spacer moiety has a molecular weight range of between about 100 and about 1000.

As used herein, the term "angiogenic disease" includes a disease, disorder, or condition characterized or caused by aberrant or unwanted, e.g., stimulated or suppressed, formation of blood vessels (angiogenesis). Aberrant or unwanted angiogenesis may either cause a particular disease directly or exacerbate an existing pathological condition. Examples of angiogenic diseases include cancer, e.g., carcinomas and sarcomas, where progressive growth is dependent upon the continuous induction of angiogenesis by these tumor cells; pediatric disorders, e.g., angiofibroma, and hemophiliac joints; blood vessel diseases such as hemangiomas, and capillary proliferation within atherosclerotic plaques; disorders associated with surgery, e.g., hypertrophic scars, wound granulation and vascular adhesions; autoimmune diseases such as rheumatoid, immune and degenerative arthritis, where new vessels in the joint may destroy articular cartilage; and sclerodermaocular disorders and ocular disorders, e.g. diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, ocular tumors and trachoma, and other abnormal neovascularization conditions of the eye, where neovascularization may lead to blindness; and disorders affecting the skin, e.g., psoriasis and pyogenic granuloma, obesity, where adipogenesis is associated with neovascularization, and activated adipocytes produce multiple pro-angiogenic factors which can stimulate neovascularization during fat mass expansion; and endometriosis, where the endometriotic lesion is supported by the growth of new blood vessels, and the endometrium of patients with endometriosis shows enhanced endothelial cell proliferation.

The term angiogenic disease also includes diseases characterized by excessive or abnormal stimulation of endothelial cells, including but not limited to intestinal adhesions, Crohn's disease, atherosclerosis, scleroderma, and hypertrophic scars, i.e., keloids; diseases that have angiogenesis as a pathologic consequence such as cat scratch disease (*Rochele ninalia quintosa*) and ulcers (*Helicobacter pylori*). In addition, the angiogenesis inhibitor compounds of the present invention are useful as birth control agents (by virtue of their ability to inhibit the angiogenesis dependent ovulation and establishment of the placenta) and may also be used to reduce bleeding by administration to a subject prior to surgery.

The following abbreviations are used herein and have the indicated definitions: EDC (1-ethyl-3-(3-dimethylaminopropyl)carbodiimide hydrochloride), HOBt (N-hydroxybenzotriazole hydrate), CH₂Cl₂ (dichloromethane), MeCN (acetonitrile), MeOH (methanol), THF (tetrahydrofuran), DMAP (dimethylamino pyridine), EtOAc (ethyl acetate), PHF-GA (poly(1-hydroxymethylethylene hydroxymethyl-formal) conjugated to glutaric acid), DMF (dimethyl formamide), DME (dimethyl ether), LCMS (liquid chromatography-mass spectrometry).

The Fumagillin Analog Conjugates of Formulas I, II, and IV and the Fumagillin Analogs of Formula V.

In one aspect, biocompatible biodegradable conjugates are provided which comprise at least one fumagillin analog conjugated to a water soluble polyal, the conjugate having the structure of Formula I:

[fumagillin analog]$_m$-polyal     I wherein fumagillin analog is any fumagillin core structure which demonstrates MetAP-2 inhibition;

m is an integer from 1 to 40; and polyal is any polymer having at least one acetal oxygen atom or ketal oxygen atom in each monomer unit positioned within the main chain of the polymer.

Non-limiting examples of compounds capable of inhibiting MetAP-2 in removing NH₂-terminal methionines from proteins are represented by Formula IIA:

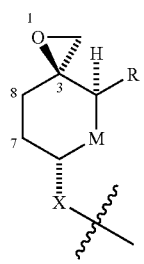

IIA wherein

X is O, S(=O)$_q$, optionally substituted CH₂, or optionally substituted NH;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C₂-heterocyclic-C₁-C₆ alkyl, C₂-heterocyclic-C₂-C₆ alkenyl, C₁-C₆ alkyl, C₂-C₆ alkenyl, C₂-heterocyclic-C₁-C₆-alkenyl-COO—C₁-C₆ alkyl, C₂-heterocyclic-C₁-C₆ alkyl-COO—C₁-C₆-alkyl, C₁-C₆ alkyl=N—O—C₁-C₆ alkyl-aryl, C(O)C₁-C₆ alkyl, CN, or halogen;

M is O, or

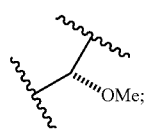

q is 0, 1, or 2; and the fumagillin core structure can be optionally substituted at C-7 and C-8, independently, with C₁-C₆ alkyl, C₂-C₆ alkenyl, C₂-C₆ alkynyl, OH, ketone, or alkoxy.

In some embodiments, the fumagillin analog of the conjugate has the core structure A:

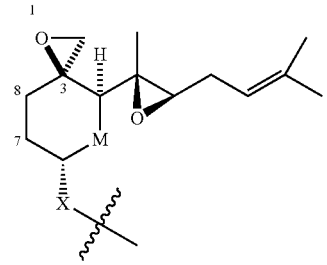

A wherein C-7 and C-8 are optionally substituted;

X is O, S(=O)$_q$, optionally substituted NH, or optionally substituted CH₂;

M is O, or

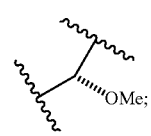

q is 0, 1, or 2; and the fumagillin analog is directly or indirectly attached to the polyal through X.

In other embodiments, the fumagillin analog of the conjugate has the core structure B:

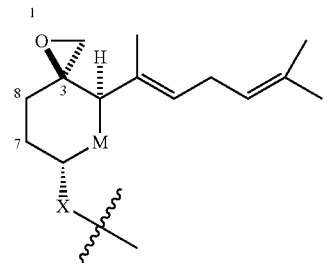

B wherein C-7 and C-8 are optionally substituted;

X is O, S(=O)$_q$, optionally substituted NH, or optionally substituted CH₂;

M is O, or

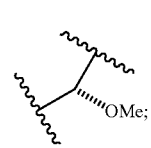

q is 0, 1, or 2; and the fumagillin analog is directly or indirectly attached to the polyal through X.

In still other embodiments, the fumagillin analog of the conjugate has the core structure C:

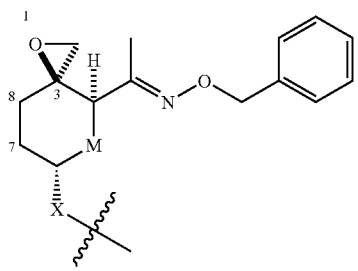

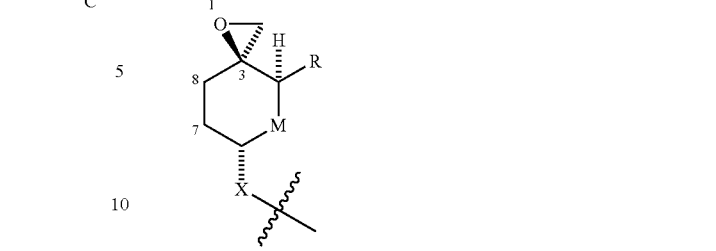

wherein C-7 and C-8 are optionally substituted;

X is O, S(=O)$_q$, optionally substituted NH, or optionally substituted CH$_2$;

M is O, or

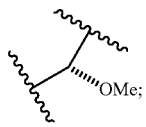

q is 0, 1, or 2; and the fumagillin analog is directly or indirectly attached to the polyal through X.

In some embodiments, the polyal has the structure

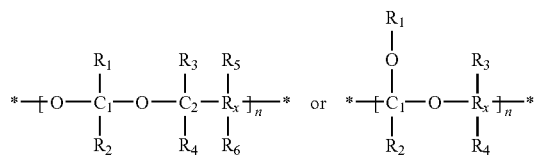

wherein for each occurrence of the n bracketed structure, either one of R$_1$ and R$_2$ is hydrogen, and the other is a biocompatible group and includes a carbon atom covalently attached to C$_1$ or each occurrence of R$_1$ and R$_2$ is a biocompatible group and includes a carbon atom covalently attached to C$_1$;

R$_x$ includes a carbon atom covalently attached to C$_2$;

n is an integer;

each occurrence of R$_3$, R$_4$, R$_5$, and R$_6$ is a biocompatible group and is independently hydrogen or an organic moiety; and for each occurrence of the bracketed structure n, at least one of R$_1$, R$_2$, R$_3$, R$_4$, R$_5$, and R$_6$ comprises a functional group suitable for coupling directly or indirectly with the fumagillin analog.

In another aspect, biocompatible biodegradable conjugates are provided which comprise at least one fumagillin analog of the formula II conjugated to a water soluble polyal wherein X is O, S(=O)$_q$, optionally substituted CH$_2$, or optionally substituted NH;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C$_2$-heterocyclic-C$_1$-C$_6$ alkyl, C$_2$-heterocyclic-C$_2$-C$_6$ alkenyl, C$_1$-C$_6$ alkyl, C$_2$-C$_6$ alkenyl, C$_2$-heterocyclic-C$_1$-C$_6$-alkenyl-COO—C$_1$-C$_6$ alkyl, C$_2$-heterocyclic-C$_1$-C$_6$ alkyl-COO—C$_1$-C$_6$-alkyl, C$_1$-C$_6$ alkyl=N—O—C$_1$-C$_6$ alkyl-aryl, C(O)C$_1$-C$_6$ alkyl, CN, or halogen;

M is O, or

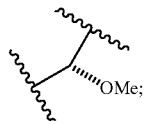

q is 0, 1, or 2;

wherein the fumagillin core structure can be optionally substituted at C-7 and C-8, independently, with C$_1$-C$_6$ alkyl, C$_2$-C$_6$ alkenyl, C$_2$-C$_6$ alkynyl, OH, ketone, or alkoxy;

wherein the fumagillin analog is conjugated by covalent attachment of X to a free hydroxyl of the polyal through a spacer moiety of the Formula III

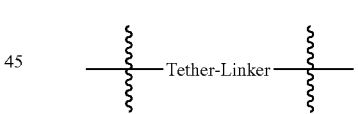

wherein Tether is an organic moiety with a molecular weight between about null and about 1000 covalently attached to both the X of Formula II and to Linker;

wherein Linker is an organic moiety covalently attached to both Tether and to a free hydroxyl of the polyal, having a molecular weight between about null and about 1000; and wherein the spacer moiety of Formula III comprises one or more labile bonds capable of enzymatic or chemical cleavage, so as to provide a fumagillin analog conjugate having either a higher water solubility than, a longer biological half-life than, or less neurotoxicity than, the unconjugated fumagillin analog.

Without being limited by any theory, the chemical composition of Linker can allow the fumagillin analog to be released from the polyal either through chemical or enzymatic cleavage.

In some embodiments, R is (2S,3R)-2-methyl-3-(3-methylbut-2-enyl)oxirane.

In some embodiments, R is 2-methylhepta-2,5-diene.

In other embodiments, R is (2R,3S)-2-isopentyl-3-methyloxirane.

In still other embodiments, R is (Z)-acetaldehyde O-benzyl oxime.

In some embodiments, Linker is an oxalic, malonic, succinic, glutaric, adipic, pimelic, suberic, azelaic, sebacic, phthalic, isophthalic, terephthalic, diglycolic acid, tartaric, glutamic, fumaric, or aspartic moiety, including amide, imide, or cyclic-imide derivatives of each thereof, and each optionally substituted.

In some embodiments, Linker is

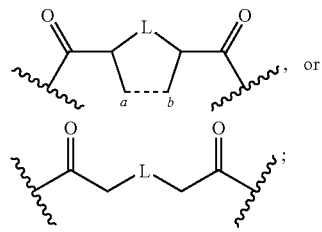, or

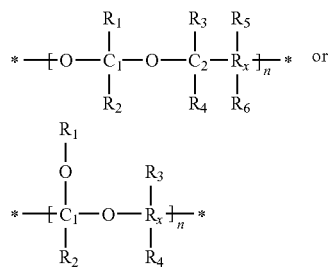;

wherein

L is a bond, optionally substituted —CH$_2$—, —CH(OH)—, optionally substituted —NH—, —O—, —S—, —SO—, —SO$_2$—, —C(CH$_3$)$_2$—, —CHO—, or —COCH$_2$—;

the dashed line between the carbon atoms at positions a and b represents a carbon-carbon single bond or a carbon-carbon double bond; and the methylene units adjacent to L can be optionally substituted.

In some embodiments, L is —CH$_2$—.
In other embodiments, L is —O—.
In other embodiments, the polyal has the structure:

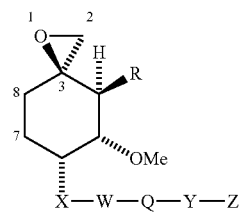

wherein for each occurrence of the n bracketed structure, either one of R$_1$ and R$_2$ is hydrogen, and the other is a biocompatible group and includes a carbon atom covalently attached to C$_1$ or each occurrence of R$_1$ and R$_2$ is a biocompatible group and includes a carbon atom covalently attached to C$_1$;

R$_x$ includes a carbon atom covalently attached to C$_2$;

n is an integer;

each occurrence of R$_3$, R$_4$, R$_5$, and R$_6$ is a biocompatible group and is independently hydrogen or an organic moiety; and for each occurrence of the bracketed structure n, at least one of R$_1$, R$_2$, R$_3$, R$_4$, R$_5$, and R$_6$ comprises a functional group suitable for coupling with Linker.

In another embodiment, the polyal is poly(1-hydroxymethylethylene hydroxymethyl-formal) (hereinafter abbreviated "PHF").

In another embodiment, the PHF has a molecular weight from about 40 kDa to about 100 kDa.

In another embodiment, PHF has a molecular weight from about 45 kDa to about 95 kDa.

In another embodiment, PHF has a molecular weight from about 50 kDa to about 90 kDa.

In another embodiment, PHF has a molecular weight from about 55 kDa to about 85 kDa.

In another embodiment, PHF has a molecular weight from about 60 kDa to about 80 kDa.

In another embodiment, PHF has a molecular weight from about 65 kDa to about 75 kDa.

In another embodiment, PHF has a molecular weight from about 68 kDa to about 72 kDa.

In another embodiment, PHF has a molecular weight of about 70 kDa.

In another aspect, biocompatible, biodegradable conjugates of the Formula IV are provided:

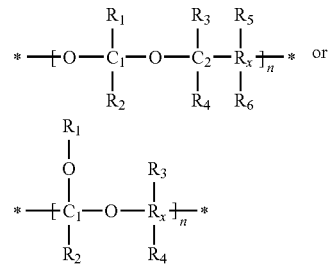

IV wherein R, X, W, Q, and Y are as defined above;
Z is a polyal with the structure:

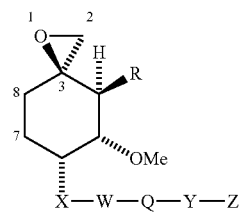

wherein for each occurrence of the n bracketed structure, one of R$_1$ and R$_2$ is hydrogen, and the other is a biocompatible group and includes a carbon atom covalently attached to C$_1$;

R$_x$ includes a carbon atom covalently attached to C$_2$;

n is an integer from 1 to 3000;

each occurrence of R$_3$, R$_4$, R$_5$, and R$_6$ is a biocompatible group and is independently hydrogen or a fumagillin analog; and for each occurrence of the bracketed structure n, at least one of R$_1$, R$_2$, R$_3$, R$_4$, R$_5$, and R$_6$ comprises a functional group suitable for coupling with W, Y, or Q.

In one embodiment, Z is PHF.
In one embodiment, the PHF has a molecular weight of about 70 kDa.
In one embodiment, X is O.
In one embodiment, X is NH.
In one embodiment, Y is —C(O)CH$_2$CH$_2$(O)C—.
In some embodiments, Y is —C(O)CH$_2$CH$_2$OCH$_2$CH$_2$(O)C—.
In some embodiments, Y is —C(O)CH$_2$CH$_2$CH$_2$(O)C—.

In some embodiments, R is (2S,3R)-2-methyl-3-(3-methylbut-2-enyl)oxirane.

In some embodiments, R is 2-methylhepta-2,5-diene.

In other embodiments, R is (2R,3S)-2-isopentyl-3-methyloxirane.

In still other embodiments, R is (Z)-acetaldehyde O-benzyl oxime.

In some embodiments, Q is —NH—.

In some embodiments, Q is amino acid.

In some embodiments, Q is NH-amino acid.

In some embodiments, W is —C(O)NH—$C_1$-$C_6$ alkyl-aryl-.

In some embodiments, W is —C(O)—NH—C(O)—$C_0$-$C_6$ alkyl-5-aryl-.

In some embodiments, W is —C(O)-heterocycloalkyl-$C_1$-$C_6$ alkyl-O—.

In another embodiment,

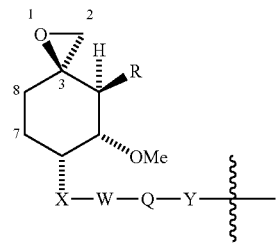

is selected from the group consisting of

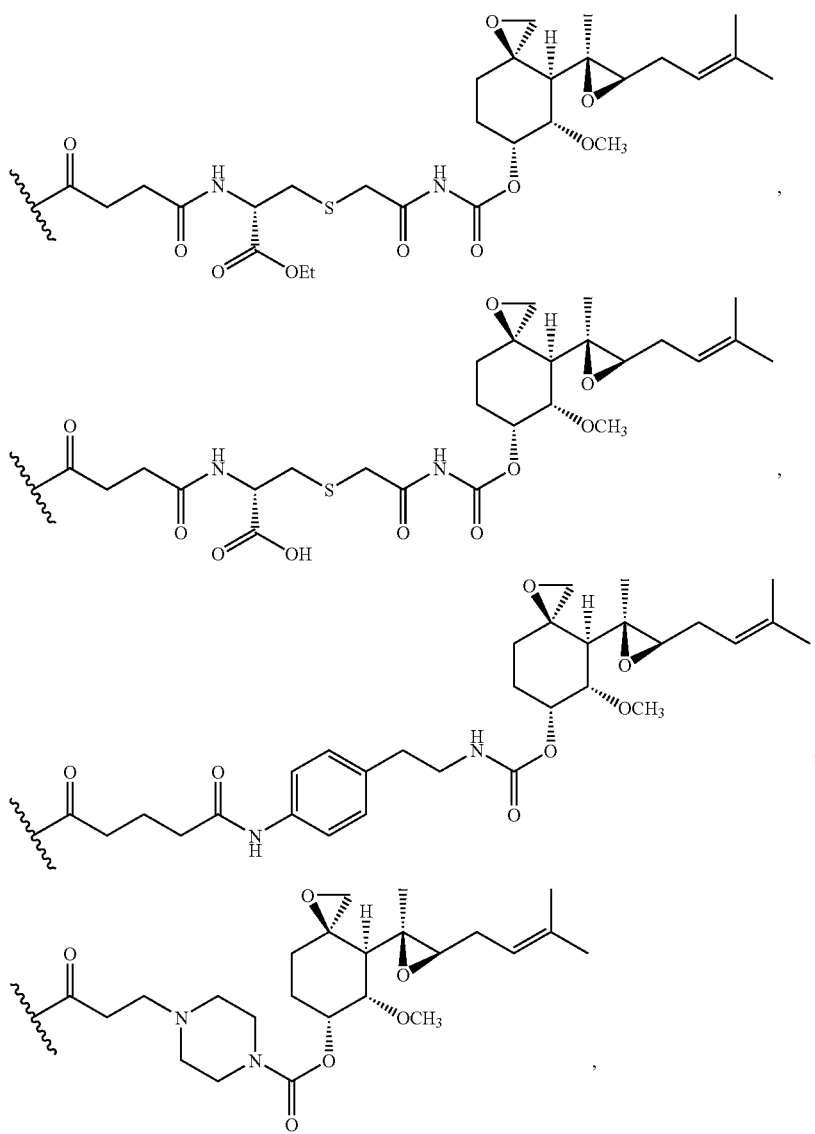

-continued
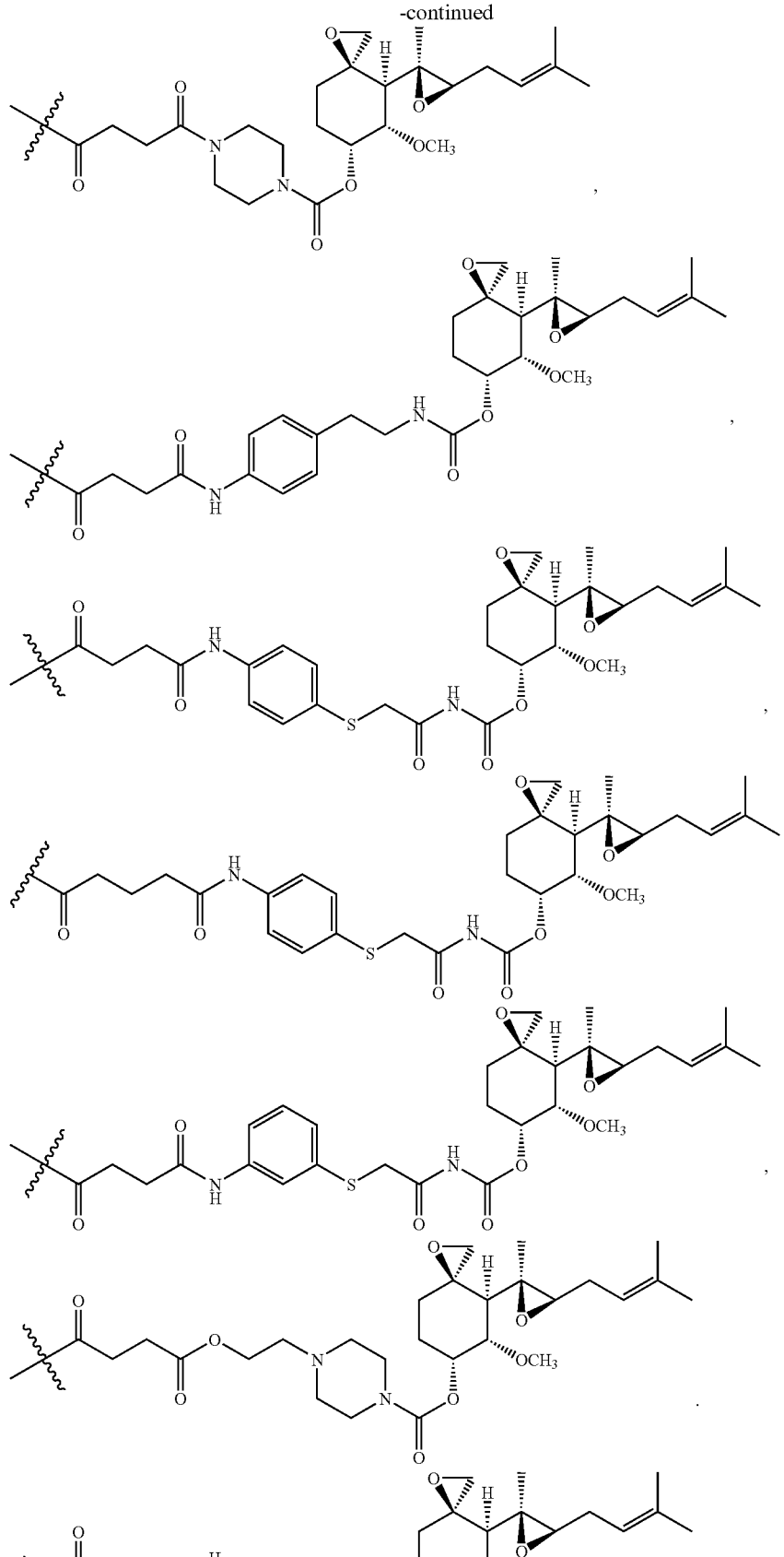

Illustrative Conjugates of Formula IV are listed below:
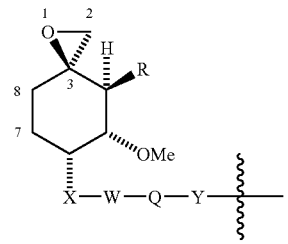
| Conjugate No. | Z | |
|---|---|---|
| 1 | PHF | 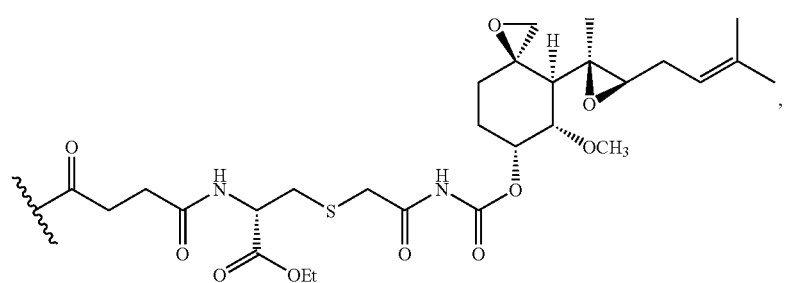 |
| 2 | PHF | 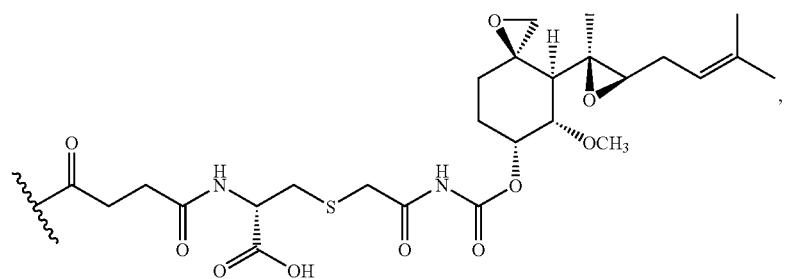 |
| 3 | PHF | 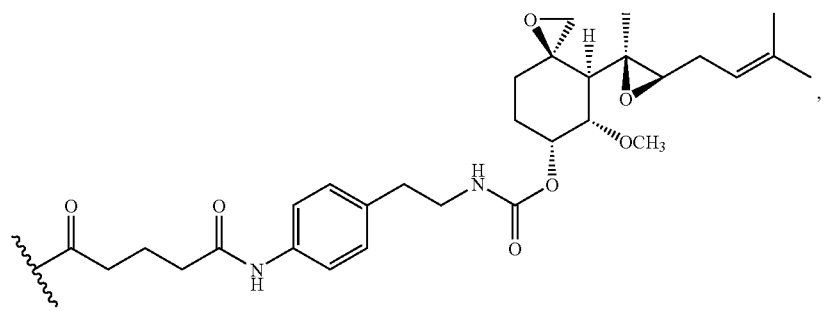 |
| 4 | PHF | 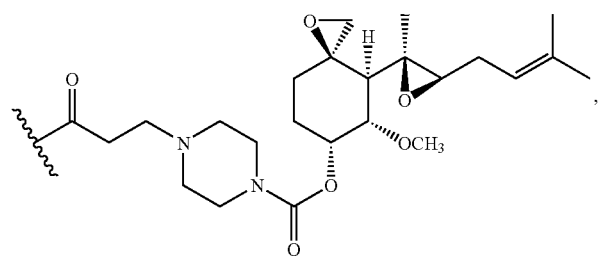 |

-continued
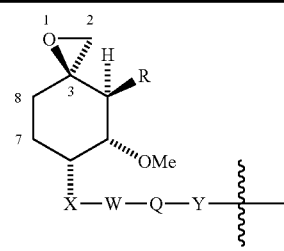
| Conjugate No. | Z | |
|---|---|---|
| 5 | PHF | 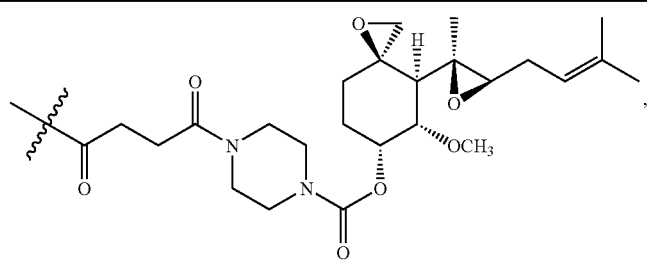 |
| 6 | PHF | 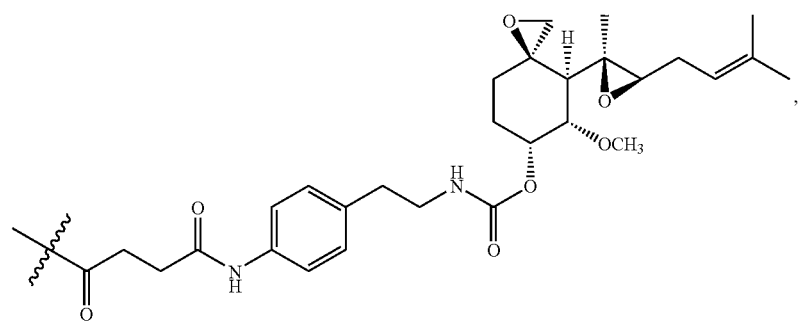 |
| 7 | PHF | 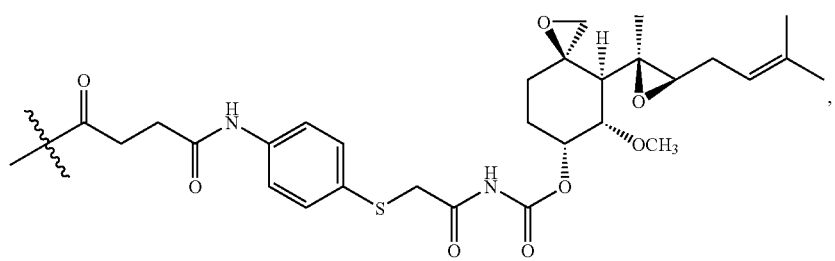 |
| 8 | PHF | 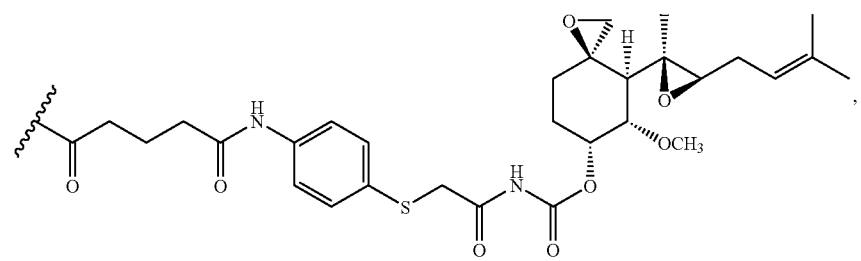 |
| 9 | PHF | 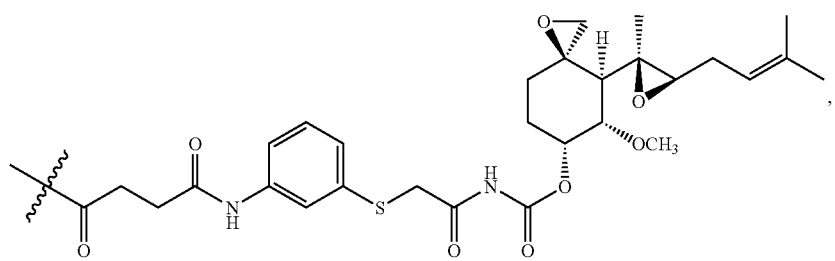 |

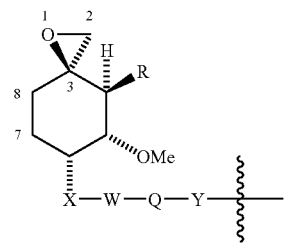
| Conjugate No. | Z |
|---|---|
| 10 | PHF 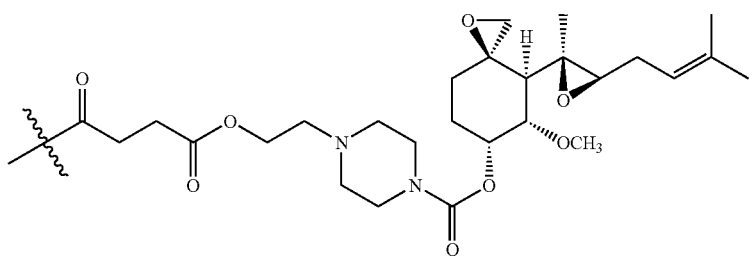 |
| 11 | PHF 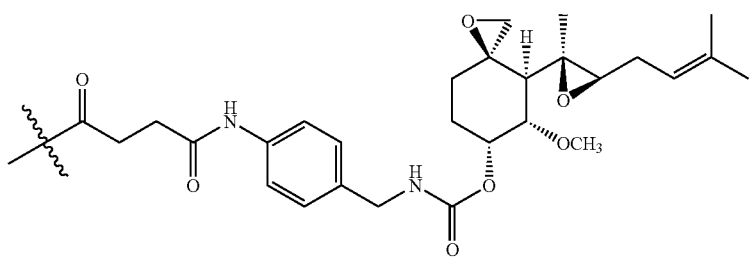 |
| 12 | PHF 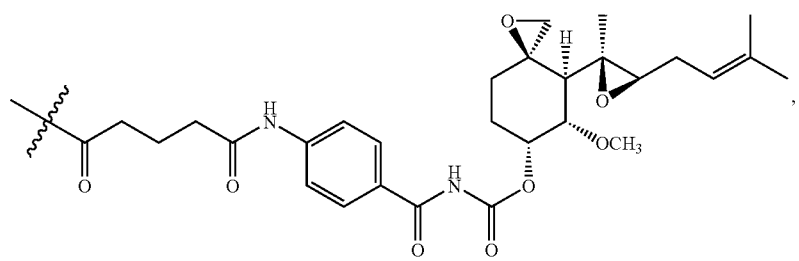 |
| 13 | PHF 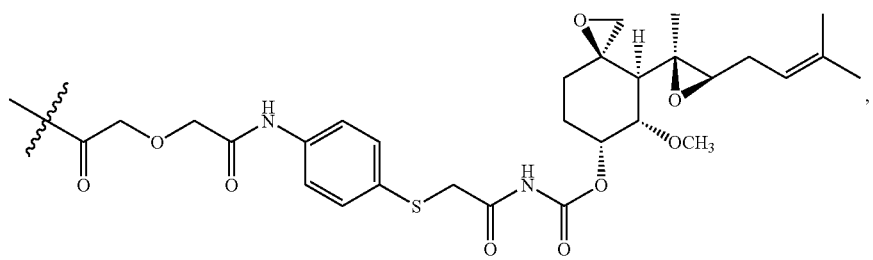 |
| 14 | PHF 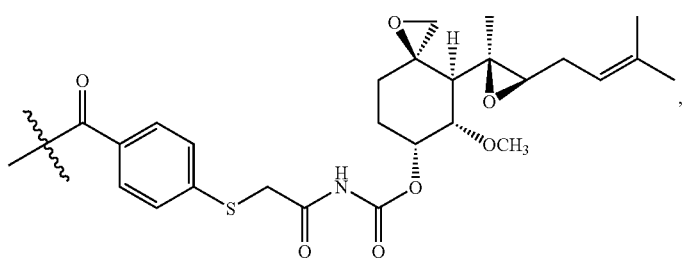 |

-continued
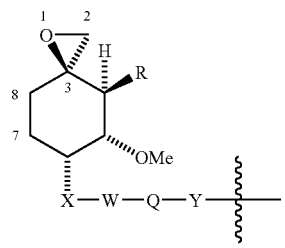
| Conjugate No. | Z |
|---|---|
| 15 | PHF |
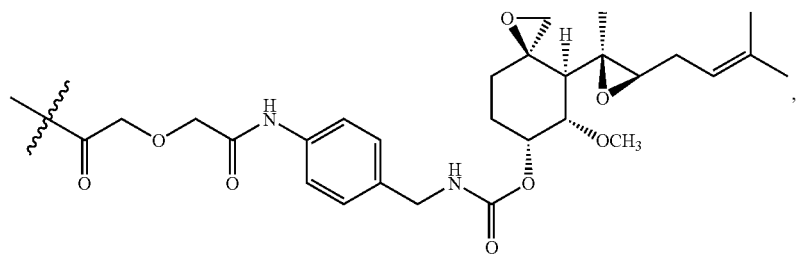
| | |
|---|---|
| 16 | PHF |
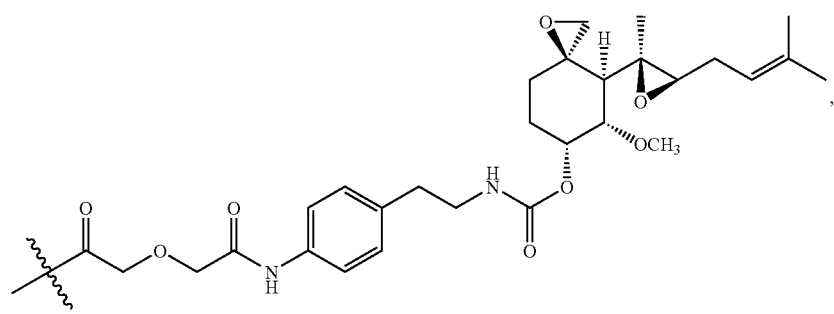
| | |
|---|---|
| 17 | PHF |
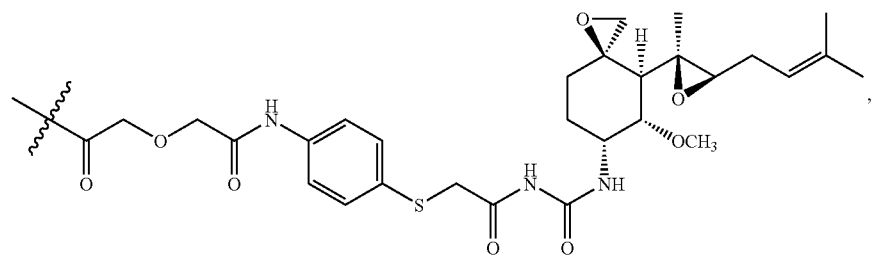
| | |
|---|---|
| 18 | PHF |
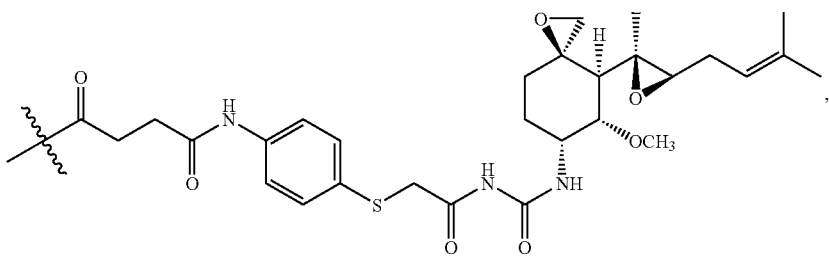
| | |
|---|---|
| 19 | PHF |
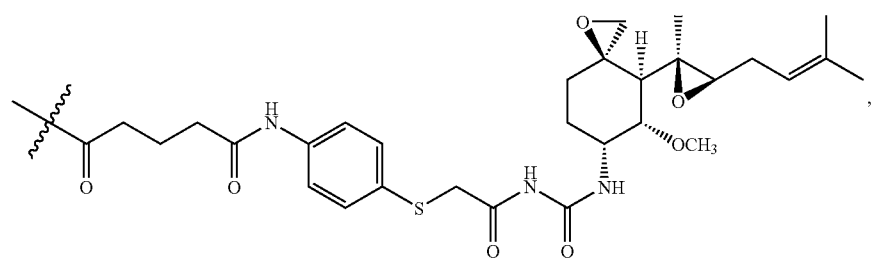

-continued
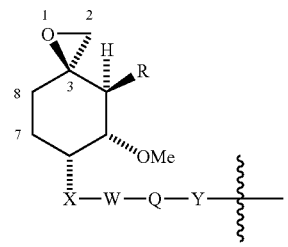
| Conjugate No. | Z | |
|---|---|---|
| 20 | PHF | 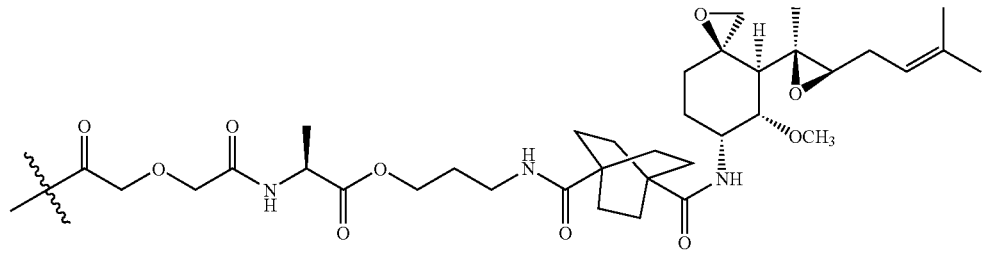 |
| 21 | PHF | 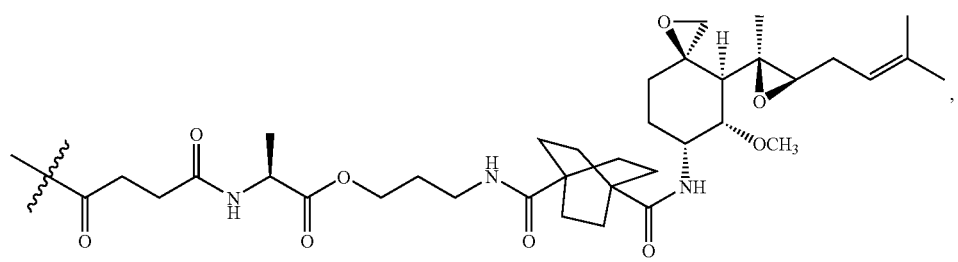 |
| 22 | PHF | 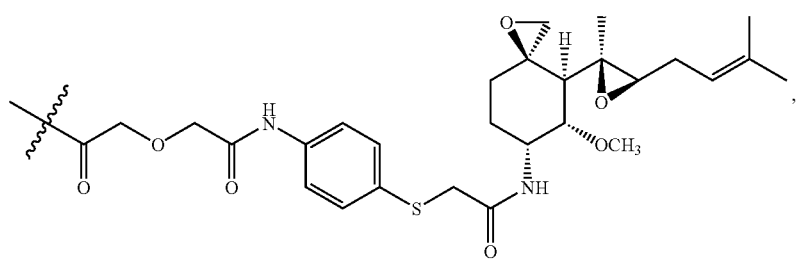 |
| 23 | PHF | 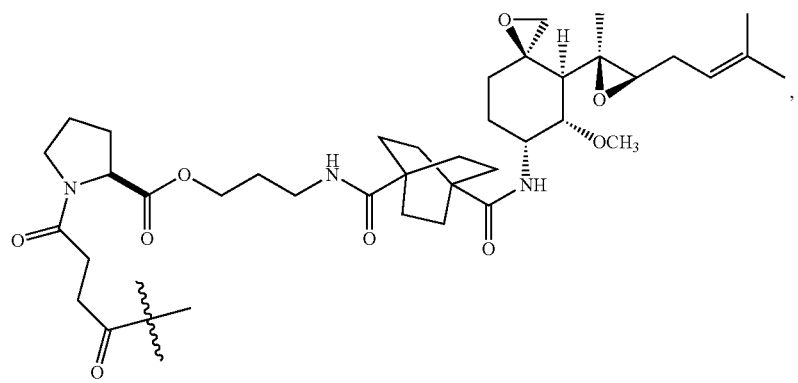 |

-continued
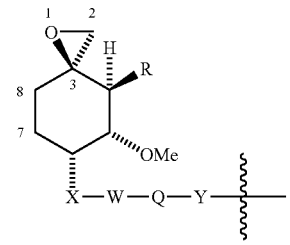
| Conjugate No. | Z | |
|---|---|---|
| 24 | PHF | 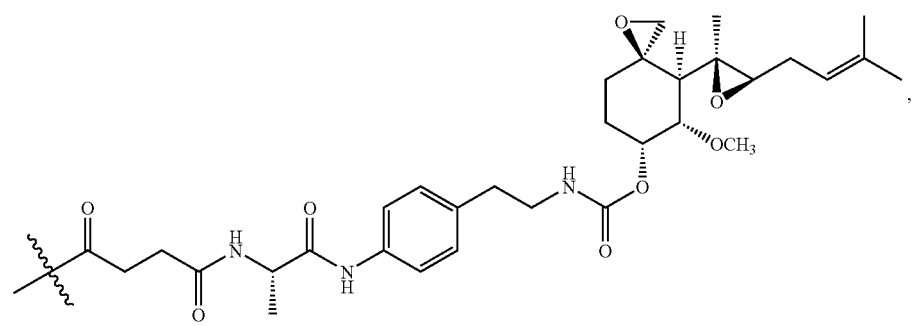 |
| 25 | PHF | 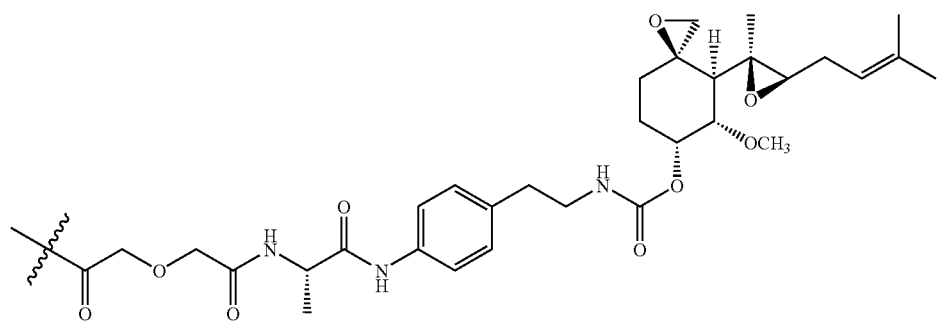 |
| 26 | PHF | 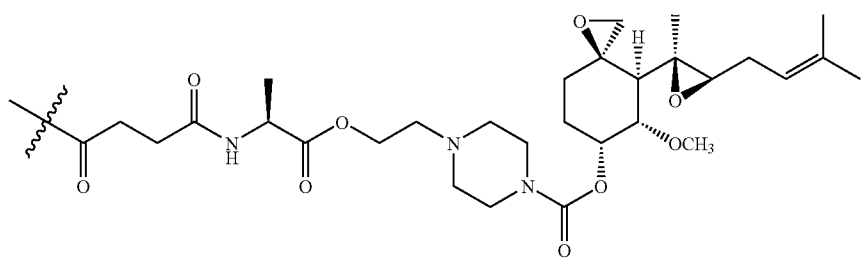 |
| 27 | PHF | 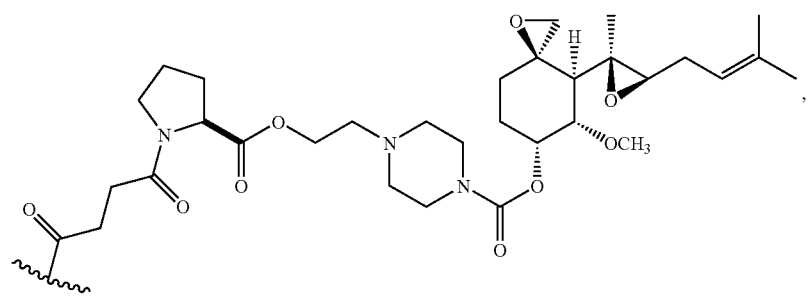 |

-continued
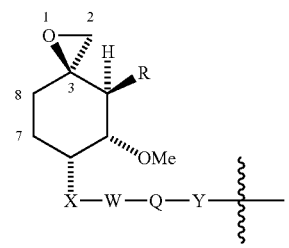
| Conjugate No. | Z | |
|---|---|---|
| 28 | PHF | 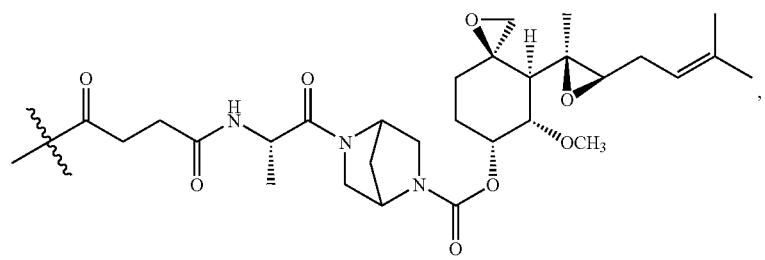 |
| 29 | PHF | 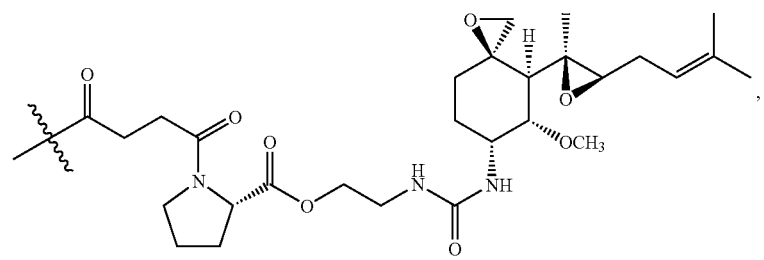 |
| 30 | PHF | 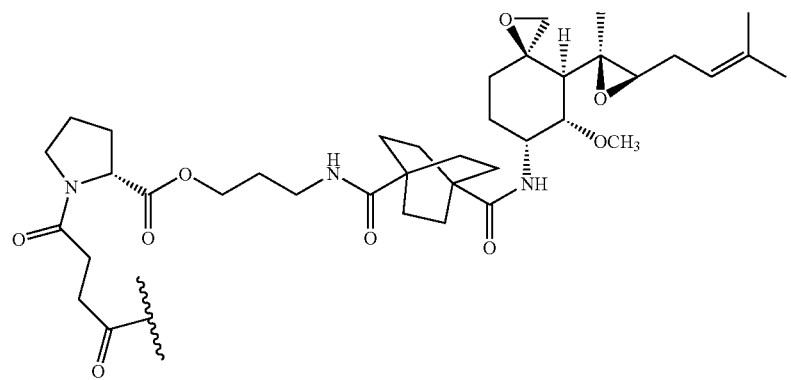 |
| 31 | PHF | 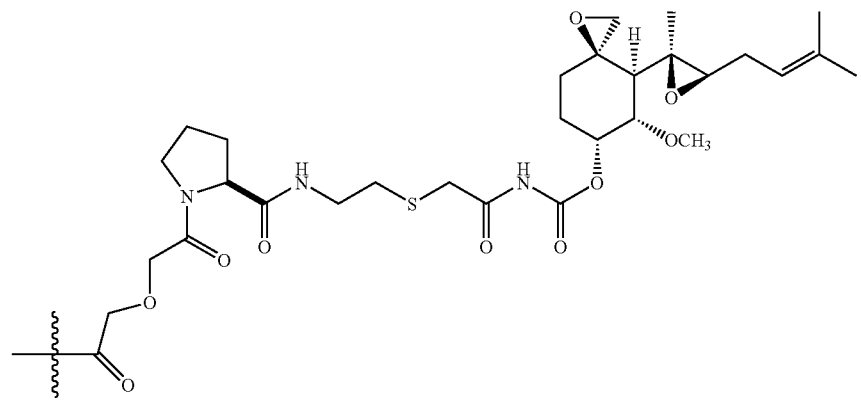 |

-continued
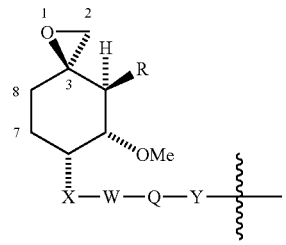
| Conjugate No. | Z |
|---|---|
| 32 | PHF |
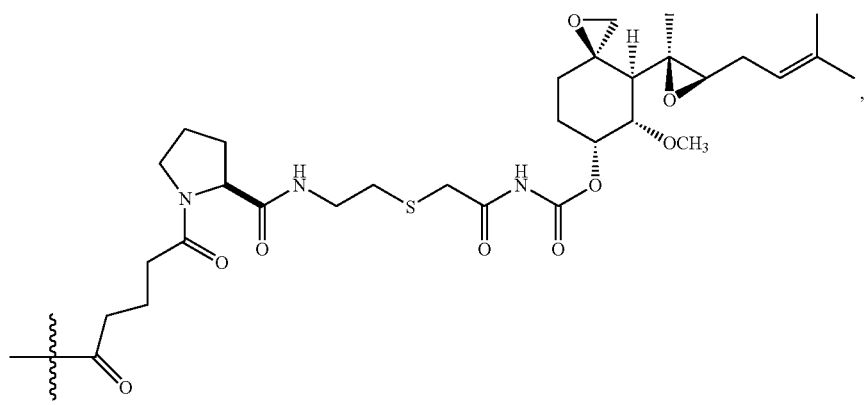
| 33 | PHF |
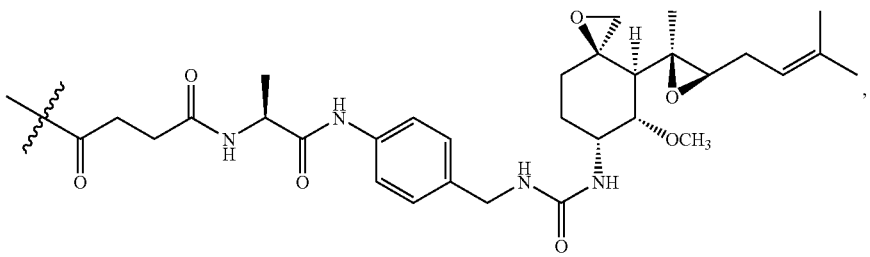
| 34 | PHF |
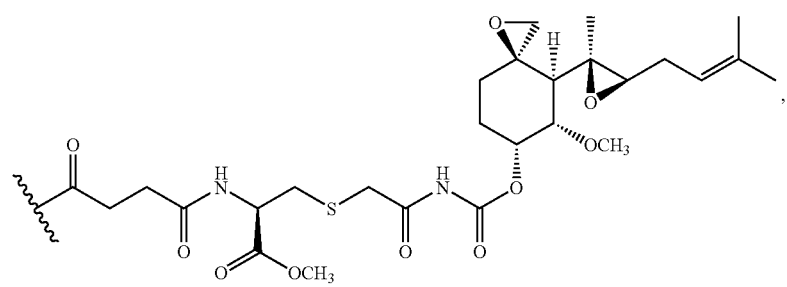
| 35 | PHF |
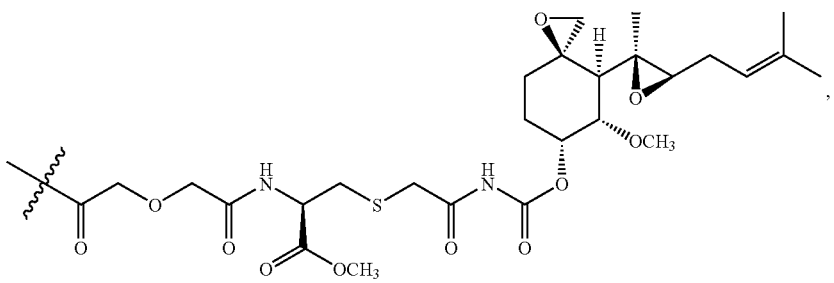

-continued
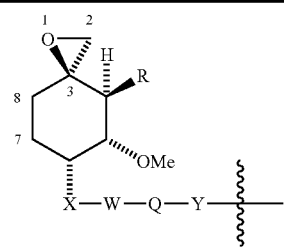
| Conjugate No. | Z |
|---|---|
| 36 | PHF |
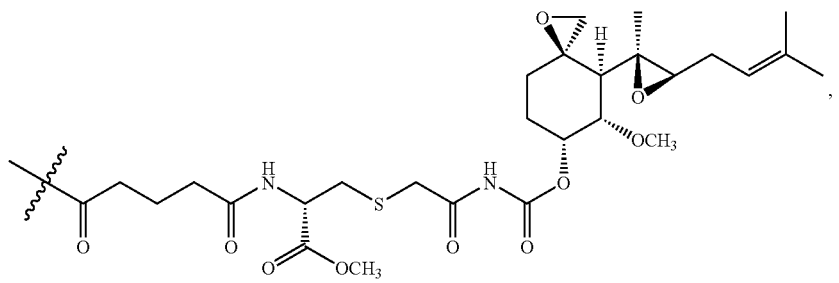
| 37 | PHF |
|---|---|
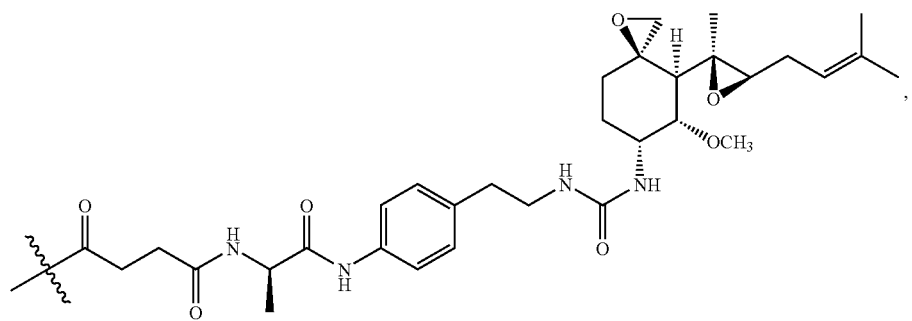
| 38 | PHF |
|---|---|
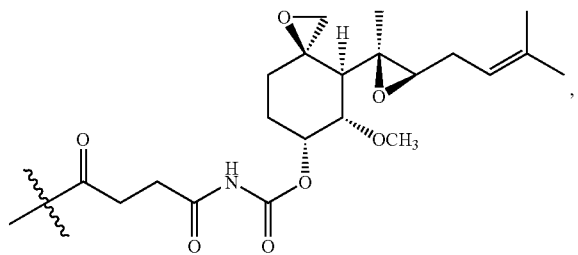
| 39 | PHF |
|---|---|
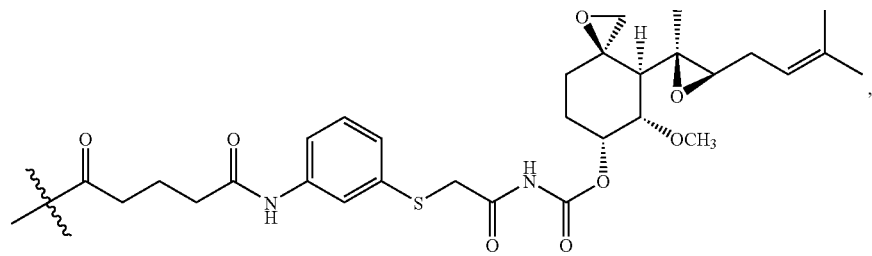
| 40 | PHF |
|---|---|
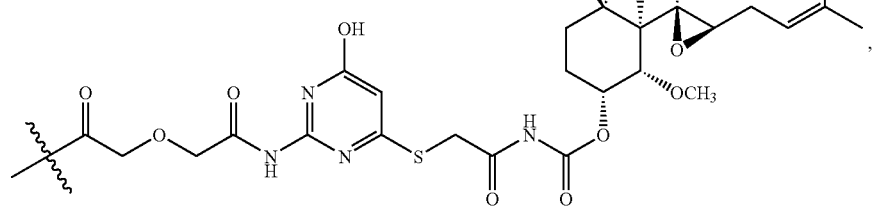

-continued
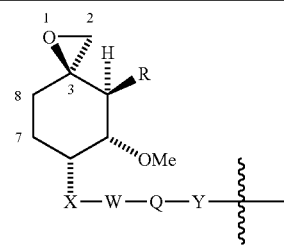
| Conjugate No. | Z | |
|---|---|---|
| 41 | PHF | 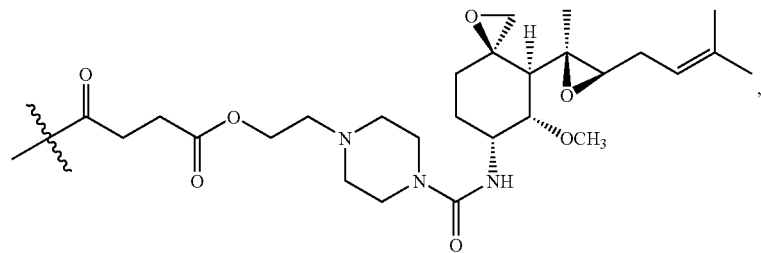 |
| 42 | PHF | 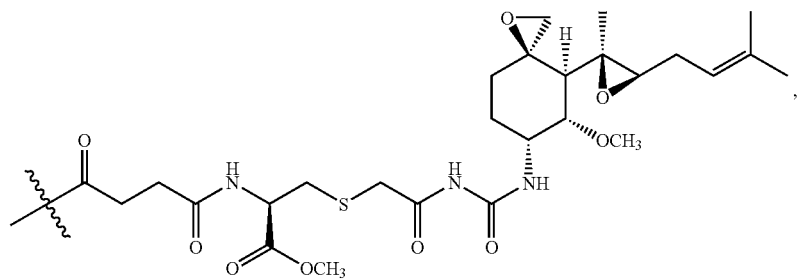 |
| 43 | PHF | 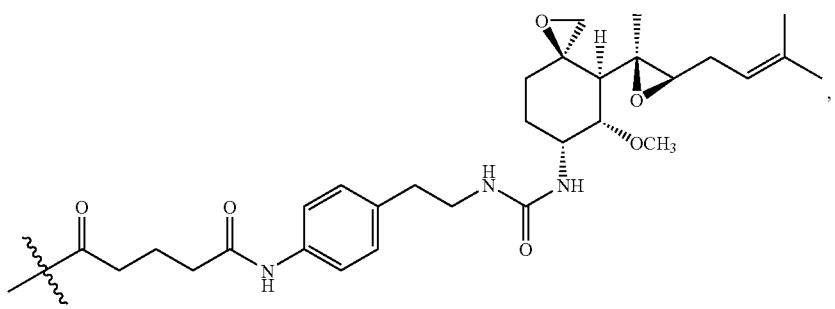 |
| | | and |
| 44 | PHF | 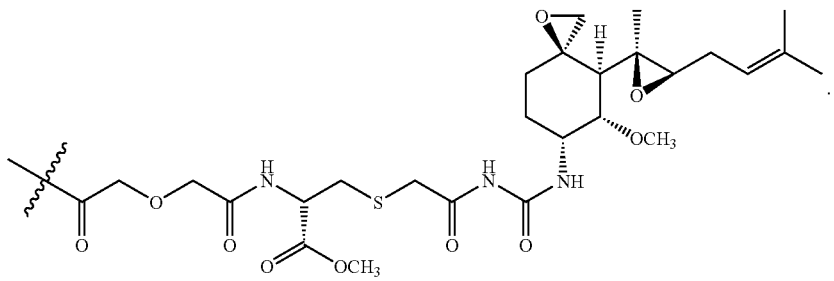 |
In another aspect, compounds of the Formula V are described:

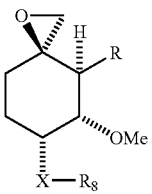

V wherein,

X is O, S(=O)$_q$, optionally substituted CH$_2$, or optionally substituted NH;

q is 0, 1, or 2;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C$_2$-heterocyclic-C$_1$-C$_6$ alkyl, C$_2$-heterocyclic-C$_2$-C$_6$ alkenyl, C$_1$-C$_6$ alkyl, C$_2$-C$_6$ alkenyl, C$_2$-heterocyclic-C$_1$-C$_6$-alkenyl-COO—C$_1$-C$_6$ alkyl, C$_2$-heterocyclic-C$_1$-C$_6$ alkyl-COO—C$_1$-C$_6$-alkyl, C$_1$-C$_6$ alkyl=N—O—C$_1$-C$_6$ alkyl-aryl, C(O)C$_1$-C$_6$ alkyl, CN, or halogen;

R$_8$ is selected from the group consisting of VI, VII, VIII, IX, X, XI, XII, and XIIA whose formulas are represented below:

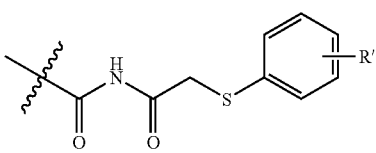

VI

R' is —CO$_2$H, optionally substituted —NH$_2$, or —N cyclic imide, NHC(O)(C$_1$-C$_6$ alkyl)-C(O)R", R' is meta or para in relation to the —S— atom; and R" is —OH, —O—C$_1$-C$_6$ alkyl, or —NH$_2$ optionally acylated through the carboxyl group of an amino acid;

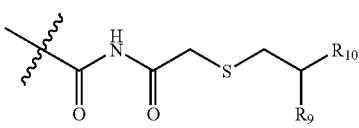

VII wherein R$_9$ is H or C(O)R$_{11}$;

R$_{10}$ is —NH$_2$, —NHCH(C$_1$-C$_6$ alkyl)-, —NHC(O)(C$_1$-C$_6$ alkyl), N-cyclized imide; —NH acylated through the carboxyl group of an amino acid, wherein the nitrogen of the amino group of the amino acid is optionally protected, and R$_{11}$ is OH, OC$_1$-C$_6$ alkyl, or optionally substituted —NH$_2$;

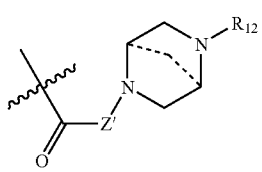

VIII wherein R$_{12}$ is H, C$_1$-C$_6$ alkyl, —(C$_1$-C$_6$)—COOH, —(C$_1$-C$_6$)—C(O)O—(C$_1$-C$_6$), —CH$_2$CH$_2$O—R$_{13}$, —C(O)(C$_1$-C$_6$-alkyl), or an amino acid attached through the carboxyl group of the amino acid;

R$_{13}$ is —H or an amino acid attached through the carboxyl group of the amino acid, wherein the nitrogen of the amino acid is optionally protected, or C(O)(C$_1$-C$_6$ alkyl)-COR";

R" is —OH, —OC$_1$-C$_6$ alkyl, or —NH$_2$ optionally acylated through the carboxyl group of an amino acid;

[-------] represents an optional methylene bridge (—CH$_2$—) between carbons 2 and 5 of the piperazine moiety; and Z' is a bond, —C$_1$-C$_6$ alkyl, —NHC(O)—, or —NHSO$_2$—;

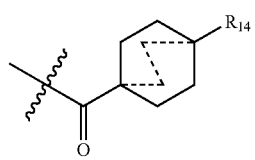

IX wherein R$_{14}$ is —H, —CO$_2$H, —CO$_2$(C$_1$-C$_6$ alkyl), —C(O)NH—C$_1$-C$_6$ alkyl-OH, wherein the O of —C(O)NH—C$_1$-C$_6$ alkyl-OH is optionally acylated with the carboxyl group of an amino acid; optionally substituted —NH$_2$, C$_1$-C$_6$-alkyl-NH$_2$, wherein the NH$_2$ is optionally substituted; and

[-------] represents an optional ethylene bridge (—CH$_2$CH$_2$—) between carbons 1 and 4 of the cyclohexane moiety;

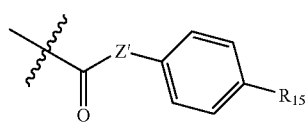

X

Z' is a bond, —CH$_2$—, —CH$_2$—S—, CH$_2$CH$_2$—, —C(H)(Me)-, NHCH$_2$—, —NHCH(CH$_3$)—, —NHCH$_2$CH$_2$—; and R$_{15}$ is H, optionally substituted —NH$_2$, —NHC(O)(C$_1$-C$_6$-alkyl), —N cyclized imide optionally containing a heteroatom within the cyclic structure, —NHC(O)CH$_2$OCH$_2$C(O)OH, NHC(O)CH(C$_1$-C$_6$ alkyl)-N cyclized imide, —NHC(O)CH(R")NHC(O)—(C$_1$-C$_6$ alkyl)-C(O)OH, —NHC(O)—(C$_1$-C$_6$ alkyl)-C(O)OH, —C(O)O(C$_1$-C$_6$ alkyl), —C(O)N(H)(C$_1$-C$_6$ alkyl)-OH, or NO$_2$;

R" is H, or —C$_1$-C$_6$ alkyl;

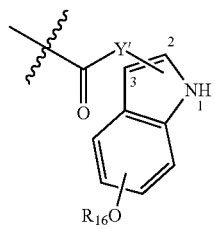

XI wherein Y' is C$_1$-C$_3$ alkyl, or NH—C$_1$-C$_3$ alkyl and is attached to positions 1, 2, or 3 of the indole; and $R_{16}$ is H, $C_1$-$C_6$ alkyl, —CH$_2$COOH, or —CH$_2$CH$_2$OH, wherein the O of —CH$_2$CH$_2$OH can be optionally acylated with an amino acid;

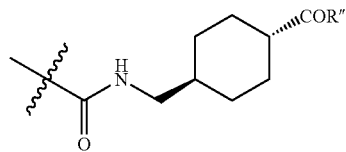
XII wherein R″ is —OH, —O$C_1$-$C_6$ alkyl, or —NH$_2$ optionally acylated through the carboxyl group of an amino acid; and

XIIA wherein Y″ is C(O)N(CH$_3$)(OCH$_3$), C(O)OCH$_3$, CH$_2$Cl, or NHC(O)CH$_2$Cl.

In one embodiment, R in Formula V is (2S,3R)-2-methyl-3-(3-methylbut-2-enyl)oxirane.

Illustrative examples of the Compounds of Formula V include the following compounds selected from the group consisting of:

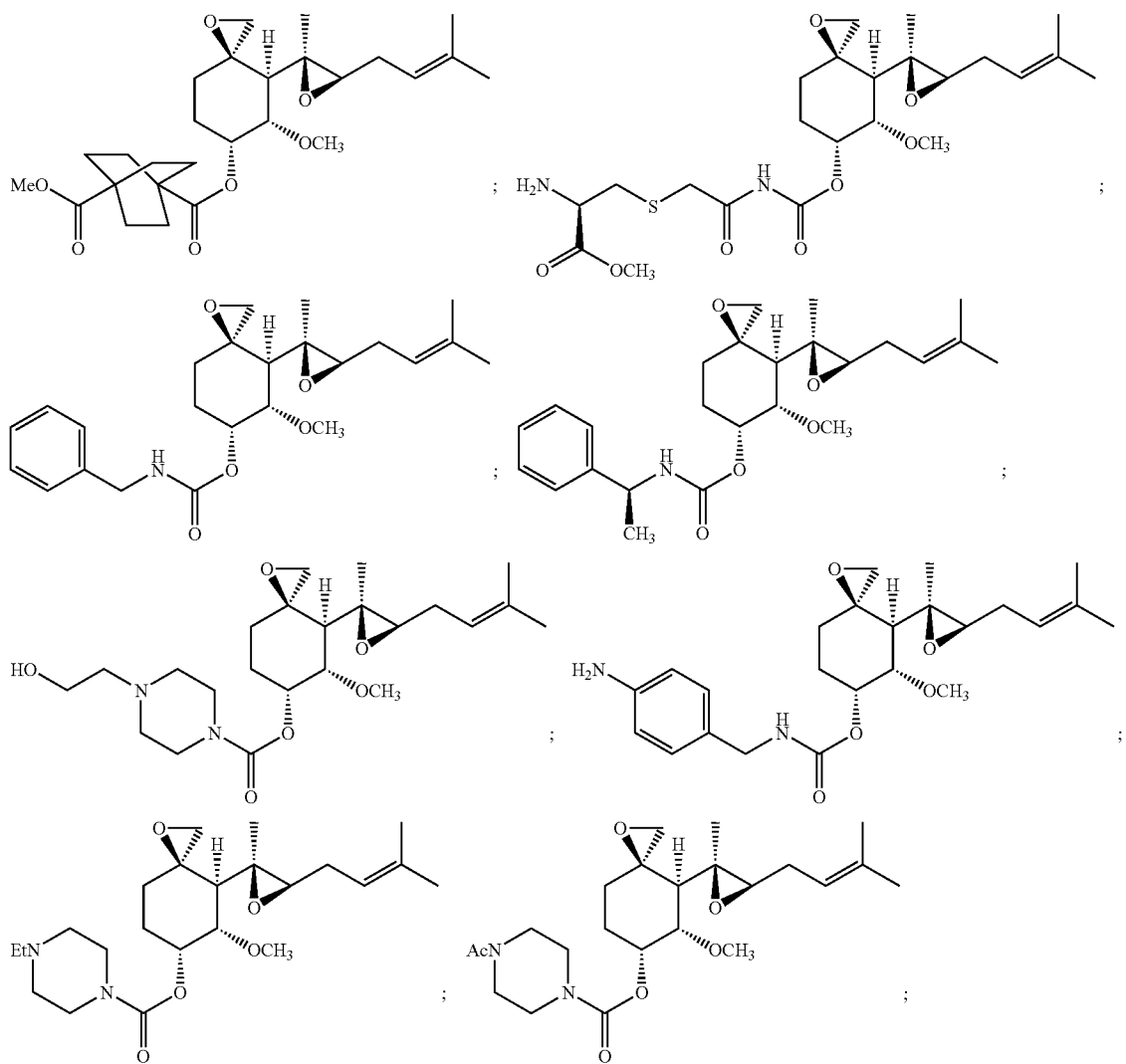

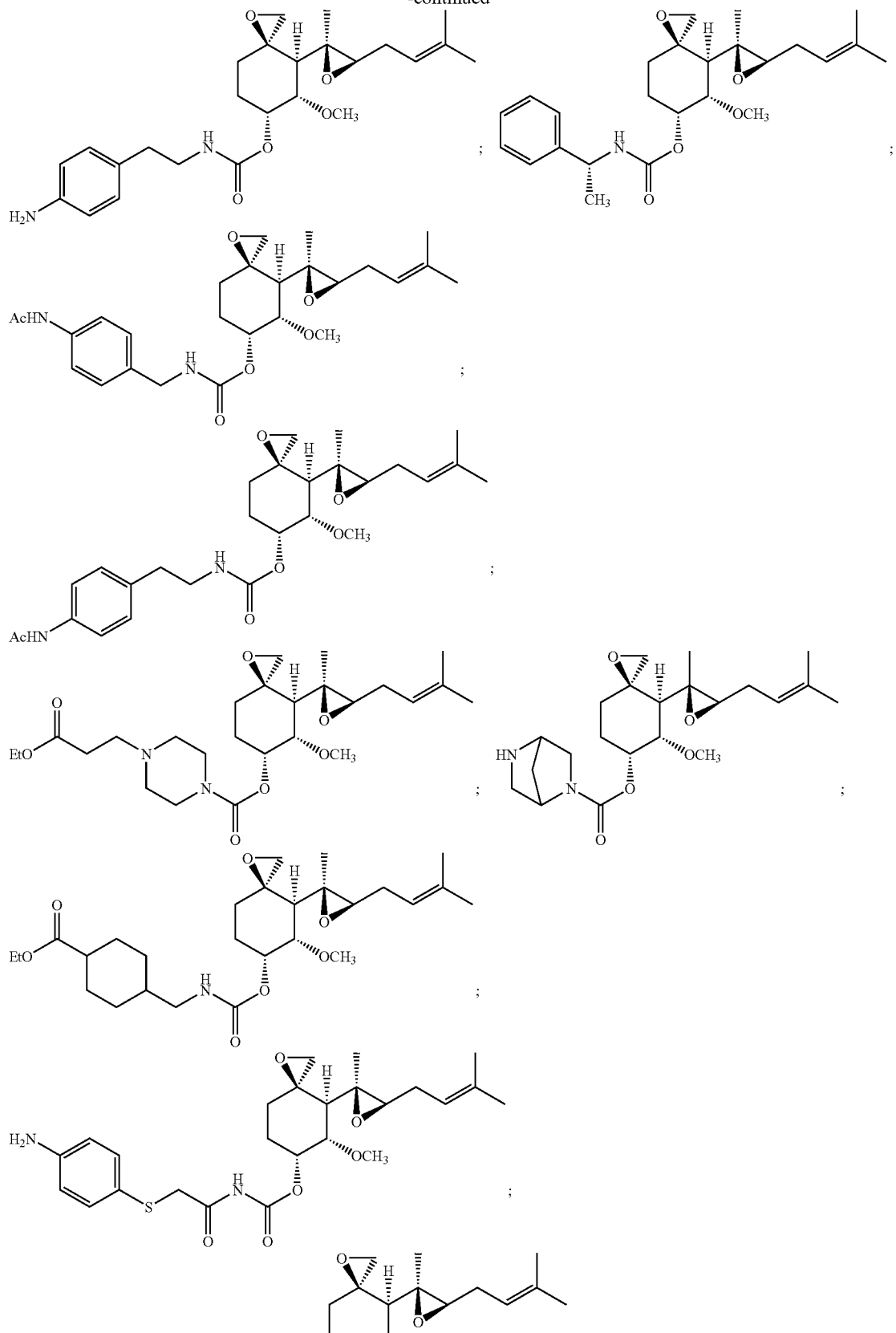

In another embodiment, illustrative compounds of Formula V which are released by the fumagillin conjugates described herein include the compounds selected from the group consisting of:
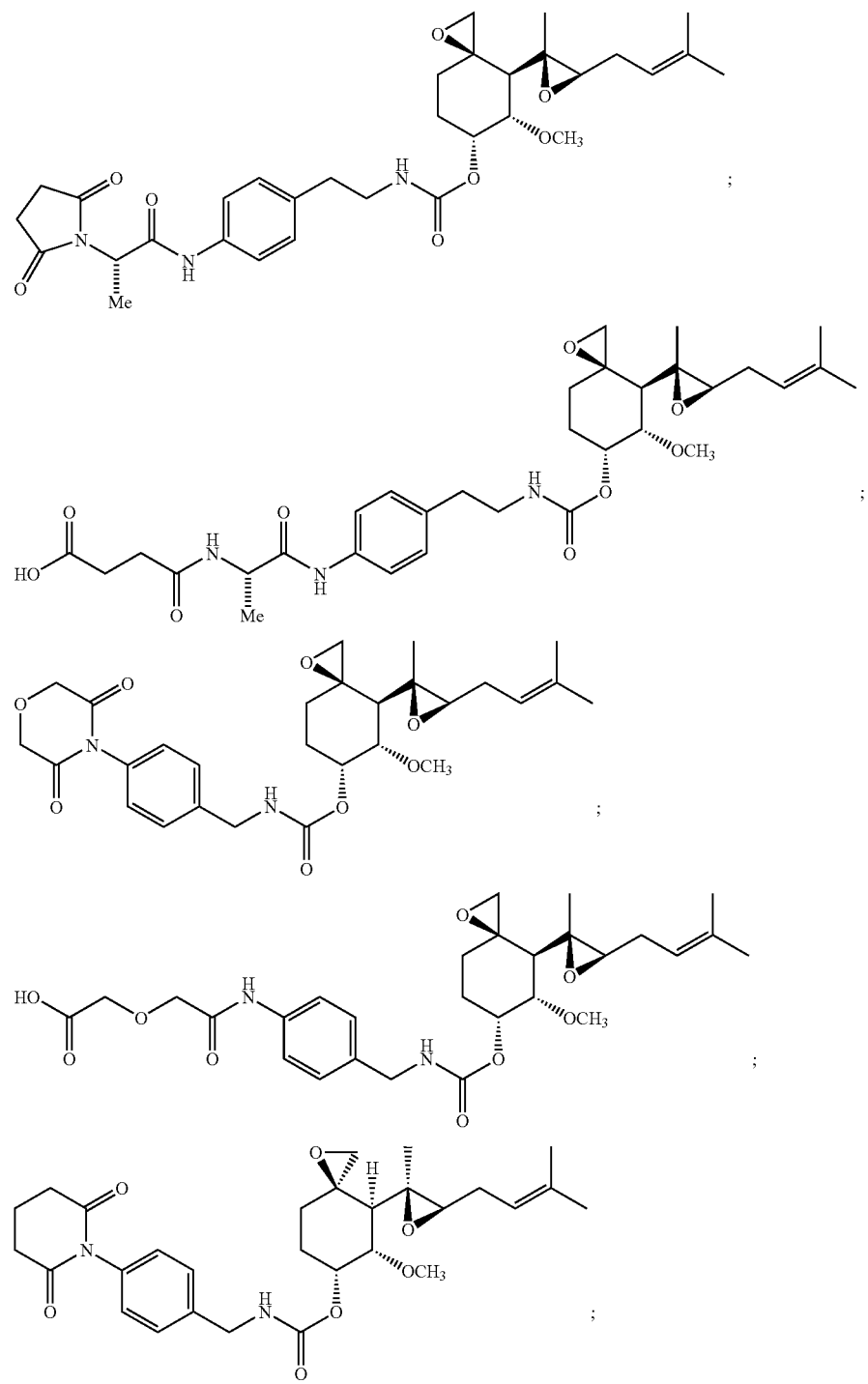

-continued

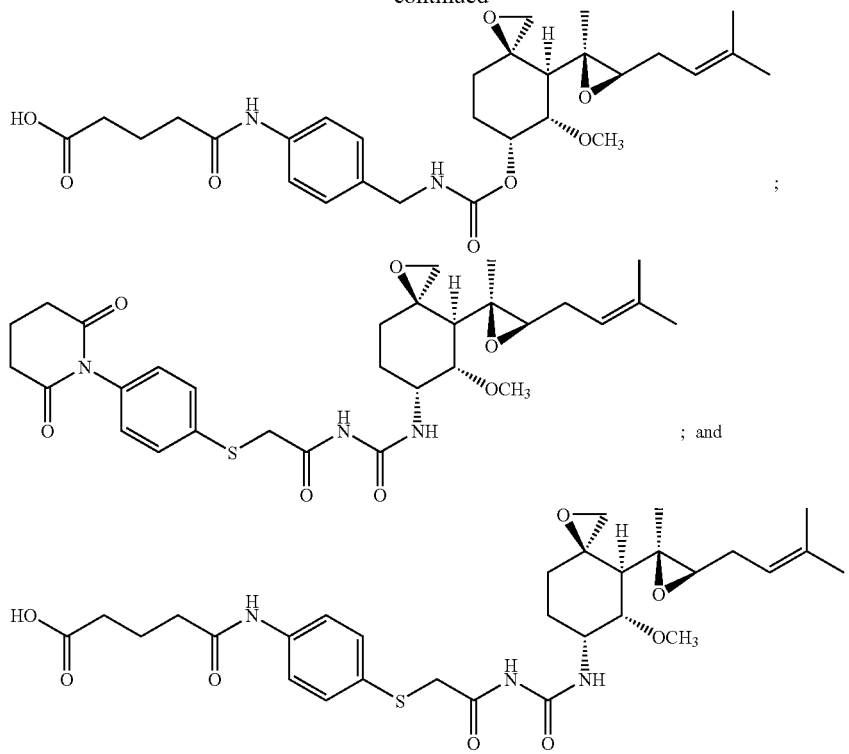

; and

Methods for Using the Fumagillin Analog Conjugates

In another aspect, compositions comprising at least one fumagillin analog conjugate or a pharmaceutically acceptable salt of a fumagillin analog conjugate and a pharmaceutically acceptable carrier are provided.

In another aspect, methods of treating an angiogenic disease, comprising administering to a subject in need thereof a fumagillin analog conjugate or a pharmaceutically acceptable salt of a fumagillin analog conjugate in an amount effective to inhibit angiogenesis is described.

In some embodiments, the angiogenic disease is selected from the group consisting of cancer, retinal neovascularization due to macular degeneration, psoriasis and pyogenic granuloma, rheumatoid, immune, and degenerative arthritis.

In another aspect, methods of treating cancer, comprising administering to a subject in need thereof a fumagillin analog conjugate or a pharmaceutically acceptable salt of a fumagillin analog conjugate in an amount effective to treat the cancer are described.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

In another aspect, a method of treating cancer, comprising co-administering to a subject in need thereof a fumagillin analog conjugate or a pharmaceutically acceptable salt of a fumagillin analog conjugate and a known anti-cancer agent, whereby the conjugate and the agent act synergistically is described.

In another aspect, a method of treating cancer is described, which comprises co-administering to a subject in need thereof a fumagillin analog conjugate or a pharmaceutically acceptable salt of a fumagillin analog conjugate and a known anti-cancer agent, whereby the conjugate and the agent act additively is described.

In some embodiments, the anti-cancer agent can be administered first and the fumagillin analog conjugate second or the fumagillin analog conjugate can be administered first and the anti-cancer agent second.

In another aspect, a method of treating cancer, comprising administering by metronomic dosing to a subject in need thereof a fumagillin analog conjugate or a pharmaceutically acceptable salt of a fumagillin analog conjugate is described. In other embodiments, thalidomide, interferon-α, interferon-β, or a COX-2 inhibitor can also be administered.

In another aspect, a method of treating cancer, comprising administering to a subject in need thereof a fumagillin analog conjugate or a pharmaceutically acceptable salt of a fumagillin analog conjugate, either of which deactivates an aminopeptidase is described.

In one embodiment, the aminopeptidase is methionine aminopeptidase type 2 (MetAP-2).

In another aspect, a method of reducing the central nervous system effect or toxicity in vivo or in vitro of a fumagillin analog is described which comprises conjugating said fumagillin analog to a polyal, including, but not limited to, PHF prior to administering the fumagillin analog to a subject.

In another aspect, a method of reducing the central nervous system effect or toxicity in vivo or in vitro of a fumagillin analog, as compared to TNP-470, comprising conjugating said fumagillin analog to PHF prior to administering the fumagillin analog to a subject is described.

Benefits of drug association with carrier macromolecules relate, in part, to the following factors: (1) solubilization of the drug substance; (2) restricted drug substance access to normal interstitium due to the large hydrodynamic size of the conjugate, (3) conjugate delivery to the tumor tissues via the Enhanced Permeability and Retention (EPR) effect, and (4) maintenance of sustained drug levels over periods exceeding cancer cell cycle.

Methods for Using the Fumagillin Analogs

In another aspect, compositions comprising at least one fumagillin analog or a pharmaceutically acceptable salt thereof and a pharmaceutically acceptable carrier are described.

In another aspect, methods of treating an angiogenic disease, comprising administering to a subject in need thereof a fumagillin analog or a pharmaceutically acceptable salt of a fumagillin analog in an amount effective to inhibit angiogenesis is described.

In some embodiments, the angiogenic disease is selected from the group consisting of cancer, retinal neovascularization due to macular degeneration, psoriasis and pyogenic granuloma, rheumatoid, immune, and degenerative arthritis.

In another aspect, methods of treating cancer, comprising administering to a subject in need thereof a fumagillin analog or a pharmaceutically acceptable salt of a fumagillin analog in an amount effective to treat the cancer are provided.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, gastric, and brain.

In another aspect, a method of inhibiting angiogenesis, comprising administering to a subject in need thereof a fumagillin analog or a pharmaceutically acceptable salt of a fumagillin analog in an amount effective to inhibit angiogenesis is described.

In another aspect, a method of treating cancer, comprising co-administering to a subject in need thereof a fumagillin analog or a pharmaceutically acceptable salt of a fumagillin analog and a known anti-cancer agent, whereby the conjugate and the agent act synergistically is described.

In another aspect, a method of treating cancer is described, which comprises co-administering to a subject in need thereof a fumagillin analog or a pharmaceutically acceptable salt of a fumagillin analog and a known anti-cancer agent, whereby the conjugate and the agent act additively is described.

In some embodiments, the anti-cancer agent can be administered first and the fumagillin analog second or the fumagillin analog can be administered first and the anti-cancer agent second.

In another aspect, a method of treating cancer, comprising administering by metronomic dosing to a subject in need thereof a fumagillin analog or a pharmaceutically acceptable salt of a fumagillin analog is described. In other embodiments, thalidomide, interferon-$\alpha$, interferon-$\beta$, or a COX-2 inhibitor can also be administered.

In another aspect, a method of treating cancer, comprising administering to a subject in need thereof a fumagillin analog or a pharmaceutically acceptable salt of a fumagillin analog, either of which deactivates an aminopeptidase is described.

In one embodiment, the aminopeptidase is methionine aminopeptidase type 2 (MetAP-2).

Therapeutic Administration of the Fumagillin Analog Conjugates

When administered to a subject, the fumagillin analog conjugates or pharmaceutically acceptable salts of the fumagillin analog conjugates can be administered as a component of a composition that comprises a physiologically acceptable carrier or vehicle. The compositions described herein can be prepared using a method comprising admixing the fumagillin analog conjugates or a pharmaceutically acceptable salt of the fumagillin analog conjugates and a physiologically acceptable carrier, excipient, or diluent. Admixing can be accomplished using methods well known for admixing a fumagillin analog conjugate or a pharmaceutically acceptable salt of the fumagillin analog conjugate and a physiologically acceptable carrier, excipients, or diluents.

The fumagillin analog conjugates or pharmaceutically acceptable salts of fumagillin analog conjugates can be administered by any convenient route, for example, by infusion or bolus injection and can be administered together with another therapeutic agent. Administration of the fumagillin analog conjugate will result in release of a fumagillin analog into the bloodstream.

In one embodiment, the fumagillin analog conjugate or a pharmaceutically acceptable salt of the fumagillin analog conjugate is administered intravenously.

The present compositions can optionally comprise a suitable amount of physiologically acceptable excipients.

In variations of these embodiments, it may be desirable to include other pharmaceutically active compounds, such as anti-inflammatories or steroids which are used to reduce swelling, antibiotics, antivirals, or antibodies. Other compounds which can be included are preservatives, antioxidants, and fillers, coatings or bulking agents which may also be utilized to alter polymer matrix stability and/or drug release rates.

Buffers, acids and bases are used to adjust the pH of the composition.

Fillers are water soluble or insoluble materials incorporated into the formulation to add bulk. Types of fillers include sugars, starches and celluloses. The amount of filler in the formulation will typically be in the range of between about 1 and about 90% by weight.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment, the physiologically acceptable excipients are sterile when administered to a subject. The physiologically acceptable excipient should be stable under the conditions of manufacture and storage and should be preserved against the contaminating action of microorganisms. Water is a particularly useful excipient when the fumagillin analog conjugate or a pharmaceutically acceptable salt of the fumagillin analog conjugate is administered intravenously. Saline solutions and aqueous dextrose and glycerol solutions can also be employed as liquid excipients, particularly for injectable solutions. Suitable physiologically acceptable excipients also include bulking agents like sorbitol and mannitol and surfactants like polysorbates, hydroxypropyl-$\beta$-cyclodextrin, and poloxamer. The present compositions, if desired, can also contain minor amounts of pH buffering agents.

Liquid carriers may be used in preparing solutions. The fumagillin analog conjugate or pharmaceutically acceptable salt of the fumagillin analog conjugate can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, colors, viscosity regulators, stabilizers, or osmo-regulators.

The present compositions can take the form of solutions for injection, or any other form suitable for use. Other examples of suitable physiologically acceptable excipients are described in Remington's Pharmaceutical Sciences pp. 1447-1676 (Alfonso R. Gennaro, Ed., 19th ed. 1995).

In another embodiment, the fumagillin analog conjugate or a pharmaceutically acceptable salt of the fumagillin analog conjugate can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the fumagillin analog conjugate or a pharmaceutically acceptable salt of the fumagillin analog conjugate is to be administered by infusion, it can be dispensed, for example, with an infusion bottle containing sterile pharmaceutical grade water or saline. Where the fumagillin analog conjugate or a pharmaceutically acceptable salt of the fumagillin analog conjugate is administered by injection, an ampule of sterile water for injection or saline can be provided so that the ingredients can be mixed prior to administration.

The amount of the fumagillin analog conjugate or a pharmaceutically acceptable salt of the fumagillin analog conjugate that is effective for treating or preventing cancer, or inhibiting angiogenesis can be determined using standard clinical techniques. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. The typical dose will range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 20 mg/kg of body weight per day. Dosages are based on the amount of the equivalents of fumagillin analog present on the conjugate. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one fumagillin analog conjugate or more than one pharmaceutically acceptable salt of the fumagillin analog conjugate is administered, the effective dosage amounts correspond to the total amount administered.

Effective amounts of the other prophylactic or therapeutic agents are well known to those skilled in the art. However, it is well within the skilled artisan's purview to determine the other prophylactic or therapeutic agent's optimal effective amount range. In one embodiment, where another prophylactic or therapeutic agent is administered to a subject, the effective amount of the fumagillin conjugate is less than its effective amount would be if the other prophylactic or therapeutic agent is not administered. In this case, without being bound by theory, it is believed that fumagillin analog conjugate and the other prophylactic or therapeutic agent act in an additive or synergistic way to treat cancer, inflammatory diseases, or inhibit angiogenesis.

The present methods for treating cancer, or inhibiting angiogenesis, can further comprise administering another therapeutic agent to the subject being administered the fumagillin analog conjugate. In one embodiment, the other therapeutic agent is administered in an effective amount.

Suitable other therapeutic agents useful in the methods and compositions include, but are not limited to, anti-cancer agents, anti-angiogenesis agents, anti-inflammatory agents, and irritable bowel syndrome agents.

Suitable anti-cancer agents useful in the methods and compositions include, but are not limited to, temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, camptothecins, bleomycin, doxorubicin, idarubicin, daunorubicin, dactinomycin, plicamycin, mitoxantrone, L-asparaginase, epirubicin, 5-fluorouracil, taxanes such as docetaxel and paclitaxel, leucovorin, levamisole, irinotecan, estramustine, etoposide, nitrogen mustards, 1,3-bis(2-chloroethyl)-1-nitrosourea (BCNU), nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins, herbimycin A, genistein, erbstatin, and lavendustin A.

Other therapeutic agents useful in the methods and compositions include, but are not limited to, hydroxyzine, glatiramer acetate, interferon $\beta$-1a, interferon $\beta$-1b, and natalizumab.

Anti-angiogenesis agents are also therapeutic agents useful in the methods and compositions described herein. Non-limiting examples of anti-angiogenesis agents include bevacizumab (Avastin°), sunitinib (Sutent®), sorafenib (Nexavar®), thalidomide (Thalomid®), lenalidomide (Revlimid®), panitumumab (Vectibix®), cetuximab (Erbitux®), and erlotinib (Tarceva®).

In one embodiment, the fumagillin analog conjugate or a pharmaceutically acceptable salt of the fumagillin analog conjugate is administered concurrently with another therapeutic agent.

In one embodiment, a composition comprising an effective amount of the fumagillin analog conjugate or a pharmaceutically acceptable salt of the fumagillin analog conjugate and an effective amount of another therapeutic agent within the same composition can be administered.

In another embodiment, a composition comprising an effective amount of the fumagillin analog conjugate or a pharmaceutically acceptable salt of the fumagillin analog conjugate and a separate composition comprising an effective amount of another therapeutic agent can be concurrently administered.

In another embodiment, an effective amount of the fumagillin analog conjugate or a pharmaceutically acceptable salt of the fumagillin analog conjugate is administered prior to or subsequent to administration of an effective amount of another therapeutic agent. In this embodiment, the fumagillin analog conjugate or a pharmaceutically acceptable salt of the fumagillin analog conjugate is administered while the other therapeutic agent exerts its therapeutic effect, or the other therapeutic agent is administered while the fumagillin analog conjugate or a pharmaceutically acceptable salt of the fumagillin analog conjugate exerts its preventative or therapeutic effect in treating cancer, or inhibiting angiogenesis.

Therapeutic Administration of the Fumagillin Analogs

When administered to a subject, the fumagillin analog or pharmaceutically acceptable salt of the fumagillin analog can be administered as a component of a composition that comprises a physiologically acceptable carrier or vehicle. A composition can be prepared using a method comprising admixing the fumagillin analog or a pharmaceutically acceptable salt of the fumagillin analog and a physiologically acceptable carrier, excipient, or diluent.

Methods of administration of the analogs themselves include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin.

The fumagillin analog or pharmaceutically acceptable salt of fumagillin analog can be administered by any other convenient route, for example, by infusion or bolus injection and can be administered together with another therapeutic agent. Administration can be systemic or local. Various known delivery systems, including encapsulation in liposomes, microparticles, microcapsules, and capsules, can be used.

In one embodiment, the fumagillin analog or a pharmaceutically acceptable salt of the fumagillin analog is administered orally.

In one embodiment, the fumagillin analog or a pharmaceutically acceptable salt of the fumagillin analog is administered intravenously.

In another embodiment, the fumagillin analog or a pharmaceutically acceptable salt of the fumagillin analog can be administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, or fibers.

In yet another embodiment, the fumagillin analog or a pharmaceutically acceptable salt of the fumagillin analog can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, R., (1990) *Science*, 249:1527-1533 can be used. In one embodiment, a pump can be used (Langer, R., (1990) *Science*, 249:1527-1533; Sefton, M., (1987) *CRC Crit. Ref. Biomed. Eng.*, 14: 201; Buchwald H., et al., (1980) *Surgery*, 88: 507; and Saudek C., et al., (1989) *N. Engl. J. Med.*, 321: 574). In another embodiment, polymeric materials can be used (see *Medical Applications of Controlled Release*, (Langer and Wise eds., 1974); *Controlled Drug Bioavailability, Drug Product Design and Performance*, (Smolen and Ball eds., 1984); Ranger and Peppas, (1983) *J. Macromol. Sci. Rev. Macromol. Chem.*, 2: 61; Levy et al., (1985) *Science*, 228: 190; During et al., (1989) *Ann. Neural.*, 25:351; and Howard et al., (1989) *J. Neurosurg.*, 71: 105).

The present compositions can optionally comprise a suitable amount of physiologically acceptable excipients.

In variations of these embodiments, it may be desirable to include other pharmaceutically active compounds, such as antiinflammatories or steroids which are used to reduce swelling, antibiotics, antivirals, or antibodies. Other compounds which can be included are preservatives, antioxidants, and fillers, coatings or bulking agents which may also be utilized to alter polymer matrix stability and/or drug release rates.

Fillers are water soluble or insoluble materials incorporated into the formulation to add bulk. Types of fillers include sugars, starches and celluloses. The amount of filler in the formulation will typically be in the range of between about 1 and about 90% by weight.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment, the physiologically acceptable excipients are sterile when administered to a subject. The physiologically acceptable excipient should be stable under the conditions of manufacture and storage and should be preserved against the contaminating action of microorganisms. Saline solutions and aqueous dextrose and glycerol solutions can also be employed as liquid excipients, particularly for injectable solutions. Suitable physiologically acceptable excipients also include bulking agents like sorbitol and mannitol and surfactants like polysorbates, hydroxypropyl-$\beta$-cyclodextrin, and poloxamer. The present compositions, if desired, can also contain minor amounts of pH buffering agents.

Liquid carriers may be used in preparing solutions, suspensions, emulsions, syrups, and elixirs. The fumagillin analogs or pharmaceutically acceptable salts of the fumagillin analogs can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions for injection, or any other form suitable for use. Other examples of suitable physiologically acceptable excipients are described in Remington's Pharmaceutical Sciences pp. 1447-1676 (Alfonso R. Gennaro, ed., 19th ed. 1995).

Surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

In another embodiment, the fumagillin analog or a pharmaceutically acceptable salt of the fumagillin analog can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the fumagillin analog or a pharmaceutically acceptable salt of the fumagillin analog is to be administered by infusion, it can be dispensed, for example, with an infusion bottle containing sterile pharmaceutical grade water or saline. Where the fumagillin analog or a pharmaceutically acceptable salt of the fumagillin analog is administered by injection, an ampule of sterile water for injection or saline can be provided so that the ingredients can be mixed prior to administration.

The amount of the fumagillin analog or a pharmaceutically acceptable salt of the fumagillin analog that is effective for treating or preventing treating cancer, or inhibiting angiogenesis can be determined using standard clinical techniques. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. The typical dose will range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 20 mg/kg of body weight per day. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one fumagillin analog or more than one pharmaceutically acceptable salt of the fumagillin analog is administered, the effective dosage amounts correspond to the total amount administered.

Effective amounts of the other prophylactic or therapeutic agents are well known to those skilled in the art. However, it is well within the skilled artisan's purview to determine the other prophylactic or therapeutic agent's optimal effective amount range. In one embodiment, when another prophylactic or therapeutic agent is administered to a subject, the effective amount of the fumagillin analog is less than its effective amount would be where the other prophylactic or therapeutic agent is not administered. In this case, without being bound by theory, it is believed that fumagillin analog and the other prophylactic or therapeutic agent act in an additive or synergistic way to treat cancer, inflammatory diseases, or inhibit angiogenesis.

In one embodiment, the pharmaceutical composition comprising a fumagillin analog is in unit dosage form, e.g., as a tablet, capsule, powder, solution, suspension, emulsion, granule, or suppository. In such form, the composition is subdivided in unit dose containing appropriate quantities of the active ingredient; the unit dosage form can be packaged compositions, for example, packeted powders, vials, ampoules, pre-filled syringes or sachets containing liquids. The unit dosage form can be, for example, a capsule or tablet itself, or it can be the appropriate number of any such compositions in package form. Such unit dosage form may contain from about 1 mg/kg to about 250 mg/kg of fumagillin analog, and may be given in a single dose or in two or more divided doses.

The fumagillin analog or a pharmaceutically acceptable salt of the fumagillin analog can be assayed in vitro or in vivo for the desired therapeutic or prophylactic activity prior to use in humans. Animal model systems can be used to demonstrate safety and biological activity.

The present methods for treating cancer, or inhibiting angiogenesis, can further comprise administering another therapeutic agent to the subject being administered the fumagillin analog. In one embodiment, the other therapeutic agent is administered in an effective amount.

Suitable other therapeutic agents useful in the methods and compositions described herein include, but are not limited to, anti-cancer agents, anti-angiogenesis agents, anti-inflammatory agents, and irritable bowel syndrome agents.

Suitable anti-cancer agents useful in the methods and compositions described herein include, but are not limited to, temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, camptothecins, bleomycin, doxorubicin, idarubicin, daunorubicin, dactinomycin, plicamycin, mitoxantrone, L-asparaginase, epirubicin, 5-fluorouracil, taxanes such as docetaxel and paclitaxel, leucovorin, levamisole, irinotecan, estramustine, etoposide, nitrogen mustards, 1,3-bis(2-chloroethyl)-1-nitrosourea (BCNU), nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins, herbimycin A, genistein, erbstatin, and lavendustin A.

Other therapeutic agents useful in the methods and compositions include, but are not limited to, hydroxyzine, glatiramer acetate, interferon beta-1a, interferon beta-1b, and natalizumab.

Suitable anti-angiogenesis agents useful in the methods and compositions include, bevacizumab (Avastin®), sunitinib (Sutent®), sorafenib (Nexavar®), thalidomide (Thalomid®), and lenalidomide (Revlimid®), panitumumab, erbitux, and erlotinib (Tarceva®).

In one embodiment, the fumagillin analog or a pharmaceutically acceptable salt of the fumagillin analog is administered concurrently with another therapeutic agent.

In one embodiment, a composition comprising an effective amount of the fumagillin analog or a pharmaceutically acceptable salt of the fumagillin analog and an effective amount of another therapeutic agent within the same composition can be administered.

In another embodiment, a composition comprising an effective amount of the fumagillin analog or a pharmaceutically acceptable salt of the fumagillin analog and a separate composition comprising an effective amount of another therapeutic agent can be concurrently administered.

In another embodiment, an effective amount of the fumagillin analog or a pharmaceutically acceptable salt of the fumagillin analog is administered prior to or subsequent to administration of an effective amount of another therapeutic agent. In this embodiment, the fumagillin analog or a pharmaceutically acceptable salt of the fumagillin analog is administered while the other therapeutic agent exerts its therapeutic effect, or the other therapeutic agent is administered while the fumagillin analog or a pharmaceutically acceptable salt of the fumagillin analog exerts its preventative or therapeutic effect in treating cancer, or inhibiting angiogenesis.

The fumagillin analog conjugates and pharmaceutically acceptable salts of fumagillin analog conjugates can be prepared using a variety of methods starting from commercially available compounds, known compounds, or compounds prepared by known methods. The fumagillin analogs and pharmaceutically acceptable salts of fumagillin analogs can be prepared using a variety of methods starting from commercially available compounds, known compounds, or compounds prepared by known methods. General synthetic routes to many of the compounds described are included in the following schemes. It is understood by those skilled in the art that protection and deprotection steps not shown in the Schemes may be required for these syntheses, and that the order of steps may be changed to accommodate functionality in the target molecule.

Methods useful for making the fumagillin analog conjugates and the fumagillin analogs are set forth in the Examples below and generalized in the following schemes.

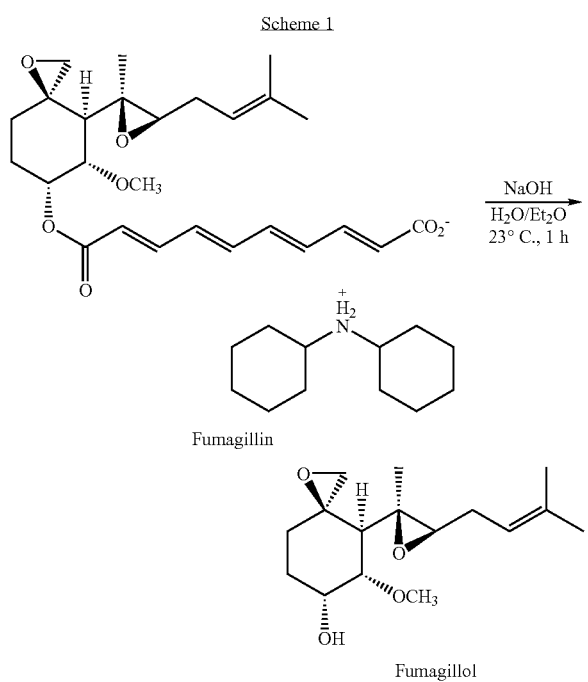

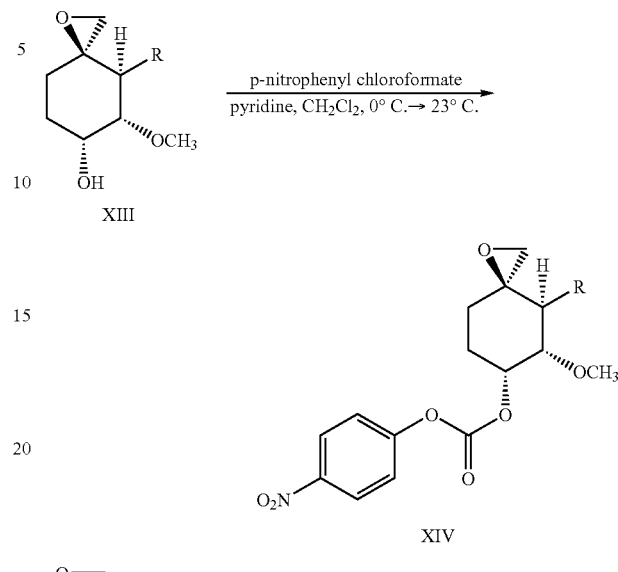

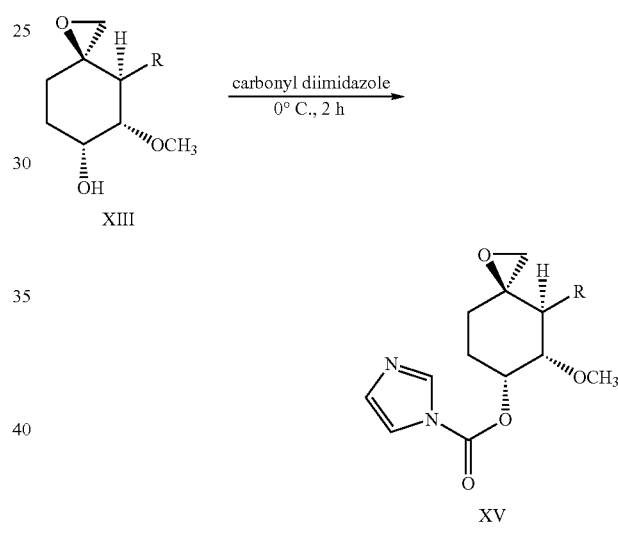

wherein R is as defined above for Formula II.

As set forth in Scheme 2, a compound of formula XIII can be reacted with p-nitrophenyl chloroformate in an organic solvent such as methylene chloride with a base such as pyridine at about 0° C. and allowed to stir. After quenching the reaction, standard workup gives a compound of the formula XIV. Alternatively, substituting p-nitrophenyl chloroformate with carbonyl diimidazole gives a compound of the formula XV.

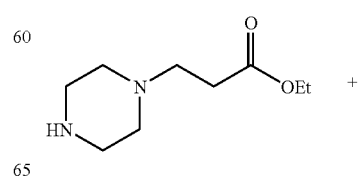

-continued

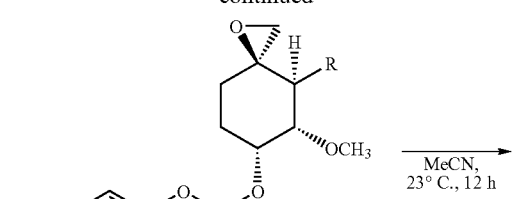

XIV

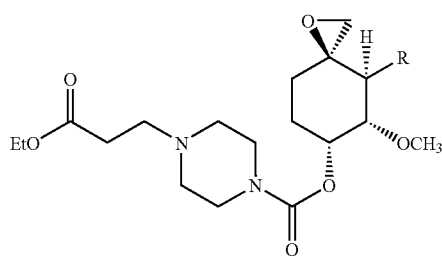

XVI wherein R is as defined above for Formula II.

As set forth in Scheme 3, a compound of the formula XIV can be reacted with an amine such as ethyl 3-(piperazin-1-yl) propanoate at room temperature for 12 hours. Standard extraction and purification of the reaction mixture gives a compound of the formula XVI.

Scheme 4

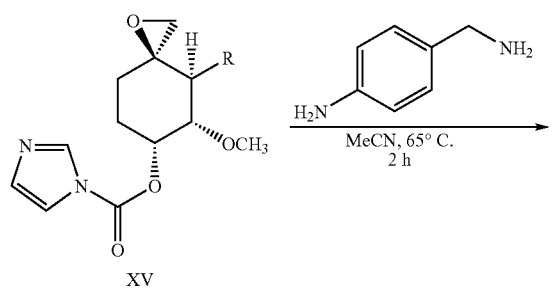

XV

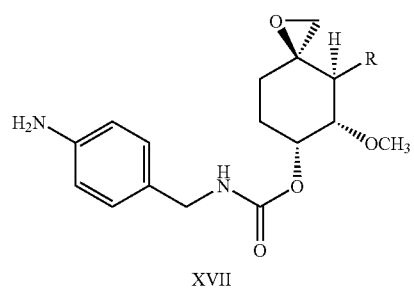

XVII wherein R is as defined above for Formula II.

As set forth in Scheme 4, a compound of the formula XV can be reacted with a primary amine such as 4-(aminomethyl) aniline at 65° C. in an aprotic organic solvent such as acetonitrile to give a compound of the formula XVII.

Scheme 5

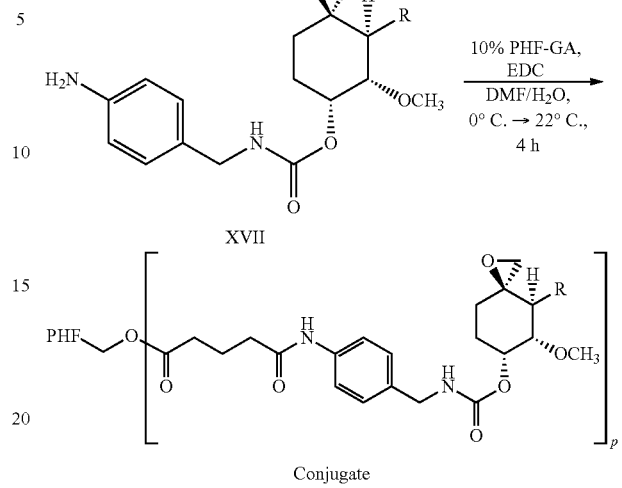

XVII

Conjugate wherein p=m, and m and R are as defined above for Formula I and II, respectively.

As set forth in Scheme 5 conjugates can be synthesized by dissolving PHF-GA (made according to U.S. 2007/0190018) with a compound of the formula XVII in a solvent mixture of an organic solvent such as DMF or acetonitrile and water. The pH is adjusted to between 5.9 and 6.0 and the reaction mixture cooled to 0° C. Afterwards 1-ethyl-3-(3-dimethylaminopropyl)-carbodiimide (EDC) is added, and the mixture stirred for about 2.5 to 4 hours. The reaction mixture is acidified to pH 5 with 1.0 N HCl and the mixture filtered through a 0.2µ membrane and purified by size exclusion chromatography to give, for example, Conjugate 12 when R is (2S,3R)-2-methyl-3-(3-methylbut-2-enyl) oxirane.

Scheme 6

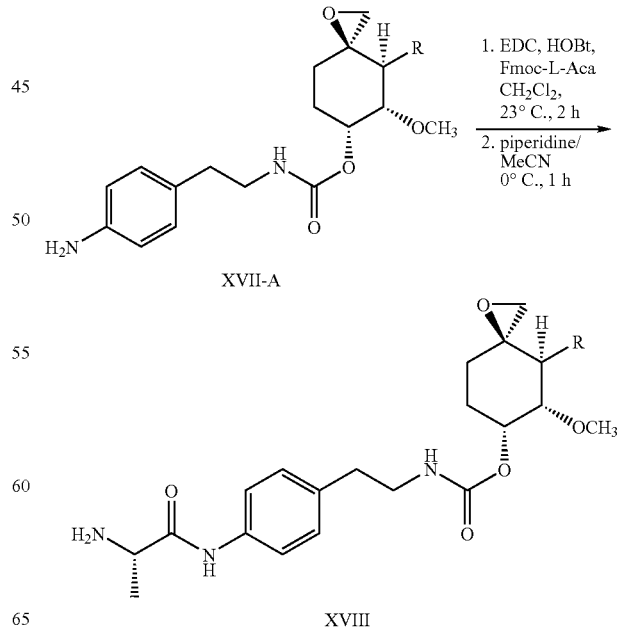

XVII-A

XVIII wherein R is as defined above for Formula II.

As set forth in Scheme 6, a compound of the formula XVII-A can be coupled to an organic acid, such as an amino acid, by dissolving it together with an organic acid, such as Fmoc protected L-alanine, and EDC in an aprotic organic solvent such as methylene chloride. Subsequently, the Fmoc protecting group can be removed by reaction with piperidine in an aprotic solvent such as acetonitrile. Extraction and chromatographic purification gives a compound of the formula XVIII.

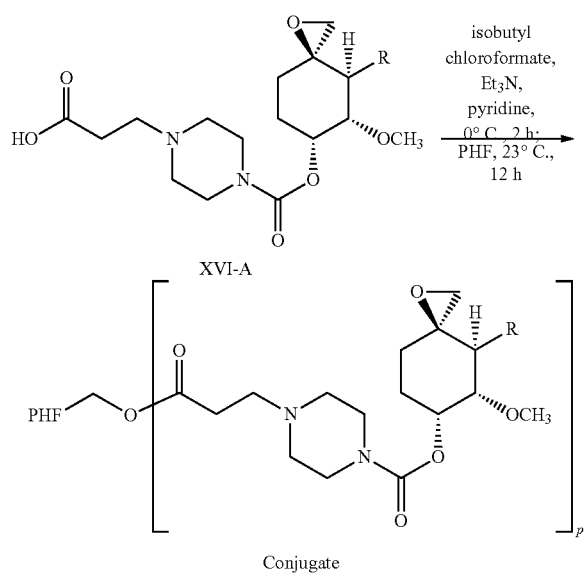

Scheme 7

XVI-A

Conjugate wherein p=m, and m and R are as defined above for Formula I and II, respectively.

As set forth in Scheme 7, an alternative method for coupling a fumagillin analog to a polyal involves dissolving a compound of the formula XVI-A in THF and cooling the reaction to 0° C. A base such as triethylamine and isobutyl chloroformate are added and the mixture stirred. In a second vessel PHF is dissolved in anhydrous pyridine. Afterwards, the contents of both vessels are combined and allowed to stir and warm to room temperature over 12 hours. The mixture is filtered, as described above, and purified by size exclusion, giving for example Conjugate 4 when R is (2S,3R)-2-methyl-3-(3-methylbut-2-enyl) oxirane.

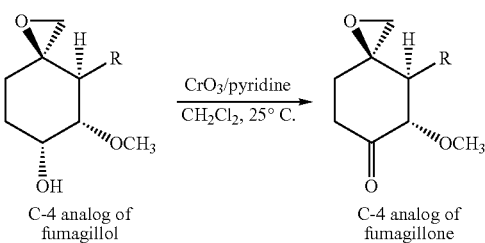

Scheme 8

C-4 analog of fumagillol

C-4 analog of fumagillone wherein R is as defined above for Formula II.

As set forth in Scheme 8, fumagillone and its C-4 analogs can be produced by reacting fumagillol and its C-4 analogs with an oxidizing agent such as Chromium (VI) oxide in pyridine with stirring overnight at room temperature. Standard workup by extraction and chromatography on silica gel provides fumagillone and its C-4 analogs.

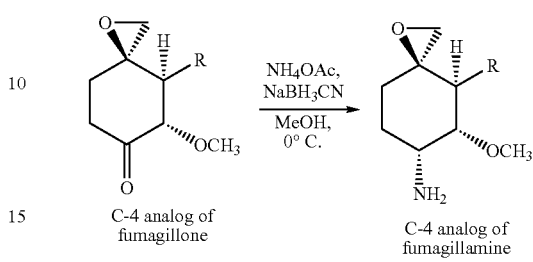

Scheme 9

C-4 analog of fumagillone

C-4 analog of fumagillamine wherein R is as defined above for Formula II.

As set forth in Scheme 9, fumagillamine and its C-4 analogs can be produced by reacting a fumagillone analog in anhydrous MeOH with ammonium acetate and sodium cyanoborohydride.

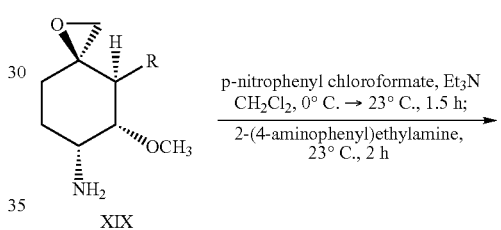

Scheme 10

XIX

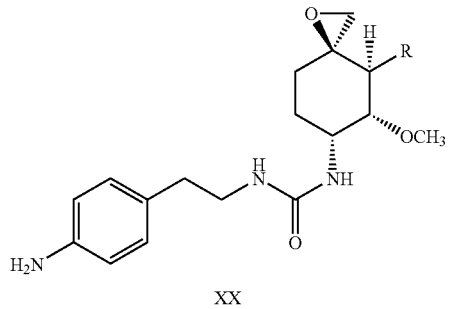

XX wherein R is as defined above for Formula II.

As set forth in Scheme 10, a compound of formula XIX can be reacted with p-nitrophenyl chloroformate in an organic solvent such as methylene chloride with a base such as triethylamine at 0° C. and allowed to stir and warm to room temperature. Afterwards a solution of 2-(4-aminophenyl)ethylamine is added and after stirring for a further 2 hours the reaction is quenched which after workup gives a compound of the formula XX.

Scheme 11

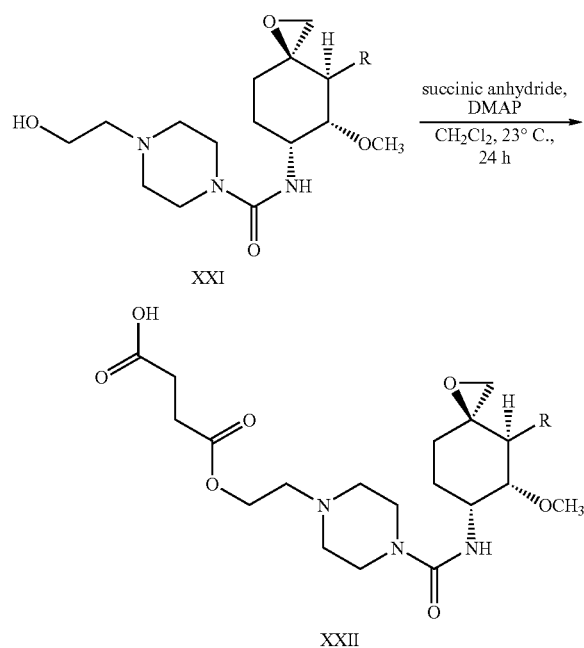

wherein R is as defined above for Formula II.

As set forth in Scheme 11, a compound of the formula XXI can be reacted with an anhydride, such as succinic anhydride, in the presence of DMAP in CH₂Cl₂ to give a compound of the formula XXII.

Scheme 12

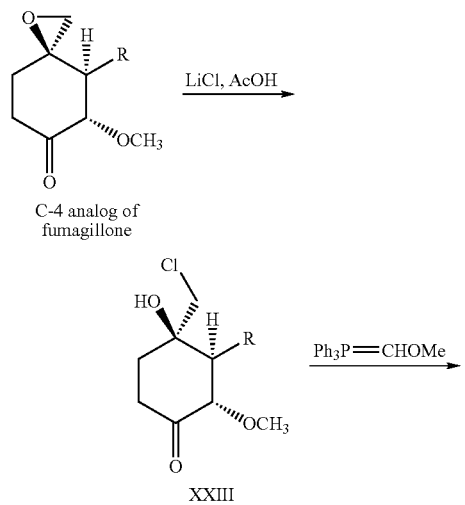

wherein R is as defined above for Formula II.

As set forth in Scheme 12, the synthesis of a C-6 carbo derivative of fumagillin can be accomplished starting with fumagillone where the spiro-epoxide is protected as a chlorohydrin XXIII (*Bioorg. Med. Chem. Lett.* 2003, 11, 5051-5058). Subsequently, a Horner-Wittig reaction (*Journal of Chem. Soc.* 1988, 17, 1184-1186) gives a compound such as XXIV, followed by hydrolysis of the resulting methyl enol ether (*Synth. Commun.* 2001, 31, 939-946) and lastly, reformation of the spiro-epoxide with potassium tert-butoxide (*Bioorg. Med. Chem. Lett.* 2004, 14, 91-94) will afford a fumagillin analogue with a C-6 methylene such as a compound of formula XXV.

Scheme 13 wherein R is as defined above for Formula II.

As set forth in Scheme 13, the C-6 thio analog XXVI can be synthesized by reacting the C-6 keto analog with Lawesson's reagent in dimethoxyethane (DME) followed by reduction using sodium borohydride. Standard workup gives the C-6 thio analog of fumagillin.

EXAMPLES

General

LCMS Methods

LCMS data was collected on an Agilent 1200 Series LC/MSD-SL system equipped with 1100/1200 diode array detector and C18 Luna 2.5 μm 100×3.0 mm column. Mobile Phase A: 0.1% formic acid in water; Mobile Phase B: 0.1% formic acid in 98% aqueous MeCN. A 1 ml/min linear gradient of 10-90% mobile phase B with a column temperature of 45° C. was used for separation. Detection was performed at 254 nm and 215 nm. Method A: gradient time 10 minutes, Method B: gradient time 12 minutes, Method C: gradient time 15 minutes.

Example 1

Procedure for the Preparation of Fumagillol

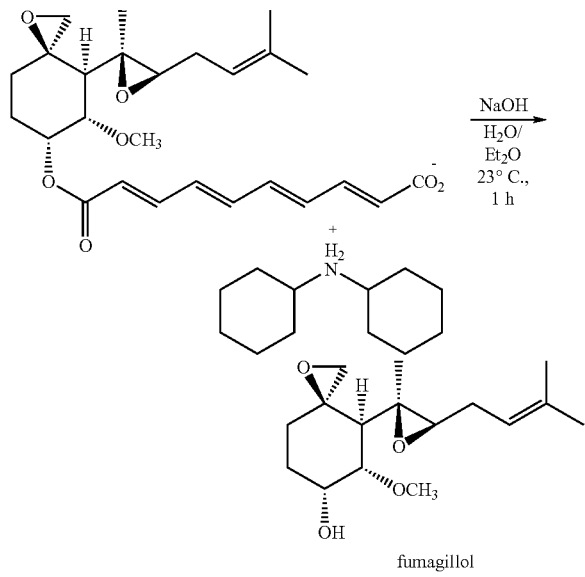

fumagillol

Fumagillin dicyclohexylammonium salt (15.0 g, 23.4 mmol) was suspended in Et$_2$O (300 ml) and vigorously stirred. To the vigorously stirring suspension was added a 0.5 N aqueous solution of NaOH (300 ml) over 15 min. The resulting biphasic reaction mixture was stirred vigorously at 23° C. for 1 h after which it was diluted with Et$_2$O (500 ml) and water (500 ml) and the organic layer separated. The aqueous layer was washed with Et$_2$O (2×100 ml), and the combined organic layers were washed with an aqueous saturated solution of NaCl, dried with MgSO$_4$, and concentrated in vacuo to yield an orange oil. Purification through silica gel chromatography (120 g: 0→100%, EtOAc in hexanes, 35 min.) delivered fumagillol (4.68 g, 16.6 mmol, 71%) as an orange oil or solid. LC/MS method A: m/z 283 [M+H]$^+$, R$_t$ 9.7 min.

Example 2

Synthesis of Compound BB

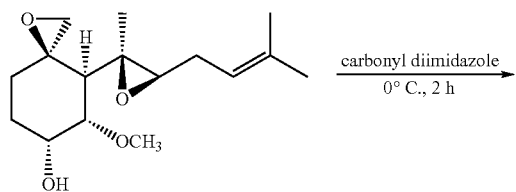

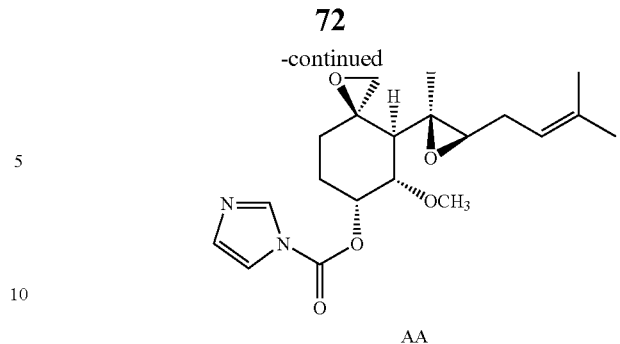

AA

Carbonyl diimidazole (45.7 g, 282 mmol) was suspended in CH$_2$Cl$_2$ (469 ml) and cooled to 0° C. with vigorous stirring. Using a pressure equalizing addition funnel, a solution of fumagillol (26.5 g, 94.0 mmol) in CH$_2$Cl$_2$ (100 ml) was added over 30 min. while maintaining a reaction temperature of 0° C. The mixture was allowed to stir at 0° C. for an additional 2 h after which it was quenched through slow addition of water (100 ml, 1 h) to the cooled reaction mixture. Careful attention was paid to maintain the crude mixture at 0° C. during the exothermic process of water addition. The organic layer was washed with water (3×100 ml) and the combined aqueous layers were washed with CH$_2$Cl$_2$. The combined organic layers were dried with MgSO$_4$ and concentrated in vacuo to yield compound AA (38.5 g, 102 mmol, >98%) as viscous brown oil which was used in subsequent coupling reactions without purification. LC/MS method B: m/z 377 [M+H]$^+$, R$_t$ 5.9 min.

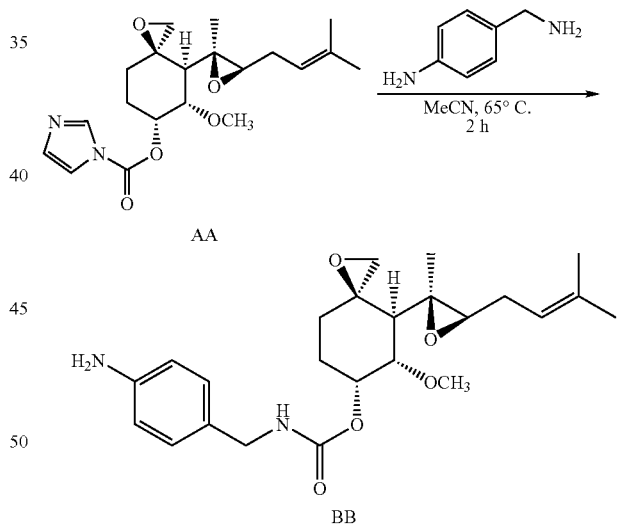

BB

To a stirring solution of Compound AA (10.2 g, 27.2 mmol) in MeCN (175 ml) was added 4-aminobenzylamine (3.32 g, 27.2 mmol) and the solution heated to 65° C. for 2 h. The solution was then allowed to cool to 23° C. and concentrated in vacuo to yield a viscous orange oil. Purification through silica gel chromatography (80 g: 0→100% EtOAc in hexanes, 30 min) delivered BB as a white solid (7.50 g, 17.4 mmol, 64%). LC/MS method B: m/z 453 [M+Na]$^+$, R$_t$ 4.75 min. $^1$H NMR (400 MHz): δ 7.07 (d, 2H); 6.63 (d, 2H); 5.51 (br s, 1H, NH); 5.19 (dd, 1H); 5.01-4.99 (m, 1H); 4.27 (dd, 1H); 4.17 (dd, 1H), 4.14 (dd, 1H); 3.68 (br s, 2H, NH$_2$); 3.64 (dd, 1H); 3.45 (s, 3H); 2.96 (d, 1H); 2.54 (d, 1H); 2.53 (d, 1H); 2.38-

2.31 (m, 1H); 2.19-2.12 (m, 1H); 2.08-1.99 (m, 2H); 1.91 (d, 1H); 1.85-1.75 (m, 1H); 1.73 (s, 3H); 1.64 (s, 3H); 1.20 (s, 3H); 1.06-1.02 (m, 1H).

Example 3

Synthesis of Compound CC

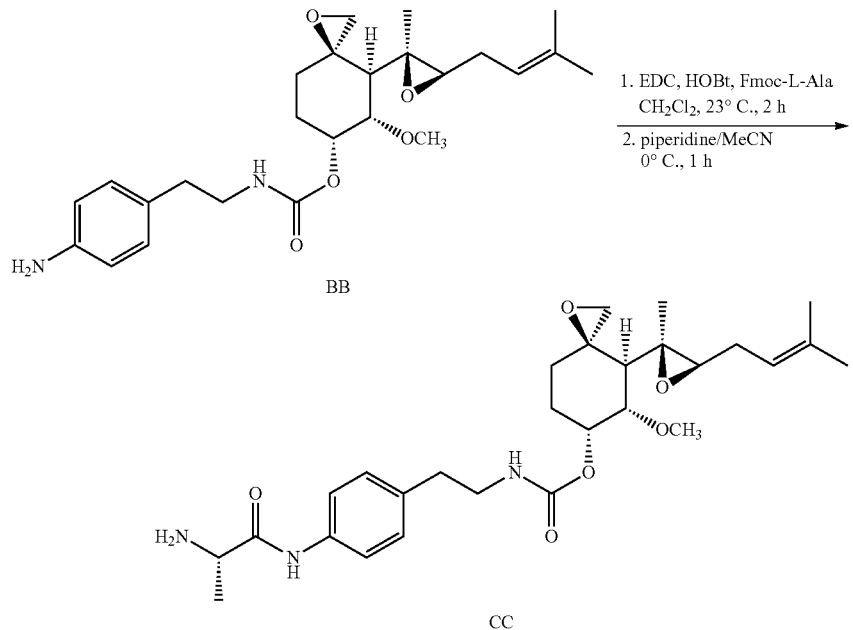

Fmoc-L-Ala (15.4 g, 49.5 mmol), EDC (9.49 g, 49.5 mmol), and HOBt (7.58 g, 49.5 mmol) were taken up in CH$_2$Cl$_2$ (225 ml) and stirred at 23° C. To the suspension was added a solution of compound BB (20.0 g, 45.0 mmol) in CH$_2$Cl$_2$ (50 ml). The reaction mixture was allowed to stir at 23° C. for 3 h after which it was quenched through addition of an aqueous 10% solution of citric acid (100 ml). The organic layer was separated and the aqueous layer washed with CH$_2$Cl$_2$ (3×100 ml). The combined organic layers were washed sequentially with an aqueous 10% solution of citric acid, an aqueous saturated solution of NaHCO$_3$, and an aqueous saturated solution of NaCl. The organic layers were dried with MgSO$_4$ and concentrated in vacuo to yield a white solid. Purification through silica gel chromatography (330 g: 0→75% EtOAc in hexanes, 45 min) delivered the Fmoc-protected derivative of compound CC as a white solid (8.64 g, 11.7 mmol, 42%). LC/MS method B: m/z 760 [M+Na]$^+$, R$_t$ 10.0 min.

The Fmoc-protected derivative of compound CC (8.50 g, 11.5 mmol was dissolved in MeCN (115 ml) and the solution was cooled to 0° C. To the solution was added piperidine (11.4 ml, 115 mmol) and the reaction was allowed to stir at 0° C. for 1 h. Concentration of the reaction mixture in vacuo yielded a white solid. Purification through silica gel chromatography (330 g: 0→20% MeOH (0.5% Et$_3$N) in CH$_2$Cl$_2$ (0.5% Et$_3$N), 45 min) delivered compound CC as white solid (2.73 g, 5.30 mmol, 46%). $^1$H NMR (400 MHz): δ 9.43 (br s, 1H, NH), 7.53 (d, 2H), 7.22 (d, 2H), 5.47 (br s, 1H, NH), 5.20 (dd, 1H), 4.78 (dd, 1H), 3.64-3.58 (m, 2H), 3.44 (s, 3H), 3.44-3.38 (m, 2H), 2.96 (d, 1H), 2.77 (dd, 2H), 2.57-2.52 (m, 2H), 2.40 (ddd, 1H), 2.16 (ddd, 1H), 2.06-1.99 (m, 2H), 1.90 (d, 1H), 1.84-1.80 (m, 1H), 1.74 (s, 3H), 1.65 (s, 3H), 1.42 (d, 3H), 1.20 (s, 3H), 1.14-1.03 (m, 1H). LC/MS method B: m/z 516 [M+H]$^+$, R$_t$ 4.4 min.

Example 4

Synthesis of Compound DD

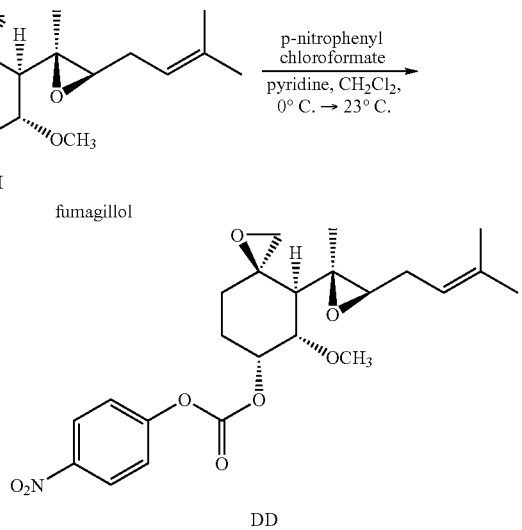

Fumagillol (10.0 g, 35.4 mmol) was dissolved in CH₂Cl₂ (120 ml). Pyridine was added (8.59 ml, 106 mmol) and the solution was cooled to 0° C. with constant stirring. To the stirring solution at 0° C., p-nitrophenyl chloroformate (9.77 g, 46.0 mmol) in CH₂Cl₂ (55 ml) was added dropwise and in portions over 1.5 h after which the reaction mixture was allowed to stir an additional 30 min. at 0° C. Thereafter, the suspension was diluted with EtOAc and washed sequentially with an aqueous 10% solution of citric acid (3×150 ml, 100 ml, 50 ml), water, and an aqueous saturated solution of NaCl. The organic layers were dried with MgSO₄ and concentrated in vacuo to yield tan solid. Purification through silica gel chromatography (330 g: 10→30% EtOAc in hexanes, 45 min) delivered fumagillol p-nitrophenyl carbonate Compound DD (12.3 mg, 27.6 mmol, 78%) as white solid. LC/MS method C: m/z 448 [M+H]⁺, $R_t$ 18.4 min.

Example 5

Synthesis of Compound EE

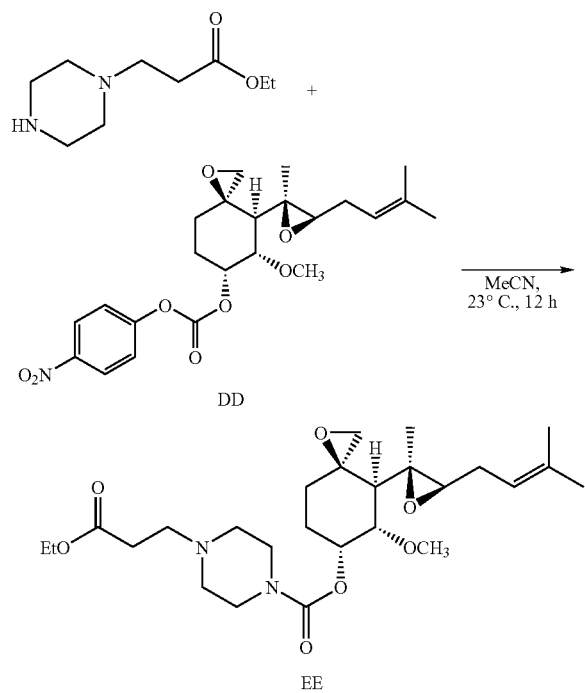

To a stirring suspension of compound DD (100 mg, 0.223 mmol) was added a solution of 3-(piperazin-1-yl)propionic acid ethyl ester (41.6 mg, 0.223 mmol) in MeCN (1 ml), and the solution was allowed to stir 12 h at 23° C. The reaction mixture was diluted with CH₂Cl₂ (50 ml), washed with a 0.5 M aqueous solution of NaOH, dried with MgSO₄, and concentrated in vacuo to yield yellow oil. Purification through silica gel chromatography (12 g: 0→20% MeOH in CH₂Cl₂, 20 min.) delivered Compound EE (42.5 mg, 0.086 mmol, 38%) as a colorless oil. LC/MS method C: m/z 495 [M+H]⁺, $R_t$ 10.5 min.

Example 6

Procedure for the Preparation of Fumagillone

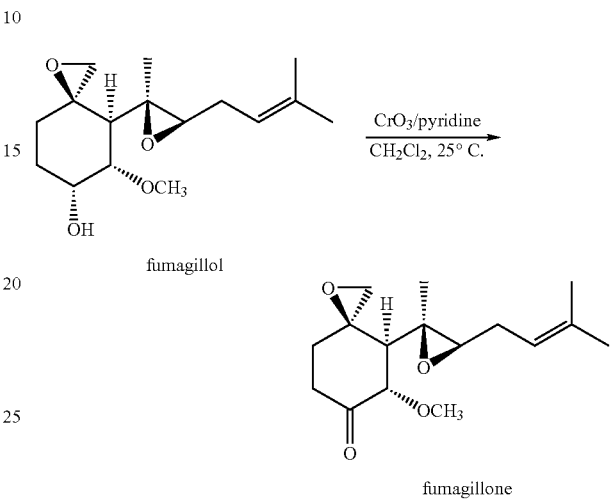

Chromium (VI) oxide (6.37 g, 63.7 mmol) was added to a stirred solution of pyridine (15 ml, 185 mmol) in CH₂Cl₂ (70 ml) in several portions causing an immediate color change to yellow before turning a deep red color. The slurry was stirred for 10 min at 0° C. then at 25° C. for 20 min, during which time most of the solids had dissolved. Fumagillol (3.00 g, 10.6 mmol) in CH₂Cl₂ (20.0 ml) was then added to the mixture causing an immediate color change to dull brown with formation of a ppt. After stirring overnight at 25° C., the solution was decanted into a beaker and the tarry residue rinsed with diethyl ether (200 ml). The combined organics were washed with 1 N aq. NaOH (50 ml), 10% aqueous citric acid (2×50 ml) and brine (50 ml). The organic extract was dried over MgSO₄, filtered and concentrated in vacuo to provide 3.8 g of the crude product as a yellow oil. Purification by chromatography on silica gel (40 g) eluting with an ethyl acetate/hexane gradient (0->30%, 5 min; 30%, 5 min; 30->40%, 5 min; 40%, 10 min; 40-50%, 3 min) provided 2.297 g (77%) of the desired product as a yellow oil. LC/MS Method B: m/z 281 [M+H]+, $R_t$ 8.40 min.

Example 7

Procedure for the Preparation of Fumagillamine

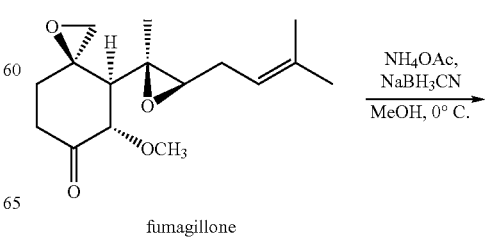

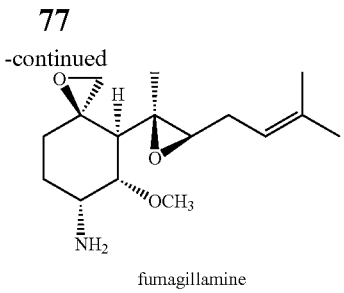

fumagillamine

To a solution of fumagillone (903 mg, 3.07 mmol) in anhydrous MeOH (20.0 ml) cooled to 0° C. was added ammonium acetate (2.49 g, 31.3 mmol) and sodium cyanoborohydride (254 mg, 3.84 mmol). The resultant yellow solution was stirred at 0° C. After 3 h, the reaction was concentrated in vacuo to a light yellow liquid which was diluted with EtOAc and washed with sat. aq. NaHCO$_3$ (10 ml). The aq. layer was salted with solid NaCl and back extracted with EtOAc (4×25 ml). The combined organic extracts were dried (MgSO$_4$), filtered and concentrated in vacuo to provide 1.047 g of a light yellow powder that was used immediately in the next step without purification.

Example 8

Synthesis of Compound FF

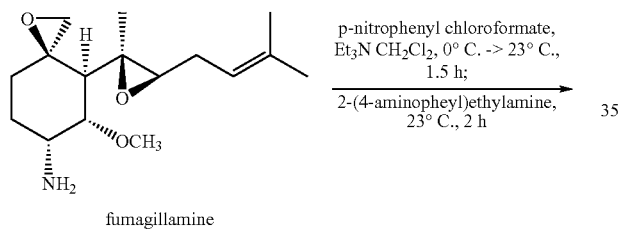

fumagillamine

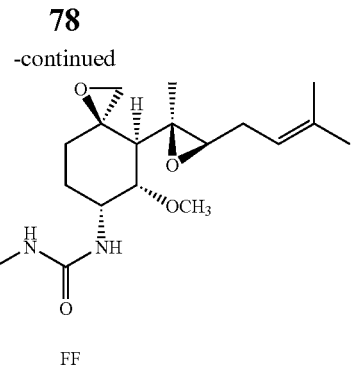

FF

To a stirring solution of fumagillamine (1.00 g, 3.55 mmol) in CH$_2$Cl$_2$ (15 ml) at 0° C. was added Et$_3$N (0.545 ml, 3.91 mmol) followed by a solution of p-nitrophenyl chloroformate (0.788 g, 3.91 mmol) in CH$_2$Cl$_2$ (2 ml). The reaction mixture was allowed to warm to 23° C. over 1.5 h after which a solution of 2-(4-aminophenyl)ethylamine (0.458 ml, 3.55 mmol) in CH$_2$Cl$_2$ (2 ml) was added and the mixture allowed to stir at 23° C. for an additional 2 h. The reaction mixture was diluted with CH$_2$Cl$_2$, washed with an aqueous saturated solution of NaHCO$_3$, dried over MgSO$_4$, and concentrated in vacuo to yield yellow solid. Purification through silica gel chromatography (12 g: 0→5% MeOH (0.05% Et$_3$N) in CH$_2$Cl$_2$ (0.05% Et$_3$N), 26 min) delivered Compound FF (0.890 g, 2.00 mmol, 57%) as light yellow solid. LC/MS method A: m/z 444 [M+H]$^+$, R$_t$ 4.1 min.

Example 9

Synthesis of Compound GG

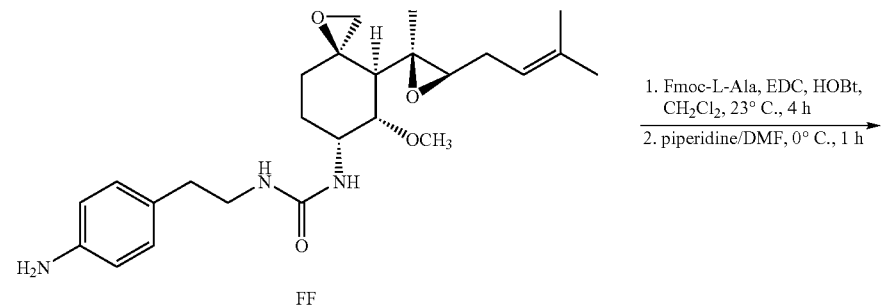

FF

-continued

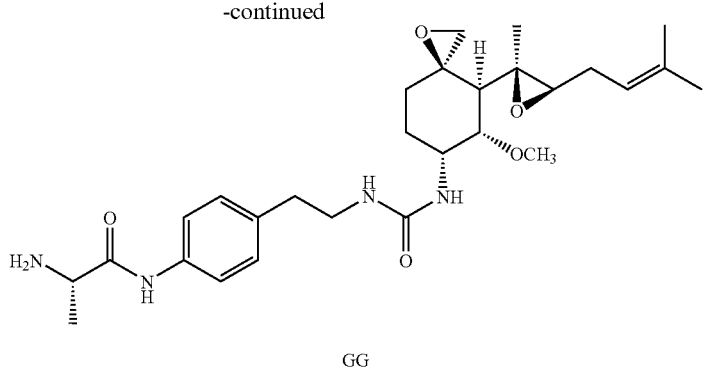

GG

Compound FF (0.890 g, 2.01 mmol), Fmoc-L-Ala monohydrate (0.687 g, 2.21 mmol), HOBt (0.338 g, 2.21), and EDC (0.423 g, 2.21 mmol) were dissolved in $CH_2Cl_2$ (5 ml) and allowed to stir at 23° C. for 4 h. The reaction mixture was quenched through addition of an aqueous 10% solution of citric acid (5 ml) and the aqueous layer was washed with $CH_2Cl_2$ (2×10 ml). The combined organic layers were washed sequentially with an aqueous 10% solution of citric acid (20 ml), an aqueous saturated solution $NaHCO_3$, and an aqueous saturated solution of NaCl, after which they were dried with $MgSO_4$ and concentrated in vacuo to yield yellow oil. Purification through silica gel chromatography (12 g: 0→5% MeOH in $CH_2Cl_2$, 26 min) delivered the Fmoc-protected derivative of Compound GG (0.634 g, 0.860 mmol, 43%) as white solid. LC/MS method A: m/z 737 $[M+H]^+$, $R_t$ 8.1 min.

The Fmoc-protected derivative of Compound GG (0.634 g, 0.860 mmol) was dissolved in DMF (5 ml) and the solution cooled to 0° C. To the stirring solution was added piperidine (0.852 ml, 8.60 mmol) and the mixture was allowed to stir at 0° C. for 1 h after which it was concentrated in vacuo to yield white solid. Purification through silica gel chromatography (4 g: 0→50% MeOH (0.5% $Et_3N$) in $CH_2Cl_2$ (0.5% $Et_3N$), 30 min) delivered Compound GG (0.336 g, 0.653 mmol, 76%) as white solid. LC/MS method A: m/z 515 $[M+H]^+$, $R_t$ 3.9 min.

Example 10

Synthesis of Compound JJ

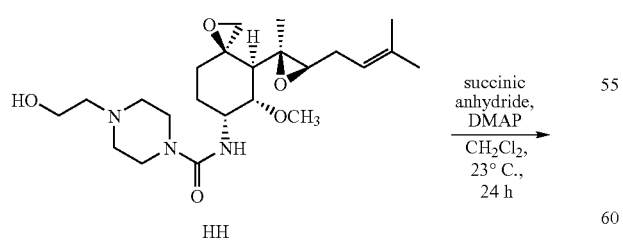

HH

-continued

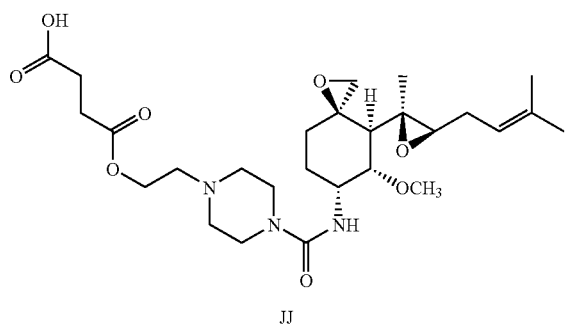

JJ

Compound HH (0.459 g, 1.05 mmol), which was prepared in a procedure analogous to that of compound FF, described above, was dissolved in $CH_2Cl_2$ (10.5 ml) and succinic anhydride (0.105 g, 1.05 mmol) was added followed by DMAP (0.013 g, 0.105 mmol). The mixture was allowed to stir at 23° C. for 24 h after which additional succinic anhydride was added (0.105 g, 1.05 mmol) and the mixture was allowed to stir an additional 1 h at 23° C. The reaction mixture was concentrated in vacuo to yield Compound JJ (0.564 g, 1.05 mmol, >98%) as a pale yellow oil which was used in subsequent coupling reactions without purification. LC/MS method A: m/z 538 $[M+H]^+$, $R_t$ 3.7 min.

Example 11

Representative Procedure

Preparation of Conjugate 12: (By Using the Appropriate Starting Materials/Reactants, Conjugates 3, 6, 11, 15, 16, 24, 25, 26, 27, 28, 33, 37 and 43 can be Prepared in an Analogous Manner)

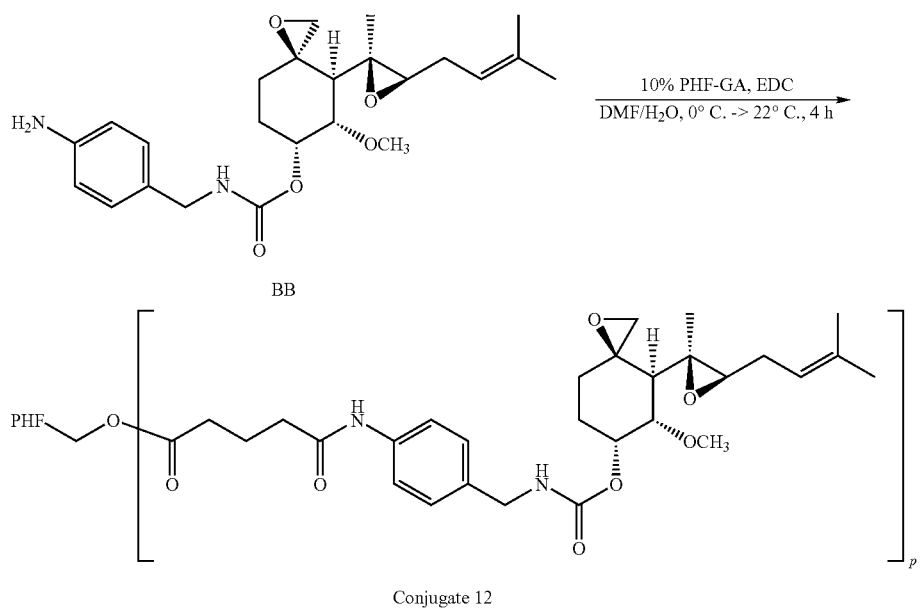

Conjugate 12 wherein p=m, and m is as defined above for Formula I.

PHF-GA (11.4 g, 78.0 mmol) was dissolved in a solution of 20% DMF in water (114 ml). To the stirring mixture at 23° C. was added a solution of Compound BB (1.02 g, 2.72 mmol) in DMF (20 ml) and the pH adjusted to 5.9-6.0. The reaction mixture was cooled to 0° C. with constant stirring after which EDC (1.04 g, 5.44 mmol) was added in three portions over 30 minute intervals. Upon addition of the last portion of EDC, stirring was continued for 2.5-4.0 h at 0° C. The pH was adjusted to 4.5-5.0 using 1.0 N HCl and the mixture filtered through a 0.2µ membrane and purified by size exclusion chromatography. Fractions that contained desired product were collected and the resulting solution was lyophilized to yield Conjugate 12 as white solid (12.6 g). $^1$H NMR indicated a loading of 8.0% (w/w) of BB.

Example 12

Representative Procedure

Preparation of Conjugate 4. (By Using the Appropriate Starting Materials/Reactants, Conjugates 5, 10, 14 and 41 can be Prepared in an Analogous Manner)

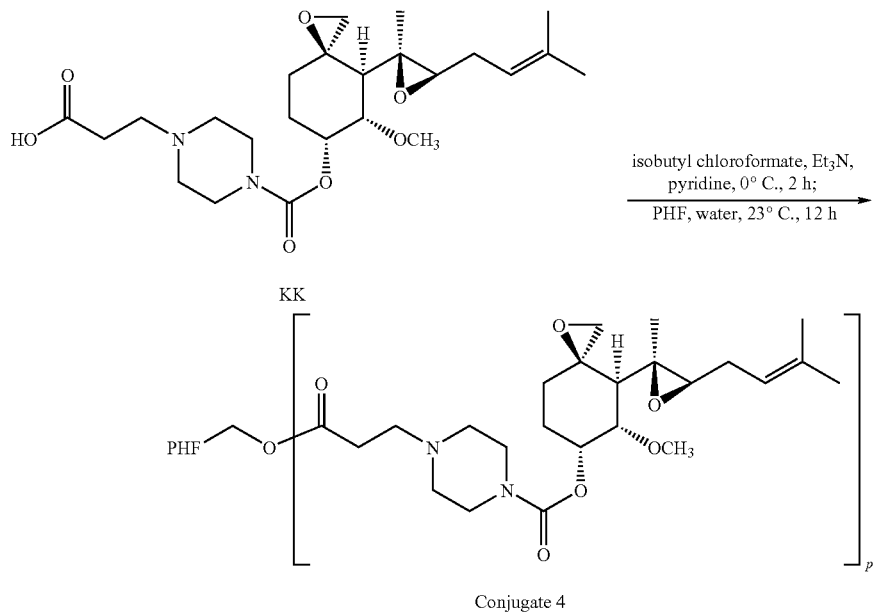

Conjugate 4 wherein p=m as defined above for Formula I.

Compound KK (200 mg, 0.429 mmol) was dissolved in THF (15 ml) and cooled to 0° C. Et$_3$N (0.119 ml, 0.857 mmol)

was added followed by isobutyl chloroformate (0.051 ml, 0.386 mmol) and the mixture was allowed to stir 2 h at 0° C. In a separate vessel, PHF (579 mg, 4.29 mmol) was dissolved in anhydrous pyridine. The two solutions were combined and allowed to stir and warm to 23° C. over 12 h. The crude reaction mixture was concentrated in vacuo and diluted with 100 ml water. The mixture was filtered through a 0.2μ membrane and purified by size exclusion. Fractions that contained desired product were collected and the resulting solution was lyophilized to yield conjugate 4 as white solid (550 mg). $^1$H NMR indicated a loading of 5.0% (w/w) of KK.

Example 13

Synthesis of Compound LL

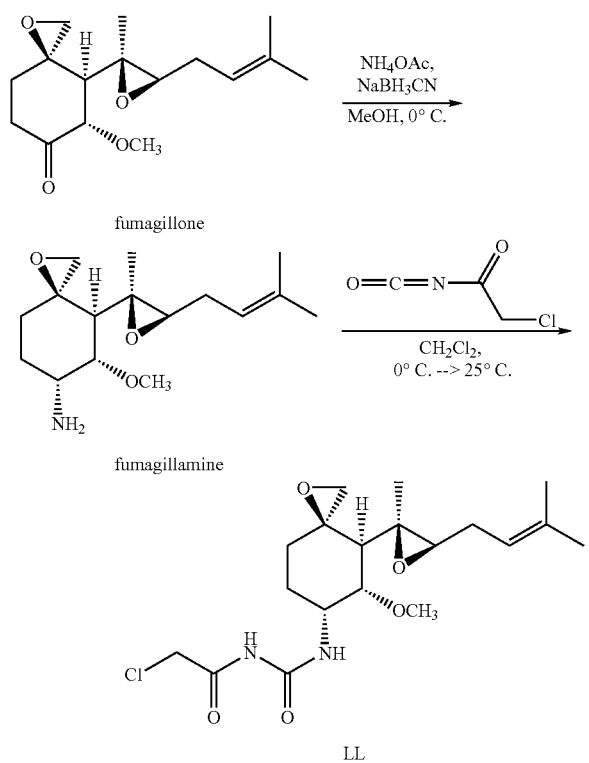

To a solution of fumagillone (6.0 g, 21.4 mmol) in anhydrous MeOH (150 ml) cooled to 0° C. was added ammonium acetate (17.0 g, 214 mmol) and sodium cyanoborohydride (2831 mg, 42.8 mmol) forming a light yellow solution that was stirred at 0° C. After 1 h 40 min, another portion of sodium cyanoborohydride (500 mg, 7.56 mmol) was added to the reaction. Stirring was continued for a total of 2.5 h at 0° C. followed by warming to 25° C. over 15 min. This was followed by dilution with EtOAc (100 ml), concentration in vacuo to remove MeOH, adding additional EtOAc (100 ml) and washing with sat aq. NaHCO$_3$ (50 ml). The aqueous layer was salted with NaCl (s) then back extracted with EtOAc (3×70 ml). The combined organic extracts were dried (MgSO$_4$), filtered and concentrated in vacuo to provide 6.153 g of a light-yellow solid. The solid was taken up in CH$_2$Cl$_2$ (130 ml) and cooled to 0° C. followed by addition of chloroacetylisocyanate (3.60 ml, 42 mmol) forming a yellow solution which was allowed to warm slowly to 25° C. After overnight stirring, the reaction was diluted with sat aq. NH$_4$Cl (50 ml), stirred vigorously for 10 min, then diluted with additional EtOAc (100 ml) and concentrated in vacuo to remove CH$_2$Cl$_2$. The layers were separated and the aqueous layer was salted with NaCl (s) then back extracted with EtOAc (2×70 ml). The combined organic extracts were washed with brine (30 ml), dried (MgSO$_4$), filtered and concentrated in vacuo to provide an off-white solid. Purification by chromatography on silica gel (120 g) eluting with an EtOAc/hexane gradient [0->30%, 7 min; 30%, 7 min; 30->50%, 7 min; 50%, 10 min; 50->100%, 5 min; 100%, 3 min] provided 4.17 g (49%) of the desired product as a white solid. LC/MS Method B: m/z 282 [M-C=ONHC=OCH$_2$Cl]$^+$, R$_t$ 7.36 min.

Example 14

Synthesis of Compound MM

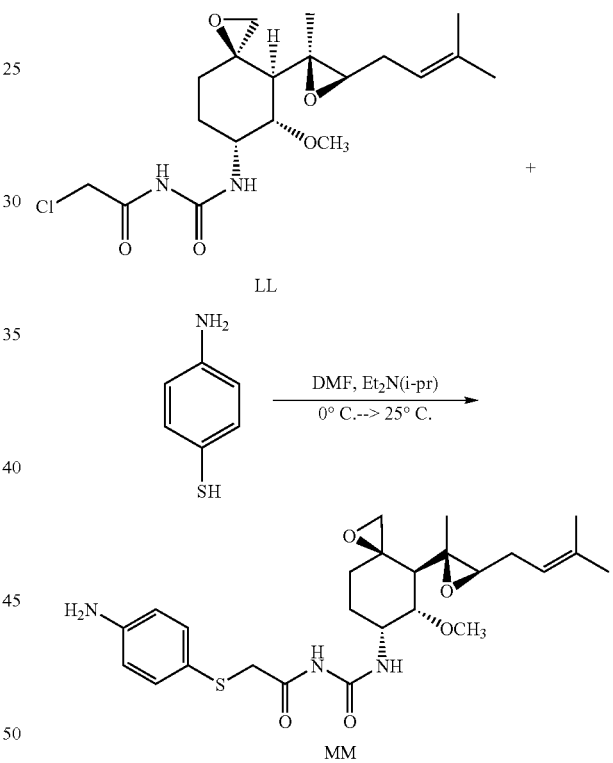

To a solution of the alkyl chloride (3810 mg, 9.50 mmol) in anhydrous DMF (70 ml) cooled to 0° C. and under inert atmosphere was added Hunig's base (2.00 ml, 11.40 mmol) followed by 4-aminothiophenol (1360 mg, 10.45 mmol), generating a clear, yellow solution. Stirring was maintained at 0° C. for 1.5 h, then at 25° C. for 15 min. The solution was then diluted with EtOAc (100 ml) and H$_2$O (70 ml), layers separated, and aqueous layer extracted further with EtOAc (2×100 ml). The combined organic extracts were washed with brine (25 ml), dried, filtered and concentrate in vacuo to yield a thick, yellow oil. Purification by chromatography on silica gel (120 g) eluting with an EtOAc/hexane gradient [0->40%, 5 min; 40%, 4 min; 40->60%, 4 min; 60%, 10 min; 60->80%, 3 min; 80%, 5 min; 80-100%, 3 min] provided 2.05 g (44%) of MM. LC/MS Method B: m/z 490 [M+H]+, $R_t$ 7.134 min.

Example 15

Synthesis of Compound NN

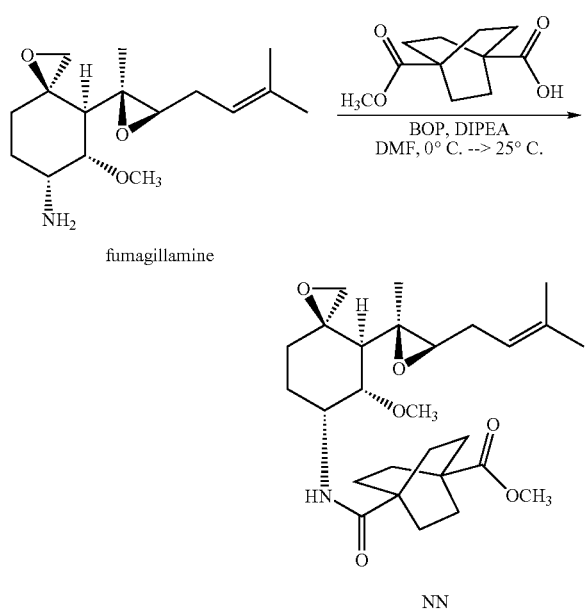

fumagillamine

NN

To a solution of the carboxylic acid (607 mg, 2.86 mmol) in anhydrous DMF (13.0 ml), under inert atmosphere, was added di-isopropylethylamine (DIPEA) (1.50 ml, 8.61 mmol) followed by benzotriazole-1-yl-oxy-tris-(dimethylamino)-phosphonium hexafluorophosphate (BOP) (1.44 g, 3.12 mmol). The resultant clear solution was stirred at 25° C. for 5 min, then cooled to 0° C. followed by addition of fumagillamine (875 mg, 3.11 mmol, freshly prepared from fumagillone and used without further purification) in DMF (3.0 ml), generating a yellow solution. The solution was stirred at 0° C. and allowed to warm slowly to 25° C. overnight. After 14 h, the reaction was diluted with EtOAc and water (25 ml each), layers separated and the aqueous layer extracted with additional EtOAc (2×50 ml). The combined organic extracts were washed with water (2×15 ml), sat aq. NaHCO$_3$ and brine (15 ml each), dried (MgSO4), filtered and concentrated in vacuo to provide an orange-yellow oil. Purification by chromatography on silica gel (40 g) eluting with an EtOAc/hexane gradient [0->30%, 5 min; 30%, 4 min; 30->50%, 4 min; 50%, 5 min; 50->80%, 3 min] provided 924 mg (69%) of NN as a light yellow oil. LC/MS Method B: m/z 476 [M+H]+, $R_t$ 9.85 min.

Example 16

Synthesis of Compound OO

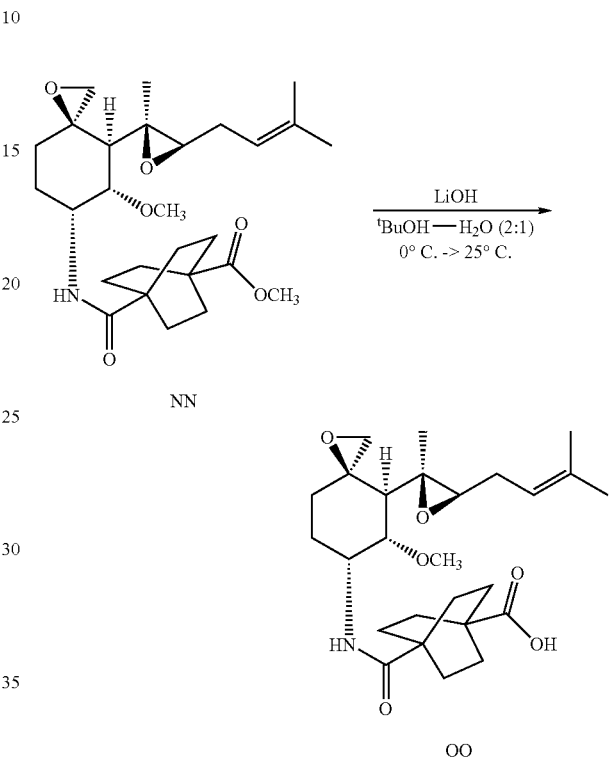

OO

To a solution of the methyl ester (1.2 g, 2.52 mmol) in tert-butanol (16.0 ml) and water (8.0 ml) cooled to 0° C. was added LiOH (215 mg, 5.12 mmol), in one portion, forming a slurry. After 30 min, the reaction mixture had thickened and become opaque. The reaction mixture was allowed to warm slowly to 25° C. overnight. After 22 h, the reaction was quenched by addition of 1.0 M NaHSO$_4$ (7.0 ml, 7.0 mmol) to pH 4. The volatiles were then removed in vacuo, leaving a few milliliters of opaque liquid, which was diluted with water (25 ml) and EtOAc (50 ml) and layers separated. The aqueous layer was salted with NaCl (s) and extracted further with EtOAc (2×50 ml). The combined organic extracts were dried (MgSO$_4$), filtered and concentrated in vacuo to provide 1.38 g of OO as yellow oil. Purification by chromatography on silica gel (40 g) eluting with a MeOH/CH$_2$Cl$_2$ gradient [2%, 5 min; 2->10%, 10 min] provided 943 mg (81%) of the OO as white solid. LC/MS Method B: m/z 462 [M+H]+, R$_t$ 7.76 min.

Example 17

Synthesis of Compound PP

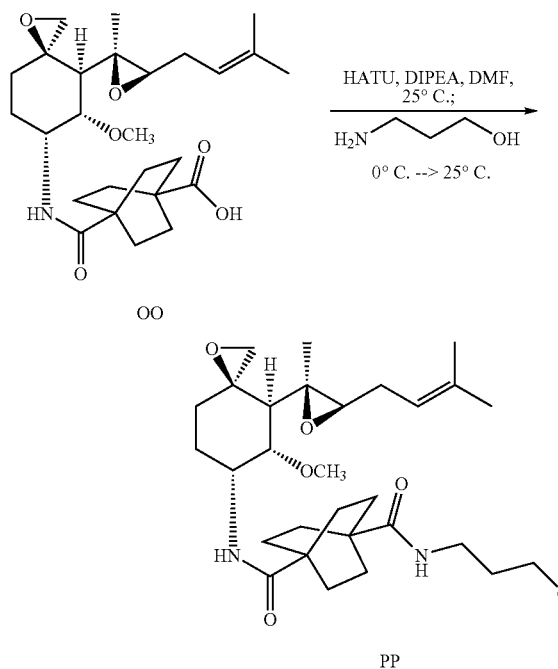

To a solution of the carboxylic acid OO (440 mg, 0.953 mmol) in anhydrous DMF (4.0 ml) was added diisopropylethyl amine (500 μL, 2.86 mmol) and HATU (448 mg, 1.144 mmol) at 25° C. under inert atmosphere. The resultant yellow solution was stirred at 25° C. for 10 min, then cooled to 0° C. for addition of 3-amino-1-propanol (80 μL, 1.050 mmol), causing the solution to become bright yellow. The solution was stirred at 0° C. for 10 min then warmed to 25° C. and stirring continued. After 2 h, the reaction was diluted with EtOAc and H$_2$O (10 ml each), layers separated and aqueous layer extracted with EtOAc (2×20 ml). The combined organic extracts were dried (MgSO$_4$), filtered and concentrated in vacuo to an orange oil. Purification by chromatography on silica gel (12 g) eluting with a MeOH/EtOAc gradient [0%, 1 min; 0->5%, 1 min; 5%, 3 min; 5-10%, 10 min] provided 411 mg (83%) of the desired product PP as yellow oil. LC/MS Method B: m/z 519 [M+H]+, R$_t$ 6.76 min.

Example 18

Synthesis of Compound QQ

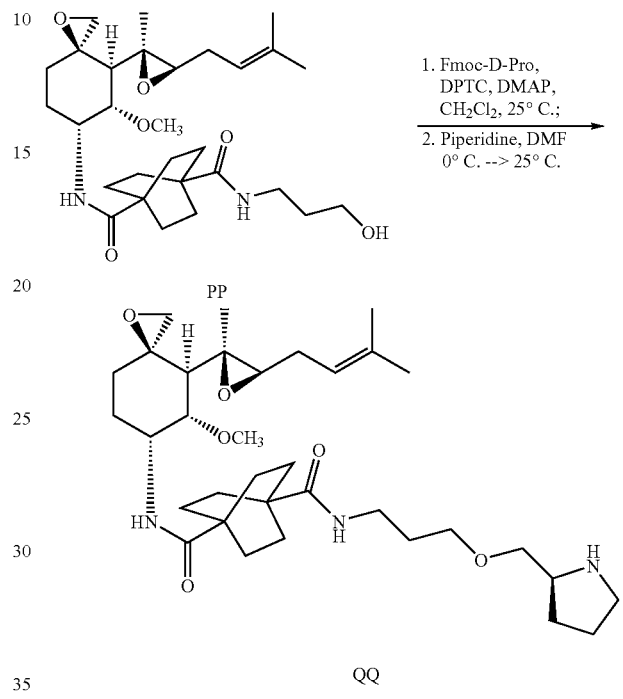

To a solution of the alcohol PP (404 mg, 0.779 mmol) in CH$_2$Cl$_2$ (5.0 ml) was added the Fmoc-D-Proline amino acid (312 mg, 0.925 mmol), in one portion, and DMAP (27 mg, 0.221 mmol), forming a clear solution. To this was added di-2-(pyridyl)thiocarbonate (DPTC) (366 mg, 1.542 mmol) and the resultant orange solution was stirred at 25° C. under inert atmosphere. After 2 min, the solution became a deep orange-red color. After 2.5 h, an additional portion of DPTC (50 mg, 0.211 mmol) was added to the reaction. After 5.5 h, the reaction was diluted with EtOAc and H$_2$O (10 ml each), layers separated, and the aqueous layer extracted with EtOAc (2×20 ml). The combined organic extracts were washed with sat aq. NaHCO$_3$ and brine (10 ml each), dried, filtered and concentrated in vacuo to provide an orange-brown oil. Purification by chromatography on silica gel (12 g) eluting with an EtOAc/hexane gradient [0->50%, 5 min; 50%, 5 min; 50->100%, 5 min] provided 431 mg (67%) of the desired Fmoc-protected derivative of QQ as a dark yellow oil. LC/MS Method B: m/z 838 [M+H]+, R$_t$ 10.19 min.

Fmoc-protected QQ (277 mg, 0.331 mmol) was dissolved in DMF (1.30 ml) and the solution cooled to 0° C. To the stirring solution was added piperidine (0.330 ml, 3.34 mmol) and the solution stirred at 0° C. A precipitate formed after 20 min. After 4 h, the solids were filtered off on a frit, rinsed with methanol and the filtrate concentrated in vacuo to provide a white solid. Purification by chromatography on silica gel (4 g) eluting with a gradient of MeOH/CH$_2$Cl$_2$+0.5% Et$_3$N [0->50%, 30 min] provided 185 mg (91%) of Compound QQ as a yellow oil. LC/MS Method B: m/z 616 [M+H]+, R$_t$ 4.44 min.

Example 19

Representative Procedure

Preparation of Conjugate 19 (By Using the Appropriate Starting Materials/Reactants, Conjugates 1, 2, 7, 8, 9, 13, 17, 18, 19, 20, 21, 22, 23, 30, 34, 35, 36, 39, 40, 42, and 44 can be Prepared in an Analogous Manner)

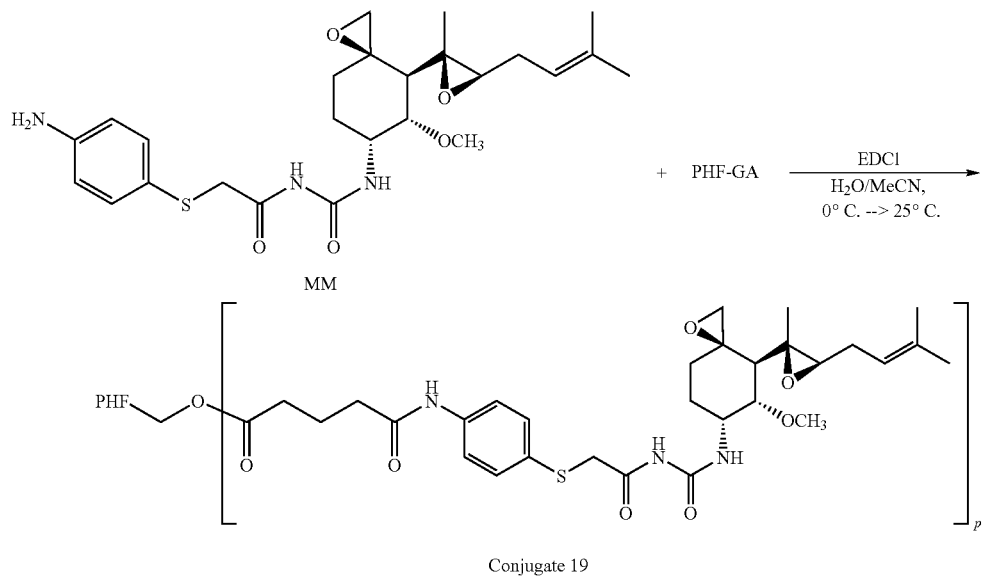

Conjugate 19 where p=m and is as defined above for Formula I.

Water (140 ml) was added to PHF-GA (7.30 g) and the resulting mixture was stirred vigorously for 1 h to yield a yellow solution. The fumagillin derivative MM (852 mg) in MeCN (8.3 ml) was then added at 25° C. Additional MeCN (33.7 ml) was added to make 42 ml total. The solution was cooled to 0° C. followed by addition of EDC (475 mg) portionwise over 5 min after which the pH of the reaction was adjusted to 6.0. After 30 min, the solution was warmed to 25° C. Additional portions of EDC were added at 2 h (200 mg) and 3 h (100 mg). At 4.5 h, the reaction was acidified with 1.0 N HCl to pH 5.0. The reaction was diluted to ~300 ml with water, filtered thru a 0.2μ membrane and purified by size exclusion chromatography. Fractions that contained the desired product cleanly were pooled and lyophilized to provide 6.6 g of conjugate 19 as white solid. UV analysis (254 nm) indicated a 9.8% loading of MM.

Example 20

METAP-2 Inhibition by Fumagillin Core Structure

The test samples were evaluated for their ability to inhibit human MetAP-2 enzyme. The compounds were added at varying concentrations to human MetAP-2 enzyme (6 nM) in a buffered medium containing 20 mM Hepes, pH 7.4, 100 mM KCl, 0.1 mM Co(II), 10% glycerol, 5 mg/ml of L-Amino acid oxidase, 10 mg/ml of peroxidase, 10 mg/ml of o-dianisidine, and 2 mM of Met-Ser-Ala at 37° C. After 10 minutes incubation the reaction is started by adding the substrate Met-Gly-Pro-AMC to 2 mM and the release of AMC is measured with a Decan Plate reader (Excitation at 345 nm, emission at 445 nm). The kinetic data is recorded at 30 sec intervals for 30 min. Table 1 lists some of the conjugates and compounds tested along with their approximate $IC_{50}$ values for inhibiting Met-AP2.

TABLE 1

| Compound or Conjugate | $IC_{50}$ |
|---|---|
| Compound 8 | <10 nM |
| Conjugate 12 | <1000 nM |
| Compound 63 | <10 nM |
| Compound 39 | <10 nM |
| Conjugate 19 | <50 nM |
| Compound 65 | <10 nM |
| Compound 8 | <10 nM |
| Conjugate 15 | <50 nM |
| Compound 60 | <10 nM |
| Compound 61 | <10 nM |
| Compound 51 | <10 nM |
| Conjugate 24 | <50 nM |
| Compound 59 | <10 nM |
| Compound 58 | <10 nM |
| TNP-470* | <10 nM |
| PPI-2458** | <10 nM |

*The chemical structure of TNP-470:

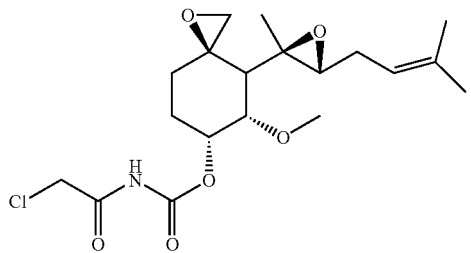

TNP-470

**The chemical structure of PPI-2458 is:

TABLE 1-continued

| Compound or Conjugate | IC$_{50}$ |
|---|---|

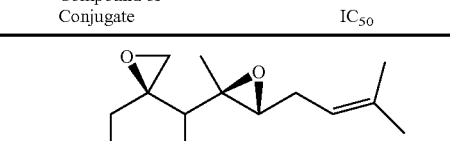

PPI-2458

Example 21

Inhibitory Effect of Fumagillin Conjugates and Analogs on Cell Growth

Using human umbilical vein endothelial cells (HUVECs), the effect of the fumagillin analog conjugates and the fumagillin analogs on cell growth was evaluated.

The HUVECs were added to M199 medium supplemented with 20% FBS, after which the cells were incubated at 37° C. under 5% $CO_2$. 96-well plates were seeded at 5,000 cells/well in a total volume of 100 μL. The cells were left overnight to attach to the plate. Cells were subcultured a maximum of 15 times before being discarded.

To evaluate the inhibitory activity of the fumagillin conjugate or the fumagillin analog alone on the growth of HUVEC cells, the conjugate or fumagillin analog was dissolved in the required amount of 0.9% saline, vortexed briefly to wet and disperse the solids, followed by vortexing for a total of 30 min. 2× stock solutions for each conjugate and fumagillin analog were made ranging from 12 μM to 0.06 μM. The cells were treated with the conjugate solution or fumagillin analog solution at various concentrations ranging from 30 nM to 0.01 nM, and cultured for 5 days at 37° C.

Colorimetry was performed to determine the extent of cell growth by adding 20 μL of MTS/PES reagent to each well, incubation for 4 h at 37° C. followed by measuring the absorbance at 490 nm. Table 2 tabulates the results of the tests performed on some of the conjugates and compounds of the invention and other reference compounds.

TABLE 2

Inhibitory Effect of Fumagillin Conjugates and Analogs on Cell Growth

| Agent | IC$_{50}$ (nM) |
|---|---|
| Conjugate 1 | nd |
| Conjugate 2 | nd |
| Conjugate 3 | nd |
| Conjugate 4 | <25 |
| Conjugate 5 | nd |
| Conjugate 6 | <25 |
| Conjugate 7 | <25 |
| Conjugate 8 | nd |
| Conjugate 9 | nd |
| Conjugate 10 | nd |
| Conjugate 11 | <25 |
| Conjugate 12 | 25-100 |
| Conjugate 13 | 25-100 |
| Conjugate 14 | nd |
| Conjugate 15 | 100-300 |
| Conjugate 16 | >300 |
| Conjugate 17 | nd |
| Conjugate 18 | <25 |
| Conjugate 19 | >300 |
| Conjugate 20 | 100-300 |
| Conjugate 21 | nd |
| Conjugate 22 | >300 |
| Conjugate 23 | >300 |
| Conjugate 24 | 100-300 |
| Conjugate 25 | 25-100 |
| Conjugate 26 | nd |
| Conjugate 27 | nd |
| Conjugate 28 | nd |
| Conjugate 29 | 100-300 |
| Conjugate 30 | >300 |
| Conjugate 31 | <25 |
| Conjugate 32 | <25 |
| Conjugate 33 | >300 |
| Conjugate 34 | >300 |
| Compound 1 | <25 |
| Compound 2 | <25 |
| Compound 3 | <25 |
| Compound 4 | >30 |
| Compound 5 | <25 |
| Compound 6 | <25 |
| Compound 7 | <25 |
| Compound 8 | <25 |
| Compound 9 | <25 |
| Compound 10 | <25 |
| Compound 11 | <25 |
| Compound 12 | <25 |
| Compound 13 | >30 |
| Compound 14 | <25 |
| Compound 15 | >30 |
| Compound 16 | >30 |
| Compound 17 | <25 |
| Compound 18 | <25 |
| Compound 19 | <25 |
| Compound 20 | <25 |
| Compound 21 | <25 |
| Compound 22 | <25 |
| Compound 23 | <25 |
| Compound 24 | <25 |
| Compound 25 | >30 |
| Compound 26 | <25 |
| Compound 27 | <25 |
| Compound 28 | <25 |
| Compound 29 | <25 |
| Compound 30 | <25 |
| Compound 31 | <25 |
| Compound 32 | <25 |
| Compound 33 | >30 |
| Compound 34 | <25 |
| Compound 35 | <25 |
| Compound 36 | <25 |
| Compound 37 | 25-100 |
| Compound 38 | 25-100 |
| Compound 39 | <25 |
| Compound 40 | 25-100 |
| Compound 41 | 100-300 |
| Compound 42 | 100-300 |
| Compound 43 | <25 |
| Compound 44 | <25 |
| Compound 45 | <25 |
| Compound 46 | <25 |
| Compound 47 | <25 |
| Compound 48 | <25 |
| Compound 49 | 100-300 |
| Compound 50 | <25 |
| Compound 51 | <25 |
| Compound 52 | <25 |
| Compound 53 | 25-100 |
| Compound 54 | <25 |
| Compound 55 | <25 |

TABLE 2-continued

Inhibitory Effect of Fumagillin Conjugates and Analogs on Cell Growth

| Agent | IC$_{50}$ (nM) |
|---|---|
| Compound 56 | <25 |
| Compound 57 | <25 | nd = not determined

The structures of the Conjugates tested can be found in the listing of the illustrative conjugates of Formula IV. The structures of the compounds tested in Table 2 are as set forth below:

| Compound No. | Structure |
|---|---|
| 1 | 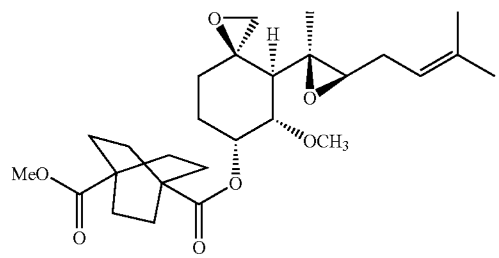 |
| 2 | 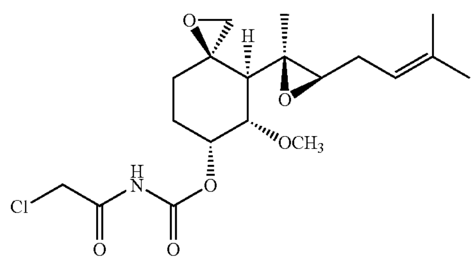 |
| 3 | 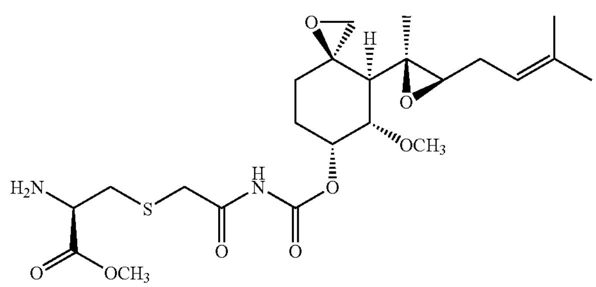 |
| 4 | 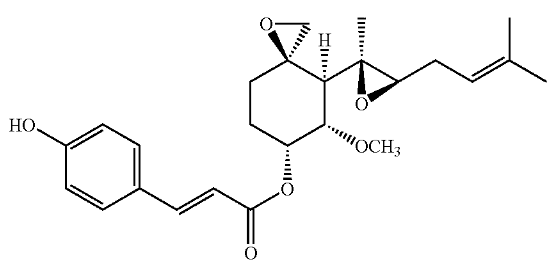 |
| 5 | 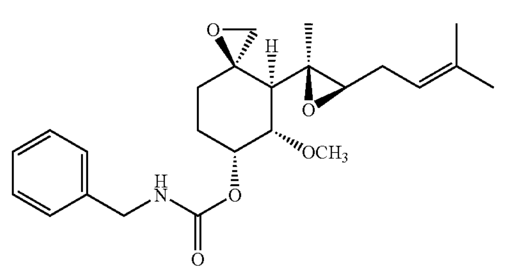 |

-continued
| Compound No. | Structure |
|---|---|
| 6 | 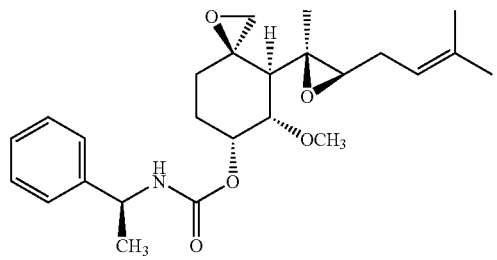 |
| 7 | 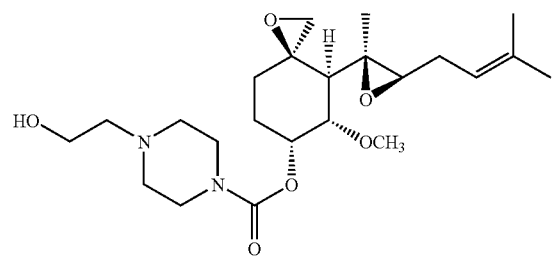 |
| 8 | 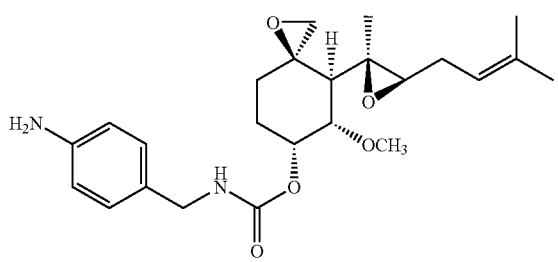 |
| 9 | 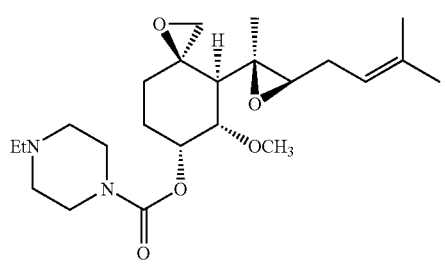 |
| 10 | 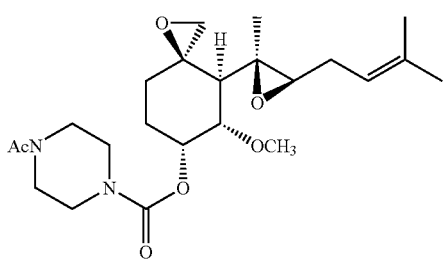 |
| 11 | 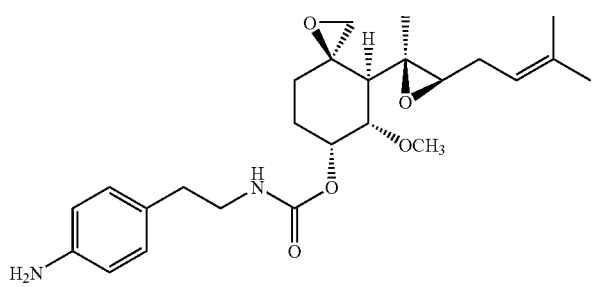 |

| Compound No. | Structure |
|---|---|
| 12 | 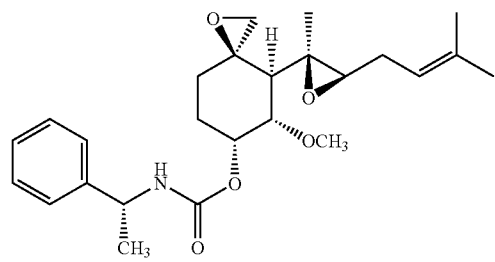 |
| 13 | 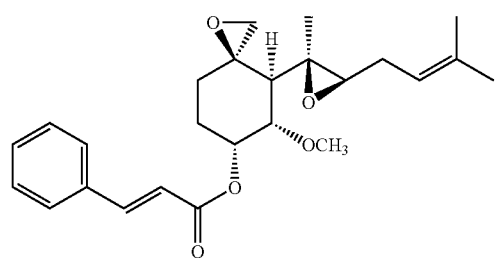 |
| 14 | 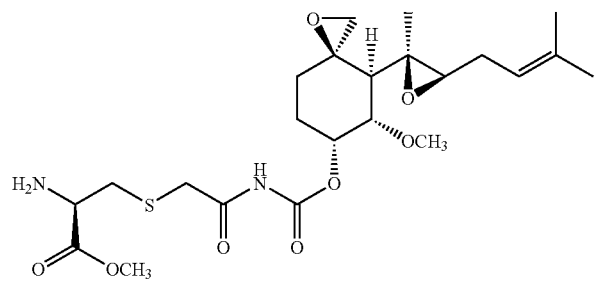 |
| 15 | 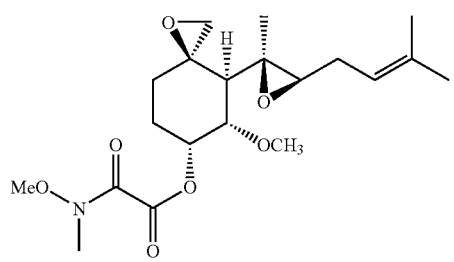 |
| 16 | 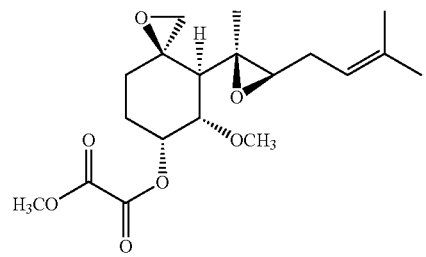 |

-continued

| Compound No. | Structure |
|---|---|
| 17 | (structure: cyclohexane core with spiro epoxide, vinyl epoxide bearing prenyl group, OCH₃, and carbamate linker to 4-acetamidobenzyl group) |
| 18 | (structure: same core with OCH₃, carbamate linker to 4-acetamidophenethyl group) |
| 19 | (structure: same core with OCH₃ and NH-C(=O)- linked to 4-nitrobenzoyl group) |
| 20 | (structure: same core with OCH₃ and ketone (C=O) on ring) |
| 21 | (structure: same core with OCH₃, ester linker to 3,4,5-trimethoxycinnamoyl group) |
| 22 | (structure: same core with OCH₃, carbamate linker to piperazine N-CH₂CH₂C(=O)OEt) |

| Compound No. | Structure |
|---|---|
| 23 | 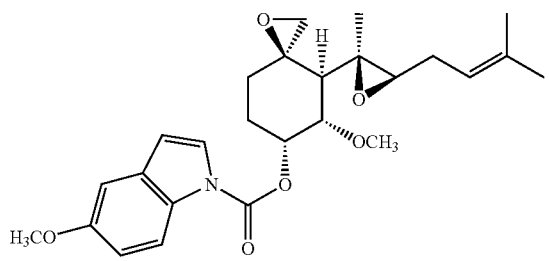 |
| 24 | 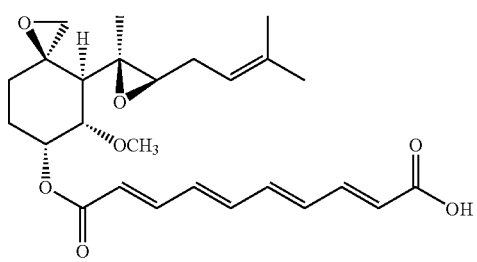 |
| 25 | 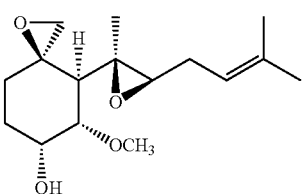 |
| 26 | 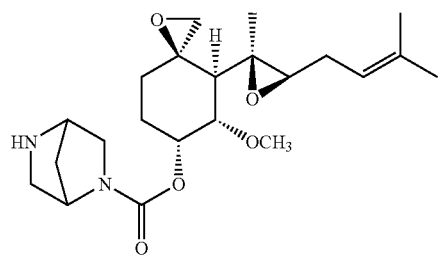 |
| 27 | 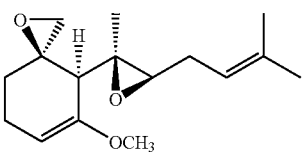 |
| 28 | 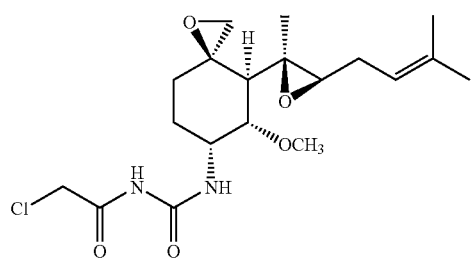 |

-continued
| Compound No. | Structure |
|---|---|
| 29 | 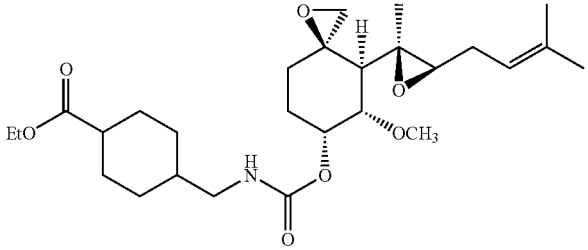 |
| 30 | 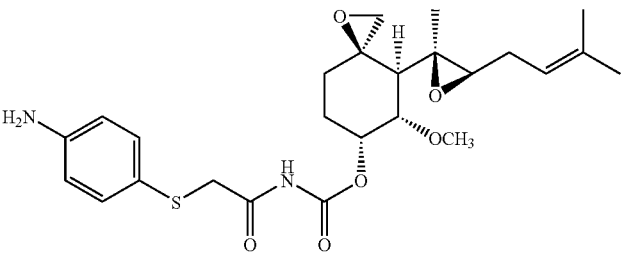 |
| 31 | 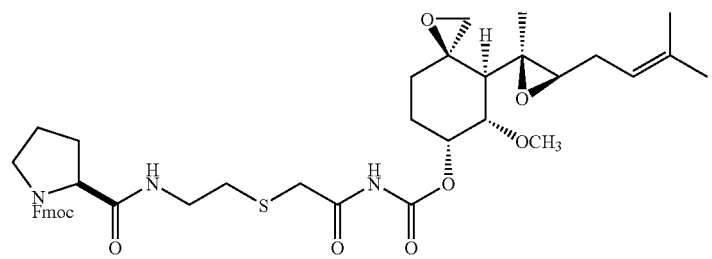 |
| 32 | 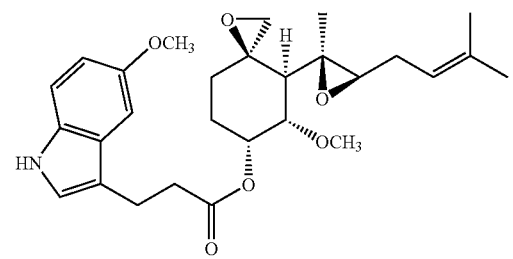 |
| 33 | 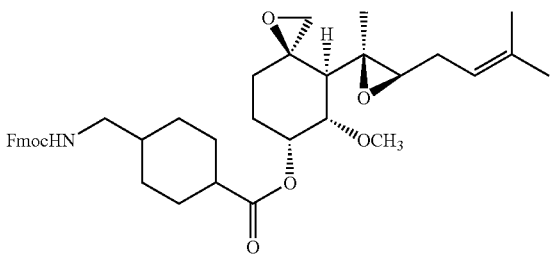 |
| 34 | 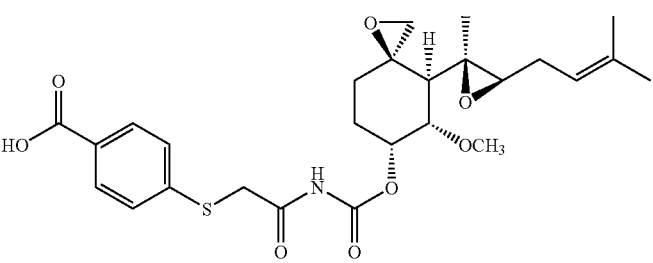 |

| Compound No. | Structure |
|---|---|
| 35 | 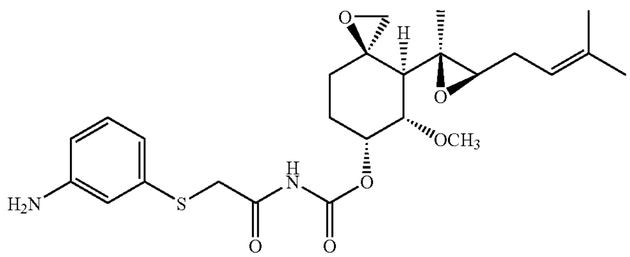 |
| 36 | 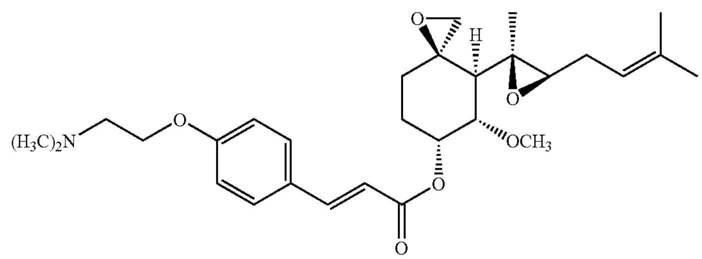 |
| 37 | 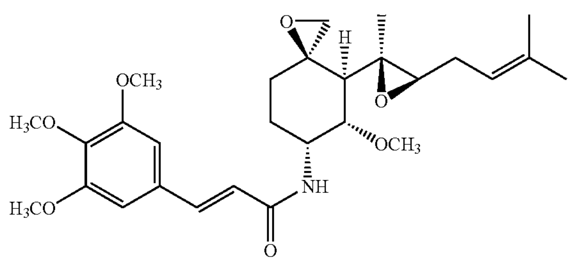 |
| 38 | 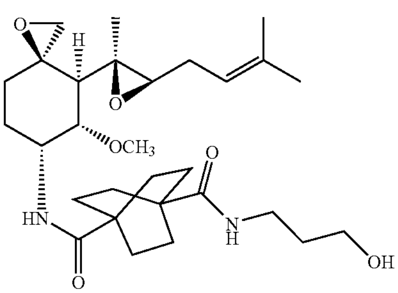 |
| 39 | 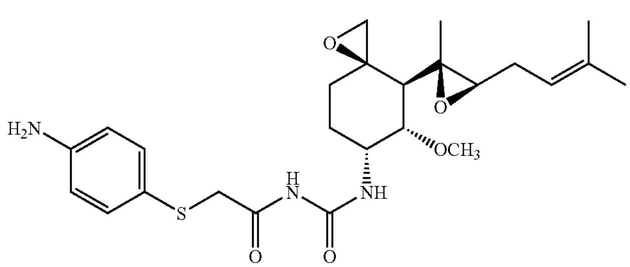 [SMILES: CO[C@@H]1[C@H](NC(=O)NC(=O)CSc2ccc(N)cc2)CC[C@]2(CO2)[C@H]1[C@@]1(C)O[C@@H]1CC=C(C)C] |

| Compound No. | Structure |
|---|---|
| 40 | 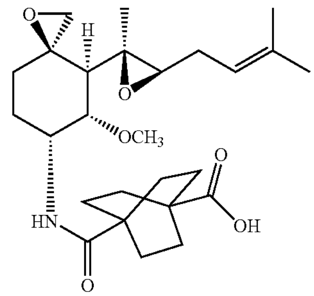 |
| 41 | 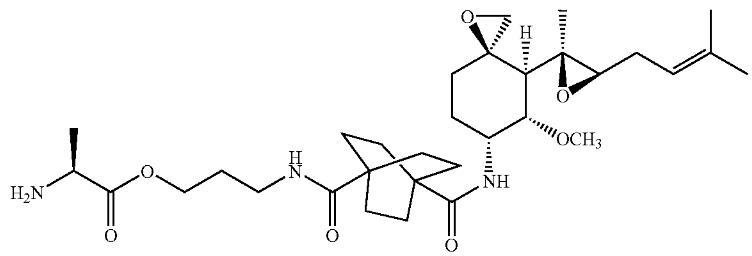 |
| 42 | 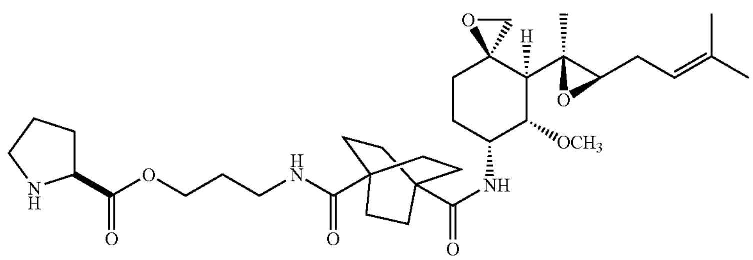 |
| 43 | 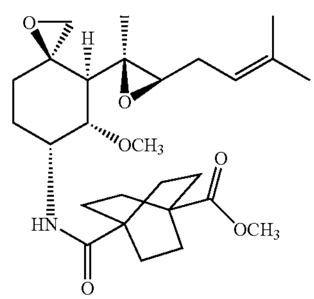 |
| 44 | 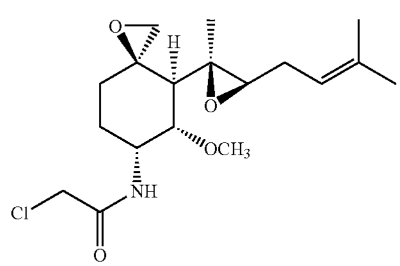 |

| Compound No. | Structure |
|---|---|
| 45 | 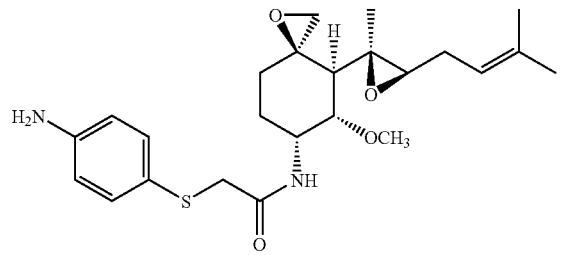 |
| 46 | 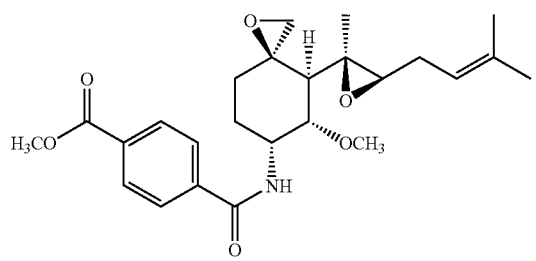 |
| 47 | 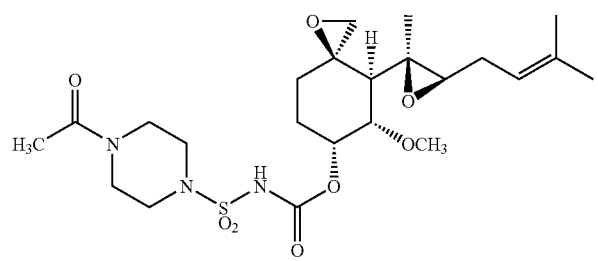 |
| 48 | 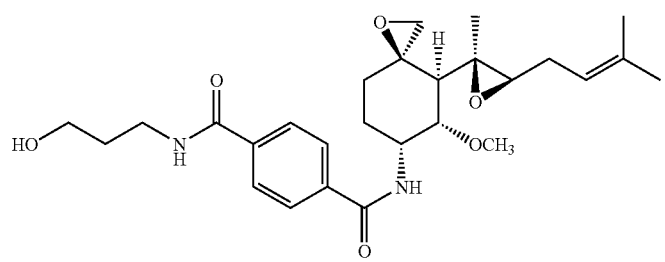 |
| 49 | 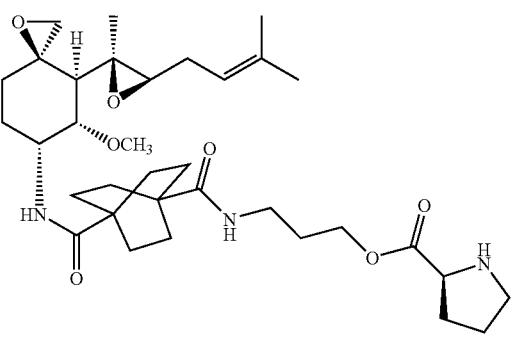 |

| Compound No. | Structure |
|---|---|
| 50 | 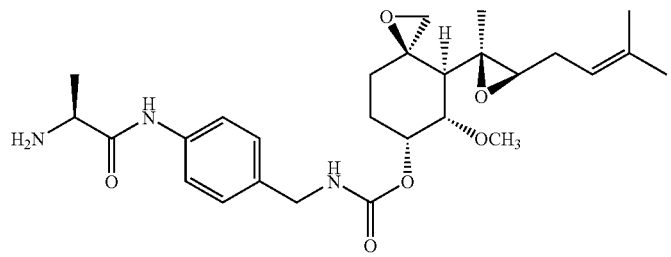 |
| 51 | 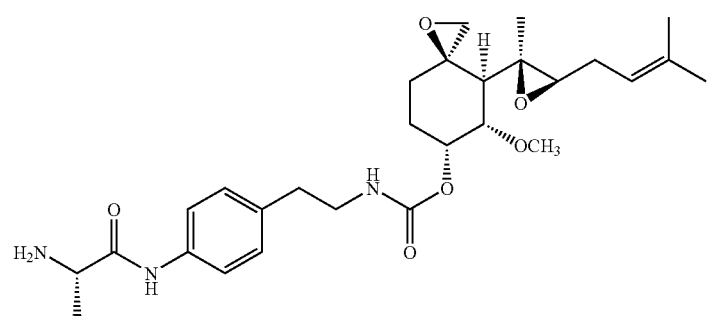 |
| 52 | 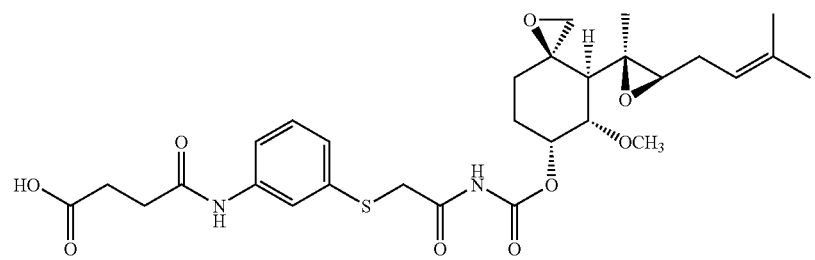 |
| 53 | 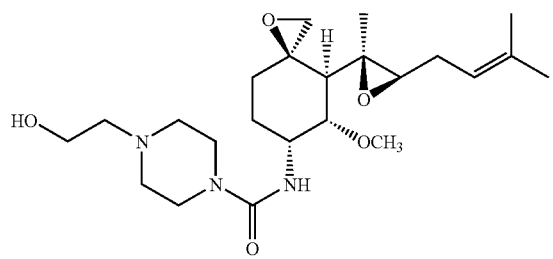 |
| 54 | 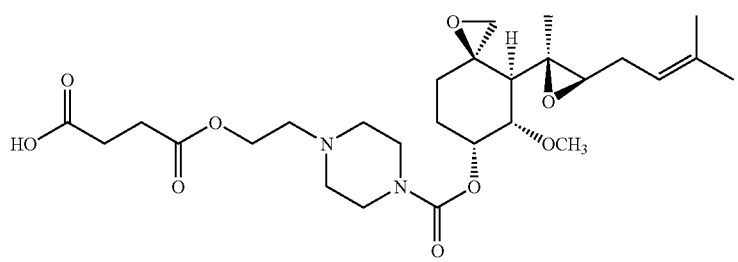 |

-continued

| Compound No. | Structure |
| --- | --- |
| 55 | [structure: Fmoc-proline ester linked via ethyl-piperazine-carbamate to fumagillol] |
| 56 | [structure: H2N-alanyl-piperazine-carbamate-fumagillol] |
| 57 | [structure: 4-aminophenethyl-urea-NH-fumagillol derivative with OCH3] |

Example 22

Inhibitory Effects of Fumagillin Conjugates on Tumor Growth Rates in B16F10 Mouse Melanoma BDF1 female mice (N=6) with 1×10$^6$ B16F10 tumor cells positioned subcutaneous in the flank were treated with various fumagillin conjugates of the invention. Tumor growth was monitored in parallel with positive and negative controls of cyclophosphamide and saline respectively. Treatment began when tumors reached an average size of 80-120 mg and tumor volumes were measured two times per week until animals reached an endpoint tumor volume of 2 grams or 45 days, whichever came first. Conjugates were administered as solutions in saline intravenously at dose levels of 30-100 mg/kg (expressed as fumagillin analog equivalents) on a schedule of q3dx4. Treatment outcomes were assessed in terms of percent tumor growth delay (% TGD), (see FIG. 1) defined as the percent increase in median time to endpoint for mice treated with an agent compared to those treated with saline.

Conjugates represented in Table 3 and FIG. 1 exhibited tumor growth delays in the ranges of 5-20, 20-50, and >50 percent. A number of fumagillin conjugates notably delayed tumor growth in mice bearing B16F10 tumors, thus illustrating the biological activity of these agents against mouse melanoma.

TABLE 3

Effect of Fumagillin Analog Conjugates on Tumor Growth Delay in a B16 Melanoma Cell Line

| Conjugate No. | mg/kg[1] | Route | Schedule | % TGD |
| --- | --- | --- | --- | --- |
| 6 | 80 | IV | q3d × 4 | 5-20 |
| 7 | 80 | IV | q3d × 4 | 5-20 |
| 9 | 100 | IV | q3d × 4 | 20-50 |
| 10 | 60 | IV | q3d × 4 | 20-50 |
| 11 | 65 | IV | q3d × 4 | 20-50 |
| 12 | 80 | IV | q3d × 4 | 5-20 |
| 13 | 80 | IV | q3d × 4 | 5-20 |
| 15 | 80 | IV | q3d × 4 | >50 |
| 16 | 80 | IV | q3d × 4 | 20-50 |
| 18 | 80 | IV | q3d × 4 | 5-20 |
| 19 | 40 | IV | q3d × 4 | 20-50 |
| 22 | 30 | IV | q3d × 4 | 5-20 |
| 23 | 80 | IV | q3d × 4 | 5-20 |
| 25 | 80 | IV | q3d × 4 | 20-50 |
| 26 | 60 | IV | q3d × 4 | 5-20 |
| 27 | 50 | IV | q3d × 4 | 5-20 |
| 31 | 80 | IV | q3d × 4 | 20-50 |
| 32 | 80 | IV | q3d × 4 | 20-50 |
| 33 | 65 | IV | q3d × 4 | 5-20 |
| 35 | 80 | IV | q3d × 4 | 20-50 |
| 38 | 80 | IV | q3d × 4 | 5-20 |
| 40 | 80 | IV | qod × 4 | 20-50 |
| 44 | 80 | IV | q3d × 4 | 5-20 |

[1]The range of doses is 30-100 mpk fumagillin analog-equiv. which corresponds to 300 mg-1.2 g conjugate.

Example 23

Inhibitory Effects of Fumagillin Conjugates on Tumor Growth Rates in A2058 Human Melanoma Xenograft Studies HRLN female mice (N=8) with $1 \times 10^7$ A2058 tumor cells positioned subcutaneous in flank were treated with fumagillin conjugates. Tumor growth was monitored in parallel with positive and negative controls of dacarbazine, and saline respectively. Treatment began when tumors reached an average size of 80-120 mg and tumor volumes were measured twice per week until animals reached an endpoint tumor size of 2 grams or 45 days, whichever came first. Conjugates were administered as solutions in saline intravenously at dose levels of 10-60 mg/kg (expressed in fumagillin analog equivalents) on a schedule of q4dx5. Treatment outcomes were assessed in terms of percent tumor growth delay (% TGD), defined as the percent increase in median time to endpoint for mice treated with an agent compared to those treated with saline.

As shown in FIG. 2, conjugates exhibited tumor growth delays in the range of 0-40 percent. A number of fumagillin conjugates notably delayed tumor growth in mice bearing A2058 tumors, thus illustrating the biological activity of these agents against human A2058 melanoma in mice.

Example 24

Inhibitory Effects of Fumagillin Conjugates on Tumor Growth Rates in PC3 Human Prostate Cancer Xenograft Studies HRLN female mice (N=8) with 1 mm³ PC3 tumor fragments positioned subcutaneous in flank were treated with fumagillin conjugates. Tumor growth was monitored in parallel with positive and negative controls of docetaxel and saline respectively. Treatment began when tumors reached an average size of 80-120 mg and tumor volumes were measured twice per week until animals reached an endpoint tumor size of 2 grams or 45 days, whichever came first. Conjugates were administered as solutions in saline intravenously at dose levels of 20-60 mg/kg (expressed in fumagillin analog equivalents) on a schedule of q4dx5. Treatment outcomes were assessed in terms of percent tumor growth delay (% TGD), defined as the percent increase in median time to endpoint for mice treated with an agent compared to those treated with saline.

Conjugates represented in FIG. 3 exhibited tumor growth delays in the range of 20-50 percent. A number of fumagillin conjugates notably delayed tumor growth in mice bearing human PC3 prostate cancer tumors, thus illustrating the biological activity of these agents against human PC3 prostate cancer in mice.

Example 25

Effects of Fumagillin Conjugates on Activity Levels in Mice Assessed Through Open Field Studies C57Bl/6 female mice (N=8) were housed until they reached 11 weeks of age. Animals were then regularly administered with fumagillin conjugates or TNP-470 and their activity levels monitored in an open field arena. Activity levels were assessed with saline as a control. Conjugates were administered as solutions in saline intravenously at dose levels of 50-100 mg/kg (expressed as fumagillin-analog equivalents) and TNP-470 was administered subcutaneously at dose levels of 50-100 mg/kg. Dosing was performed for four weeks on schedules ranging from q2d to once weekly, and activity levels were observed four times throughout the study: (1) prior to compound administration, (2) after one week of dosing, (3) after two weeks of dosing, and (4) following the final week of dosing. Animals were placed in the open field arena for 10 minutes per trial and their activity monitored in terms of travel distance, peripheral squares crossed, center squares crossed, and rearing events.

As represented in FIGS. 4 and 5 animals that were treated with fumagillin conjugates exhibited rearing-event activity levels similar to those of saline treated animals. In contrast, increased rearing-event activity levels were observed in mice that received TNP-470.

In the open field neurobehavioral models, animals that were treated with fumagillin conjugates performed in a manner similar to those that were treated with saline. Changes in activity observed with TNP-470 in the above described neurobehavioral models may be consistent with clinically observed TNP-470 side effects. Because increased rearing-event activity was not observed in fumagillin conjugate treated animals, these findings are testament to the potential increased neurological safety of fumagillin conjugates compared to their small molecule competitors/predecessors such as TNP-470.

Example 26

Fumagillin Analog Conjugates

Plasma and Cerebrospinal Fluid Pharmacokinetics Parameters

Male Sprague Dawley rats (Hsd: Sprague Dawley SD) were catheterized independently for blood and CSF collection and administered with a fumagillin conjugate or TNP-470, with a targeted active compound dose of 40 mg/kg (expressed in fumagillin-analog equivalents) and a dose volume of 10 mL/kg. The plasma samples were analyzed for conjugated and small molecule active fumagillin compounds. For TNP-470, both the parent TNP-470, and the known metabolite M-IV, were assessed. CSF samples were analyzed for small molecule fumagillin analogs only, i.e. the fumagillin-analog released from the corresponding conjugate. Analyses for fumagillin conjugates were carried out after their isolation from plasma by co-precipitation with plasma proteins and subsequent conversion into low molecular weight fumagillin products by basic hydrolysis. Liquid chromatography tandem mass-spectrometry (LC/MS/MS) was used for fumagillin compound detection in biological fluids.

Data for conjugates 12, 15, 19, and 24 and TNP-470 are provided below. The protocol design is outlined in Table 4, and sampling timepoints are tabulated in Table 5.

TABLE 4

Protocol Design

| | | Treatment Regimen | | | | |
|---|---|---|---|---|---|---|
| Group | n | Agent | Catheter Type | mg/kg | Route | Schedule |
| 1 | 3 | No treatment | Intra-cisternal | — | IV | qd x 1 |
| 2 | 3 | Conjugate 12 | Jugular | 40 | IV | qd x 1 |
| 3 | 4 | Conjugate 12 | Intra-cisternal | 40* | IV | qd x 1 |
| 4 | 4 | Conjugate 12 | Intra-cisternal | 40* | IV | qd x 1 | delivered in a sustained fashion in the plasma, resulting in significantly increased exposure in plasma relative to TNP-470.

TABLE 4-continued

Protocol Design

Treatment Regimen

| Group | n | Agent | Catheter Type | mg/kg | Route | Schedule |
|---|---|---|---|---|---|---|
| 2' | 3 | Conjugate 15 | Jugular | 40 | IV | qd x 1 |
| 3' | 4 | Conjugate 15 | Intra-cisternal | 40 | IV | qd x 1 |
| 4' | 4 | Conjugate 15 | Intra-cisternal | 40 | IV | qd x 1 |
| 2" | 3 | Conjugate 19 | Jugular | 10 | IV | qd x 1 |
| 3" | 4 | Conjugate 19 | Intra-cisternal | 10 | IV | qd x 1 |
| 4" | 4 | Conjugate 19 | Intra-cisternal | 10 | IV | qd x 1 |
| 2''' | 3 | Conjugate 24 | Jugular | 40 | IV | qd x 1 |
| 3''' | 4 | Conjugate 24 | Intra-cisternal | 40 | IV | qd x 1 |
| 4''' | 4 | Conjugate 24 | Intra-cisternal | 40 | IV | qd x 1 |
| 5 | 3 | TNP-470 | Jugular | 40 | IV | qd x 1 |
| 6 | 4 | TNP-470 | Intra-cisternal | 40 | IV | qd x 1 |
| 7 | 4 | TNP-470 | Intra-cisternal | 40 | IV | qd x 1 |

Pharmacokinetic sampling was performed for each group as described in Table 5.
*In some cases the dose was adjusted to 10 mg/kg due to viscosity and the volume was increased to 20 mL/kg

TABLE 5

Sampling Timepoints by Group and Tissue

| Timepoint | Plasma | CSF |
|---|---|---|
| Any time | G1 | G1 |
| 5 minutes | G2, G2', G2", G2''' | |
| 10 minutes | G5 | G3, G3', G3", G3''', G6 |
| 1 hour | G2, G2', G2", G2''', G5 | |
| 2 hours | G2, G2', G2", G2''', G5 | G4, G4', G4", G4''', G7 |
| 4 hours | G2, G2', G2", G2''', G5 | |
| 6 hours | G2, G2', G2", G2''' | |
| 8 hours | G2, G2', G2", G2''', G5 | G3, G3', G3", G3''', G6 |
| 10 hours | G2, G2', G2", G2''' | |
| 12 hours | G2, G2', G2", G2''' | |
| 24 hours | G2, G2', G2", G2''' | G4, G4', G4", G4''', G7 |

The results of the tests described in Example 26 are shown in Tables 6 and 7.

TABLE 6

PK Characteristics for Conjugated and Conjugate Released Fumagillin Derivatives[#]

| | Conjugated Fumagillin Analog PK parameters | | Released/free Fumagillin analog plasma PK parameters | | | | | |
|---|---|---|---|---|---|---|---|---|
| Conjugate/Compound | $T_{max}$ (h) | $t\frac{1}{2}$ (h) | $T_{max}$ (h) | $C_{max}$ (ng/ml) | $t\frac{1}{2}$ (h) | AUC 0-t (μg * h/ml) | AUC 0-24 (μg * h/ml) | AUC 0-inf (μg * h/ml) |
| Conjugate 12 | 0.083 | 19.4 | 0.083 | 421 | 20.4 | 2.9 | 2.9 | 5.4 |
| Conjugate 15 | 0.083 | 3.5 | 0.083 | 20203 | 3.7 | 40.5 | 40.5 | 41.6 |
| Conjugate 19 | 0.083 | 12.2 | 0.083 | 1775 | 8.1 | 1.8 | 1.8 | 2.2 |
| Conjugate 24 | 0.083 | 5.0 | 0.083 | 7067 | 5.3 | 17.4 | 17.4 | 19.1 |
| TNP-470 metabolite M-IV | n/a | n/a | 1 | 318 | 0.6 | 0.4 | 0.4 | 0.4 |

[#](mean, N = 3). Data expressed in fumagillin-analog equivalents and dose normalized to 40 mg/kg fumagillin analog equivalents.

As represented by the data in Table 6, the fumagillin conjugates have a significantly longer half-life in comparison to TNP-470. As a result of conjugation, the fumagillin analog is

TABLE 7

| | | Fumagillin analog CSF accumulation | | | |
|---|---|---|---|---|---|
| Conjugate/Compound Dosed[##] | $T_{max}$ (h) | $C_{max}$ (ng/ml) | AUC 0-t (μg * h/ml) | AUC 0-24 (μg * h/ml) | AUC 0-inf (μg * h/ml) |
| Conjugate 12 | 2.0 | 26 | n/a* | n/a* | n/a* |
| Conjugate 15 | 0.17 | 1084 | n/a* | n/a* | n/a* |
| Conjugate 19 | 0.17 | n/a* | n/a* | n/a* | n/a* |
| Conjugate 24 | 0.17 | 128 | 1.10 | 1.10 | 1.29 |
| TNP-470 metabolite MIV | 0.17 | 1642 | 1.67 | 1.72 | 1.72 |

*The lower limit of quantitation (LLOQ) for fumagillin analogs was 5 ng/mL. In cases where the concentrations at various timepoints were below the LLOQ Cmax and/or AUC could not be calculated.
[##]Data represent the fumagillin-analog released from the corresponding conjugate; data is normalized to an administered dose of 40 mg/kg, expressed in fumagillin-analog equivalents As represented by the data in Table 7, after dosing 40 mg/kg in rats, the concentrations of fumagillin analogs detected in the CSF are very low, with $C_{max}$ values below the level observed for the TNP-470 metabolite MIV. A graphical representation of the CSF levels observed is depicted in FIG. 6.

The very low amounts of fumagillin analog observed in the CSF of rats after dosing of the corresponding conjugate is consistent with the polymer conjugate not crossing the blood-brain barrier, resulting in very low levels (in many instances below the LLOQ) of the corresponding fumagillin analog detected in the CSF. These data demonstrate that conjugation of a fumagillin analog can result in very low levels of the fumagillin analog entering the CNS compartment, and consequently result in decreased CNS toxicity in comparison to the small-molecule fumagillin analog TNP-470.

While particular embodiments described herein have been illustrated and described, it would be obvious to those skilled in the art that various other changes and modifications can be made without departing from the spirit and scope of the disclosure. It is therefore intended to cover in the appended claims all such changes and modifications that are within the scope of this invention.

The invention claimed is:

1. A conjugate of Formula I or a pharmaceutically acceptable salt thereof:

$$[\text{fumagillin analog}]_m\text{-polyal} \quad \quad \text{I}$$

wherein the fumagillin analog is a fumagillin core structure which demonstrates MetAP-2 inhibition along with a chemical spacer moiety that allows the fumagillin core structure to be covalently attached through X at the C-6 of the fumagillin core structure to an OH of the polyal, wherein the fumagillin core structure has the formula II:

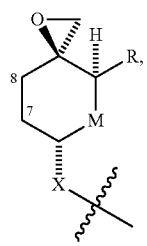

wherein
X is O, $S(=O)_q$, NH, or optionally substituted $CH_2$, wherein one or both of the hydrogen atoms in the optionally substituted $CH_2$ can be substituted with OH, halogen, CN, C1-C6 alkyl, C2-C6 alkenyl, C2-C6 alkynyl, C1-C6 alkoxy, C1-C3 fluorinated alkyl, $NO_2$, $NH_2$, NHC1-C6 alkyl, N(C1-C6 alkyl)$_2$, NHC(O)C1-C6 alkyl, NHC(O)NHC1-C6 alkyl, $SO_2NH_2$, $SO_2NHC1$-C6 alkyl, $SO_2N$(C1-C6 alkyl)$_2$, $NHSO_2C1$-C6 alkyl, C(O)OC1-C6 alkyl, CONHC1-C6 alkyl, CON(C1-C6 alkyl)$_2$, or C1-C6 alkyl;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, $C_2$-heterocyclic-$C_1$-$C_6$ alkyl, $C_2$-heterocyclic-$C_2$-$C_6$ alkenyl, $C_1$-$C_6$ alkyl, $C_2$-$C_6$ alkenyl, $C_2$-heterocyclic-$C_1$-$C_6$-alkenyl-COO—$C_1$-$C_6$ alkyl, $C_2$-heterocyclic-$C_1$-$C_6$ alkyl-COO—$C_1$-$C_6$-alkyl, $C_1$-$C_6$ alkyl=N—O—$C_1$-$C_6$ alkyl-aryl, $C(O)C_1$-$C_6$ alkyl, CN, or halogen;

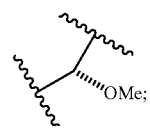

M is O, or
q is 0, 1, or 2;
wherein the compound is optionally substituted at C-7 and C-8, independently, with $C_1$-$C_6$ alkyl, $C_2$-$C_6$ alkenyl, $C_2$-$C_6$ alkynyl, OH, ketone, or alkoxy;
m is an integer from 1 to 40; and
polyal has the structure

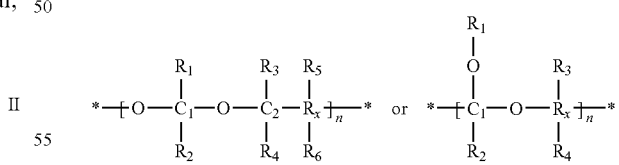

wherein n is an integer from 1 to 3000;
wherein the fumagillin analog is directly or indirectly attached to $R_1$, $R_2$, $R_3$, $R_4$, $R_5$, or $R_6$;
wherein for each occurrence of the n bracketed structure, either
one of $R_1$ and $R_2$ is hydrogen, and the other is —$CH_2$—OH or —$CH_2$—OH whose hydroxyl is covalently attached to Linker, or
each of $R_1$ and $R_2$ is —$CH_2$—OH or —$CH_2$—OH whose hydroxyl is covalently attached to Linker;

$R_x$ is a carbon atom which is covalently attached to $C_2$ or to the oxygen;

each of $R_3$, $R_4$, $R_5$, and $R_6$ is independently hydrogen, —CH₂—OH or —CH₂—OH whose hydroxyl is covalently attached to Linker; wherein Linker is

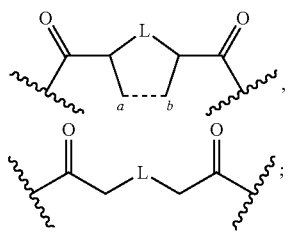

L is a bond, —CH(OH)—, —NH—, —O—, —S—, —SO—, —SO₂—, —C(CH₃)₂—, —CHO—, —COCH₂— or optionally substituted —CH₂—, wherein one or both of the hydrogen atoms in the optionally substituted CH₂ can be substituted with OH, halogen, CN, C1-C6 alkyl, C2-C6 alkenyl, C2-C6 alkynyl, C1-C6 alkoxy, C1-C3 fluorinated alkyl, NO₂, NH₂, NHC1-C6 alkyl, N(C1-C6 alkyl)₂, NHC(O)C1-C6 alkyl, NHC(O)NHC1-C6 alkyl, SO₂NH₂, SO₂NHC1-C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl;

the dashed line between the carbon atoms at positions a and b represents a carbon-carbon single bond or a carbon-carbon double bond; and the carbon atoms adjacent to L can be individually optionally substituted with OH, halogen, CN, C1-C6 alkyl, C2-C6 alkenyl, C2-C6 alkynyl, C1-C6 alkoxy, C1-C3 fluorinated alkyl, NO₂, NH₂, NHC1-C6 alkyl, N(C1-C6 alkyl)₂, NHC(O)C1-C6 alkyl, NHC(O)NHC1-C6 alkyl, SO₂NH₂, SO₂NHC1-C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl, or wherein Linker is an oxalic, malonic, succinic, glutaric, adipic, pimelic, suberic, azelaic, sebacic, phthalic, isophthalic, terephthalic, diglycolic acid, tartaric, glutamic, fumaric, or aspartic moiety.

2. The conjugate of claim 1 or a pharmaceutically acceptable salt thereof, wherein the fumagillin core structure has the formula A:

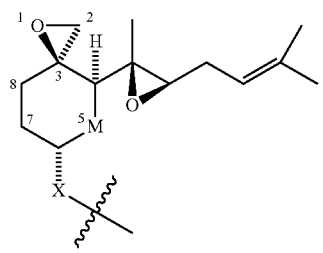

wherein C-7 and C-8 are optionally substituted independently, with $C_1$-$C_6$ alkyl, $C_2$-$C_6$ alkenyl, $C_2$-$C_6$ alkynyl, OH, ketone, or alkoxy;

X is O, S(=O)$_q$, NH, or optionally substituted CH₂, wherein one or both of the hydrogen atoms in the optionally substituted CH₂ can be substituted with OH, halogen, CN, C1-C6 alkyl, C2-C6 alkenyl, C2-C6 alkynyl, C1-C6 alkoxy, C1-C3 fluorinated alkyl, NO₂, NH₂, NHC1-C6 alkyl, N(C1-C6 alkyl)₂, NHC(O)C1-C6 alkyl, NHC(O)NHC1-C6 alkyl, SO₂NH₂, SO₂NHC1-C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl;

M is O, or

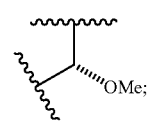

q is 0, 1, or 2.

3. The conjugate of claim 1 or a pharmaceutically acceptable salt thereof, wherein the polyal has the structure

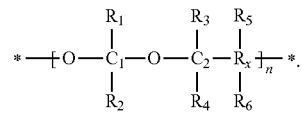

4. A conjugate of a polyal and a compound of the Formula II or a pharmaceutically acceptable salt thereof:

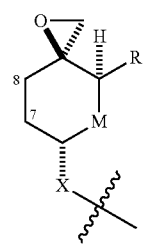

II wherein

X is O, S(=O)$_q$, NH or optionally substituted CH₂, wherein one or both of the hydrogen atoms in the optionally substituted CH₂ can be substituted with OH, halogen, CN, C1-C6 alkyl, C2-C6 alkenyl, C2-C6 alkynyl, C1-C6 alkoxy, C1-C3 fluorinated alkyl, NO₂, NH₂, NHC1-C6 alkyl, N(C1-C6 alkyl)₂, NHC(O)C1-C6 alkyl, NHC(O)NHC1-C6 alkyl, SO₂NH₂, SO₂NHC1-C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C2-heterocyclic-$C_1$-$C_6$ alkyl, C2-heterocyclic-$C_2$-$C_6$ alkenyl, $C_1$-$C_6$ alkyl, $C_2$-$C_6$ alkenyl, $C_2$-heterocyclic-$C_1$-$C_6$-alkenyl-COO—$C_1$-$C_6$ alkyl, $C_2$-heterocyclic-$C_1$-$C_6$ alkyl-COO—$C_1$-$C_6$-alkyl, $C_1$-$C_6$ alkyl=N—O—$C_1$-$C_6$ alkyl-aryl, C(O)$C_1$-$C_6$ alkyl, CN, or halogen;

M is O, or

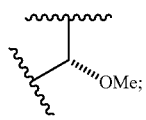

q is 0, 1, or 2;
wherein the compound is optionally substituted at C-7 and C-8, independently, with $C_1$-$C_6$ alkyl, $C_2$-$C_6$ alkenyl, $C_2$-$C_6$ alkynyl, OH, ketone, or alkoxy;
wherein

represents covalent attachment of X to a free hydroxyl of the polyal through a spacer moiety of the Formula III

III wherein Tether is present or absent, and if present, has a molecular weight up to about 1000 and is covalently attached to both X and to Linker;
wherein Linker is present or absent, and if present, has a molecular weight up to about 1000 and is covalently attached to both Tether and to a free hydroxyl of the polyal; and
wherein the spacer moiety of Formula III has one or more labile bonds capable of enzymatic or chemical cleavage;
wherein the polyal has the structure:

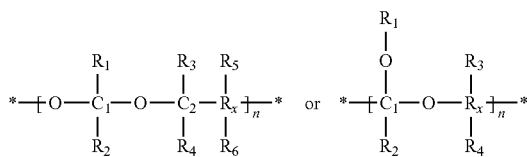

wherein n is an integer from 1 to 3000;
wherein the spacer moiety of Formula III is directly or indirectly attached to $R_1$, $R_2$, $R_3$, $R_4$, $R_5$, or $R_6$;
wherein for each occurrence of the n bracketed structure, either
one of $R_1$ and $R_2$ is hydrogen, and the other is —$CH_2$—OH or —$CH_2$—OH whose hydroxyl is covalently attached to Linker,
each of $R_1$ and $R_2$ is —$CH_2$—OH or —$CH_2$—OH whose hydroxyl is covalently attached to Linker;
$R_x$ is a carbon atom which is covalently attached to C2 or to the oxygen;
each of $R_3$, $R_4$, $R_5$, and $R_6$ is independently hydrogen, —$CH_2$—OH or —$CH_2$—OH whose hydroxyl is covalently attached to Linker;
wherein Linker is

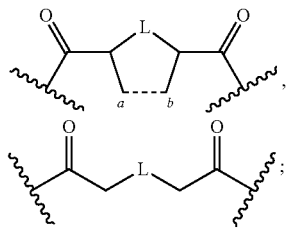

L is a bond, —CH(OH)—, —NH—, —O—, —S—, —SO—, —$SO_2$—, —$C(CH_2)_2$—, —CHO—, —$COCH_2$— or optionally substituted —$CH_2$—, wherein one or both of the hydrogen atoms in the optionally substituted $CH_2$ can be substituted with OH, halogen, CN, C1-C6 alkyl, C2-C6 alkenyl, C2-C6 alkynyl, C1-C6 alkoxy, C1-C3 fluorinated alkyl, $NO_2$, $NH_2$, NHC1—C6 alkyl, N(C1-C6 alkyl)$_2$, NHC(O)C1-C6 alkyl, NHC(O)NHC1-C6 alkyl, $SO_2NH_2$, $SO_2$NHC1-C6 alkyl, $SO_2$N(C1-C6 alkyl)$_2$, $NHSO_2$C1-C6 alkyl, C(O)OC1-C6 alkyl, CONHC1-C6 alkyl, CON(C1-C6 alkyl)$_2$, or C1-C6 alkyl;
the dashed line between the carbon atoms at positions a and b represents a carbon-carbon single bond or a carbon-carbon double bond; and
the carbon atoms adjacent to L can be individually optionally substituted with OH, halogen, CN, C1-C6 alkyl, C2-C6 alkenyl, C2-C6 alkynyl, C1-C6 alkoxy, C1-C3 fluorinated alkyl, $NO_2$, $NH_2$, NHC1-C6 alkyl, N(C1-C6 alkyl)$_2$, NHC(O)C1-C6 alkyl, NHC(O)NHC1-C6 alkyl, $SO_2NH_2$, $SO_2$NHC1-C6 alkyl, $SO_2$N(C1-C6 alkyl)$_2$, $NHSO_2$C1-C6 alkyl, C(O)OC1-C6 alkyl, CONHC1-C6 alkyl, CON(C1-C6 alkyl)$_2$, or C1-C6 alkyl,
or wherein Linker is an oxalic, malonic, succinic, glutaric, adipic, pimelic, suberic, azelaic, sebacic, phthalic, isophthalic, terephthalic, diglycolic acid, tartaric, glutamic, fumaric, or aspartic moiety.

5. The conjugate of claim 4 or a pharmaceutically acceptable salt thereof, wherein R is (2S,3R)-2-methyl-3-(3-methylbut-2-enyl)oxiranyl.

6. The conjugate of claim 4 or a pharmaceutically acceptable salt thereof, wherein Linker is

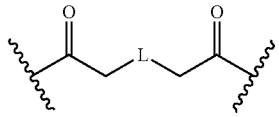

and L is —$CH_2$—.

7. The conjugate of claim 6 or a pharmaceutically acceptable salt thereof, wherein L is —$CH_2$—.

8. The conjugate of claim 6 or a pharmaceutically acceptable salt thereof, wherein L is —O—.

9. The conjugate of claim 5 or a pharmaceutically acceptable salt thereof, wherein the polyal has the structure:

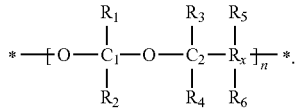

10. The conjugate of claim 9 or a pharmaceutically acceptable salt thereof, wherein the polyal is a conjugation product of poly(1-hydroxymethylethylene hydroxymethyl-formal) (PHF).

11. The conjugate of claim 10 or a pharmaceutically acceptable salt thereof, wherein the conjugation product is a conjugation product of poly(1-hydroxymethylethylene hydroxymethyl-formal) (PHF) and the PHF has a molecular weight from about 40 kDa to about 100 kDa.

12. The conjugate of claim 11 or a pharmaceutically acceptable salt thereof, wherein the conjugation product is a conjugation product of poly(1-hydroxymethylethylene hydroxymethyl-formal) (PHF) and the PHF has a molecular weight of about 70 kDa.

13. A conjugate of the Formula IV or a pharmaceutically acceptable salt thereof:

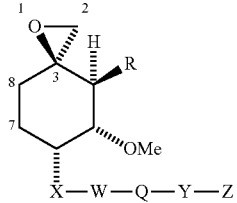

IV wherein
X is O, S(=O)$_q$, NH or optionally substituted CH$_2$, wherein one or both of the hydrogen atoms in the optionally substituted CH$_2$ can be substituted with OH, halogen, CN, C1-C6 alkyl, C2-C6 alkenyl, C2-C6 alkynyl, C1-C6 alkoxy, C1-C3 fluorinated alkyl, NO$_2$, NH$_2$, NHC1-C6 alkyl, N(C1-C6 alkyl)$_2$, NHC(O)C1-C6 alkyl, NHC(O)NHC1-C6 alkyl, SO$_2$NH$_2$, SO$_2$NHC1-C6 alkyl, SO$_2$N(C1-C6 alkyl)$_2$, NHSO$_2$C1-C6 alkyl, C(O)OC1-C6 alkyl, CONHC1-C6 alkyl, CON(C1-C6 alkyl)$_2$, or C1-C6 alkyl;

q is 0, 1, or 2;

R is (2S,3R)-2-methyl-3-(3-methylbut-2-enyl)oxirane, 2-methylhepta-2,5-diene, (2R,3S)-2-isopentyl-3-methyloxirane, 6-methylhept-2-ene, (Z)-acetaldehyde O-benzyl oxime, C$_2$-heterocyclic-C$_1$-C$_6$ alkyl, C$_2$-heterocyclic-C$_2$-C$_6$ alkenyl, C$_1$-C$_6$ alkyl, C$_2$-C$_6$ alkenyl, C$_2$-heterocyclic-C$_1$-C$_6$-alkenyl-COO—C$_1$-C$_6$ alkyl, C$_2$-heterocyclic-C$_1$-C$_6$ alkyl-COO—C$_1$-C$_6$-alkyl, C$_1$-C$_6$ alkyl=N—O—C$_1$-C$_6$ alkyl-aryl, C(O)C$_1$-C$_6$ alkyl, CN, or halogen;

W is null, a bond, —C(O)—, —NH—, —C$_1$-C$_6$ alkyl-, —C$_2$-C$_6$ alkenyl-, —C$_2$-C$_6$ alkynyl-, —C$_1$-C$_6$ alkoxy-, -aryl-, -heteroaryl-, -cycloalkyl-, —C(O)bicycloalkylC(O)—, —SO$_2$-bicycloalkyl-, -heterocycloalkyl-, heterobicycloalkyl-, —C(O)C$_1$-C$_6$ alkyl heteroaryl-O—, —C(O)—C$_1$-C$_6$-alkenyl-aryl-O—N(C$_1$-C$_6$ alkyl)$_2$—, —C(O)-heterocycloalkyl-C$_1$-C$_6$ alkyl-O—, —C(O)-heterocycloalkyl-C$_1$-C$_6$ alkyl-COO—, —C(O)-heterobicycloalkyl-C$_1$-C$_6$ alkyl-COO—, —C(O)-heterobicycloalkyl-C$_1$-C$_6$ alkyl—C(O)—, —C(O)NH(C$_1$-C$_6$ alkyl)heteroaryl(O)—, —C(O)NH(C$_1$-C$_6$ alkyl)aryl(O)—, —C(O)C$_1$-C$_6$alkylaryl-, —NHC(O)C$_1$-C$_6$-alkylaryl-, —C(O)C$_1$-C$_6$ alkenyl-aryl-O—NH(C$_1$-C$_6$-alkyl)-, C(O)NH(C$_1$-C$_6$ alkyl)cycloalkylCOO—, —C(O)cycloalkyl C$_1$-C$_6$ alkyl NH—, —NHC(O)C$_1$-C$_6$ alkyl-, —NHC(O)NHC$_1$-C$_6$ alkyl-, —SO$_2$NH—, —SO$_2$NHC$_1$-C$_6$ alkyl-, —SO$_2$N(C$_1$-C$_6$ alkyl)$_2$—, —NHSO$_2$C$_1$-C$_6$ alkyl-, —CO$_2$C$_1$-C$_6$ alkyl-, —CONHC$_1$-C$_6$ alkyl-, —CON(C$_2$-C$_6$ alkyl)-, —C$_1$-C$_6$ alkyl aryl-O—C$_1$-C$_6$ alkyl N(C$_1$-C$_6$ alkyl)$_2$—, —C(O)NHC(O)C$_1$-C$_1$ alkyl S C$_0$-C$_6$ alkyl aryl-, —C$_1$-C$_6$ alkyl NH—SO$_2$-heterocyclo-C$_1$-C$_6$ alkyl-O—, —C(O)NHC(O)C$_1$-C$_6$ alkyl S C$_0$-C$_6$alkylNH—, —C(O)NH—C$_1$-C$_6$ alkyl-aryl-, —C(O)heterocycloalkyl-, —C(O)—C$_1$-C$_6$-alkyl-S-aryl-, —C(O)heterobicycloalkyl-, —O(O)—NH—C(O)—C$_1$-C$_6$ alkyl-, or —C(O)—NH—C(O)—C$_0$-C$_6$ alkyl-S-aryl-;

Q is null, —NH—, -amino acid-, —NH-amino acid-, —(C$_1$-C$_6$ alkyl COO)—, —(OOCC$_1$-C$_6$-alkyl COO)—, —(C$_1$-C$_6$ alkyl-O-amino acid)-, or —(C$_1$-C$_2$ alkyl-O)—;

Y is null, an oxalic, malonic, succinic, glutaric, oxaglutaric, adipic, pimelic, suberic, azelaic, sebacic, phthalic, isophthalic, terephthalic, diglycolic acid, tartaric, glutamic, fumaric, or aspartic moiety; and Z is a polyal with the structure:

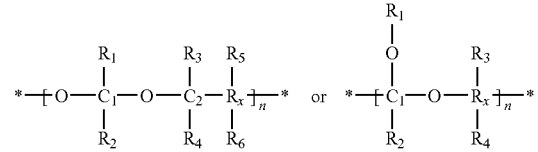

wherein n is an integer from 1 to 3000;
wherein X, W, Q or Y is attached to R$_1$, R$_2$, R$_3$, R$_4$, R$_5$, or R$_6$;
wherein for each occurrence of the n bracketed structure, either
one of R$_1$ and R$_2$ is hydrogen, and the other is —CH$_2$—OH or —CH$_2$—OH whose hydroxyl is covalently attached to Linker, or
each of R$_1$ and R$_2$ is —CH$_2$—OH or —CH$_5$—OH whose hydroxyl is covalently attached to Linker;
R$_x$ is a carbon atom which is covalently attached to C$_2$ or to the oxygen;
each of R$_3$, R$_4$, R$_5$, and R$_6$ is independently hydrogen, —CH$_2$—OH or —CH$_2$—OH whose hydroxyl is covalently attached to Linker;
wherein Linker is

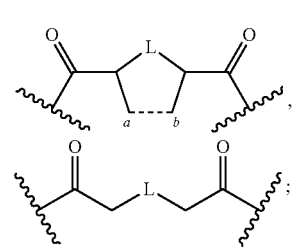

L is a bond, —CH(OH)—, —NH—, —O—, —S—, —SO—, —SO$_2$—, —C(CH$_2$)$_2$—, —CHO—, —COCH$_2$— or optionally substituted —CH$_2$—, wherein one or both of the hydrogen atoms in the optionally substituted CH$_2$ can be substituted with OH, halogen, CN, C1-C6 alkyl, C2-C6 alkenyl, C2-C6 alkynyl, C1-C6 alkoxy, C1-C3 fluorinated alkyl, NO$_2$, NH$_2$, NHC1-C6 alkyl, N(C1-C6 alkyl)$_2$, NHC(O)C1-C6 alkyl, NHC(O)NHC1-C6 alkyl, SO$_2$NH$_2$, SO$_2$NHC1-

C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl;

the dashed line between the carbon atoms at positions a and b represents a carbon-carbon single bond or a carbon-carbon double bond; and the carbon atoms adjacent to L can be individually optionally substituted with OH, halogen, CN, C1-C6 alkyl, C2-C6 alkenyl, C2-C6 alkynyl, C1-C6 alkoxy, C1-C3 fluorinated alkyl, NO₂, NH₂, NHC1-C6 alkyl, N(C1-C6 alkyl)₂, NHC(O)C1-C6 alkyl, NHC(O)NHC1-C6 alkyl, SO₂NH₂, SO₂NHC1-C6 alkyl, SO₂N(C1-C6 alkyl)₂, NHSO₂C1-C6 alkyl, C(O)OC1-C6 alkyl, CONHC1-C6 alkyl, CON(C1-C6 alkyl)₂, or C1-C6 alkyl, or wherein Linker is an oxalic, malonic, succinic, glutaric, adipic, pimelic, suberic, azelaic, sebacic, phthalic, isophthalic, terephthalic, diglycolic acid, tartaric, glutamic, fumaric, or aspartic moiety.

14. The conjugate of claim 13 or a pharmaceutically acceptable salt thereof, wherein Z is a conjugation product of poly(1-hydroxymethylethylene hydroxymethyl-formal) (PHF).

15. The conjugate of claim 14 or a pharmaceutically acceptable salt thereof, wherein the conjugation product is a conjugation product of poly(1-hydroxymethylethylene hydroxymethyl-formal) (PHF) and the PHF has a molecular weight of about 70 kDa.

16. The conjugate of claim 13 or a pharmaceutically acceptable salt thereof, wherein X is O.

17. The conjugate of claim 13 or a pharmaceutically acceptable salt thereof, wherein X is NH.

18. The conjugate of claim 13 or a pharmaceutically acceptable salt thereof, wherein Y is —C(O)CH₂CH₂(O)C.

19. The conjugate of claim 13 or a pharmaceutically acceptable salt thereof, wherein Y is —C(O)CH₂CH₂OCH₂CH₂(O)C.

20. The conjugate of claim 16 or a pharmaceutically acceptable salt thereof, wherein Y is —C(O)CH₂CH₂CH₂(O)C—.

21. The conjugate of claim 20 or a pharmaceutically acceptable salt thereof, wherein R is (2S,3R)-2-methyl-3-(3-methylbut-2-enyl)oxiranyl.

22. The conjugate of claim 21 or a pharmaceutically acceptable salt thereof, wherein Q is NH.

23. The conjugate of claim 22 or a pharmaceutically acceptable salt thereof, wherein W is —C(O)NH—C₁-C₆ alkyl-aryl-.

24. The conjugate of claim 13 or a pharmaceutically acceptable salt thereof, wherein W is —C(O)—NH—C(O)—C₀-C₆ alkyl-S-aryl-.

25. A composition comprising the conjugate or pharmaceutically acceptable salt of the conjugate of claim 1 and a pharmaceutically acceptable carrier.

26. The composition of claim 25, wherein the pharmaceutically acceptable carrier is suitable for injectable administration and the composition comprises an injectable dosage form.

27. A composition comprising the conjugate or pharmaceutically acceptable salt of the conjugate of claim 4 and a pharmaceutically acceptable carrier.

28. The composition of claim 27, wherein the pharmaceutically acceptable carrier is suitable for injectable administration and the composition comprises an injectable dosage form.

29. A composition comprising the conjugate or pharmaceutically acceptable salt of the conjugate of claim 13 and a pharmaceutically acceptable carrier.

30. The composition of claim 29, wherein the pharmaceutically acceptable carrier is suitable for injectable administration and the composition comprises an injectable dosage form.

31. The conjugate of claim 15 or a pharmaceutically acceptable salt thereof, wherein R is (2S,3R)-2-methyl-3-(3-methylbut-2-enyl)oxiranyl.

32. The conjugate of claim 16 or a pharmaceutically acceptable salt thereof, wherein R is (2S,3R)-2-methyl-3-(3-methylbut-2-enyl)oxiranyl.

33. A conjugate having the structure:

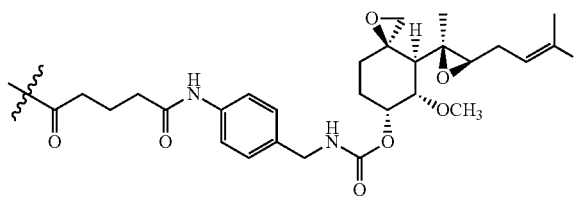

conjugated to a polyal which is a conjugation product of poly(1-hydroxymethylethylene hydroxymethyl-formal) conjugated to glutaric acid (PHF-GA), or a pharmaceutically acceptable salt thereof, wherein the PHF has a molecular weight from about 40 kDa to about 100 kDa.

34. A pharmaceutical composition comprising the conjugate of claim 33 or the pharmaceutically acceptable salt thereof, and a pharmaceutically acceptable carrier.

35. The pharmaceutical composition of claim 34, comprising one or more buffers.

36. The pharmaceutical composition of claim 35, wherein the buffer is citric acid, citrate, succinate, lactate, formic acid, bicarbonate, or 4-(2-hydroxyethyl)-1-piperazineethanesulfonic acid (HEPES).

37. The pharmaceutical composition of claim 36, further comprising a bulking agent.

38. The pharmaceutical composition of claim 37, wherein the bulking agent is mannitol.

39. The pharmaceutical composition of claim 38, further comprising a surfactant.

40. The pharmaceutical composition of claim 39, wherein the surfactant is polysorbate, hydroxypropyl-β-cyclodextrin or poloxamer.

41. The pharmaceutical composition of claim 34, which is a dry lyophilized powder or water-free concentrate.

42. The conjugate of claim 33 or a pharmaceutically acceptable salt thereof, wherein the PHF has a molecular weight of about 70 kDa.

43. A process for producing a conjugate comprising a) dissolving poly(1-hydroxymethylethylene hydroxymethyl-formal) conjugated to glutaric acid (PHF-GA) in a solution of dimethyl formamide (DMF) in water;

b) adding to the resulting solution of step a) a compound having the structure:

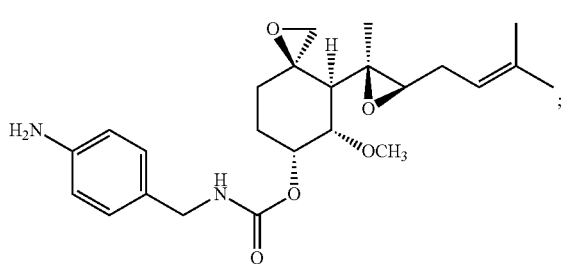

c) cooling the resulting solution of step b) and adding to the solution 1-ethyl-3-(3-dimethylaminopropyl)carbodiimide hydrochloride (EDC); and d) purifying the conjugate.

44. The process of claim 43, wherein in step b) the pH is adjusted to 5.9-6.0 following addition of the compound.

45. The process of claim 44, wherein in step c) cooling is performed to reach 0° C., and the solution of step c) is stirred for 2.5-4.0 hours.

46. The process of claim 44, wherein the PHF has a molecular weight of about 70 kDa.

47. The conjugate of claim 10 or a pharmaceutically acceptable salt thereof, wherein the conjugation product is poly(1-hydroxymethylethylene hydroxymethyl-formal) conjugated to glutaric acid.

48. The conjugate of claim 14 or a pharmaceutically acceptable salt thereof, wherein the conjugation product is poly(1-hydroxymethylethylene hydroxymethyl-formal) conjugated to glutaric acid.

49. The conjugate of claim 3 or a pharmaceutically acceptable salt thereof, wherein Z is a conjugation product of poly (1-hydroxymethylethylene hydroxymethyl-formal) (PHF).

50. The conjugate of claim 49 or a pharmaceutically acceptable salt thereof, wherein the conjugation product is poly(1-hydroxymethylethylene hydroxymethyl-formal) conjugated to glutaric acid.

* * * * *